US010265339B2

(12) United States Patent
Andrews et al.

(10) Patent No.: US 10,265,339 B2
(45) Date of Patent: Apr. 23, 2019

(54) METHODS AND COMPOSITIONS FOR TREATING CANCERS AND ENHANCING THERAPEUTIC IMMUNITY BY SELECTIVELY REDUCING IMMUNOMODULATORY M2 MONOCYTES

(71) Applicant: THOMAS JEFFERSON UNIVERSITY, Philadelphia, PA (US)

(72) Inventors: David W. Andrews, Philadelphia, PA (US); Douglas C. Hooper, Medford, NJ (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 15/983,796

(22) Filed: May 18, 2018

(65) Prior Publication Data

US 2018/0271894 A1 Sep. 27, 2018

Related U.S. Application Data

(63) Continuation of application No. 15/095,877, filed on Apr. 11, 2016.

(60) Provisional application No. 62/145,758, filed on Apr. 10, 2015.

(51) Int. Cl.
| | | |
|---|---|---|
| *C07H 21/04* | (2006.01) | |
| *A61K 31/713* | (2006.01) | |
| *A61K 31/7125* | (2006.01) | |
| *C12N 15/113* | (2010.01) | |
| *A61K 45/06* | (2006.01) | |

(52) U.S. Cl.
CPC ........ *A61K 31/713* (2013.01); *A61K 31/7125* (2013.01); *A61K 45/06* (2013.01); *C12N 15/1138* (2013.01); *C12N 2310/11* (2013.01); *C12N 2310/315* (2013.01)

(58) Field of Classification Search
CPC .................................................. C12N 15/111
See application file for complete search history.

(56) References Cited

U.S. PATENT DOCUMENTS

| | | | |
|---|---|---|---|
| 5,643,788 | A | 7/1997 | Baserga et al. |
| 5,714,170 | A | 2/1998 | Baserga et al. |
| 3,331,526 | A1 | 12/2001 | Baserga et al. |
| 6,331,526 | B1 | 12/2001 | Baserga et al. |
| 3,340,674 | A1 | 1/2002 | Baserga et al. |
| 6,541,036 | B1 | 4/2003 | Andrews et al. |
| 2011/0092572 | A1 | 4/2011 | Tachas et al. |
| 2017/0056430 | A1 | 3/2017 | Andrews et al. |
| 2018/0201939 | A1 | 7/2018 | Andrews et al. |
| 2018/0235996 | A1 | 8/2018 | Andrews et al. |
| 2018/0256625 | A1 | 9/2018 | Andrews et al. |

FOREIGN PATENT DOCUMENTS

| | | |
|---|---|---|
| WO | 96/14746 A1 | 5/1996 |
| WO | 00/09145 A1 | 2/2000 |
| WO | 2016164916 A1 | 10/2016 |

OTHER PUBLICATIONS

Schillachi, R., et al., "Immunization with Murine Breast Cancer Cells Treated with Antisense Oligodeoxynucleotides to Type I Insulin-Like Growth Factor Receptor Induced an Antitumoral Effect Mediated by a CD8+ Response Involving Fas/Fas Ligand Cytotoxic Pathway", The Journal of Immunology, vol. 176, pp. 3426-3437, 2006.
"Pilot Immunotherapy Trial for Recurrent Malignant Gliomas", ClinicalTrials.gov, NCT01550523, Study Completed, First Received Feb. 14, 2012, Verified Dec. 2013 by Thomas Jefferson University 4 pages. https://clinicaltrials.gov/ct2/show/NCT01550523?term=%22diffusion+chamber%22&rank=2 [downloaded Mar. 18, 2017].
Andrews, D.W., et al., "Results of a Pilot Study Involving the Use of an Antisense Oligodeoxynucleotide Directed Against the Insulin-Like Growth Factor Type I Receptor in Malignant Astrocytomas", Journal of Clinical Oncology, vol. 19, No. 8, pp. 2189-2200, 2001.
De Vries, M., et al., "Tumor-Associated Macrophages Are Related to Volumetric Growth of Vestibular Schwannomas", Otology & Neurology, vol. 34, No. 2, pp. 347-352, 2011.
International Preliminary Report on Patentability, PCT Application No. PCT/US2016/026970, dated Oct. 10, 2017, 6 pages.
Morin-Brureau, M., et al., "Enhancement of glioma-specific immunity in mice by 'NOBEL', an insulin-like growth factor 1 receptor antisense oligodeoxynucleotide", Cancer Immunol Immunother, vol. 64, No. 4, pp. 447-457, 2015.
Okwan-Duodu, D., et al., "Obesity-driven inflammation and cancer risk: role of myeloid derived suppressor cells and alternately activated macrophages", Am. J. Cancer Res., vol. 3, No. 1, pp. 21-33, 2013.
Stein, D., et al., "The polarity of the dorsoventral axis in the *Drosophila* embryo is defined by an extracellular signal", Cell, vol. 65, No. 5, pp. 725-735, 1991.
"Antisense102: Pilot Immunotherapy for Newly Diagnosed Malignant Giloma", ClinicalTrials.gov, NCT02507583, First Received Jun. 29, 2015, Verified Apr. 2016 by Thomas Jefferson University, 4 pages. https://clinicaltrials.gov/ct2/show/NCT02507583?term=NCT02507583&rank=1 [downloaded Mar. 18, 2017].
"Pilot Immunotherapy Trial for Recurrent Malignant Gliomas", ClinicalTrials.gov, NCT01550523, Study Completed, First Received Feb. 14, 2012, Verified Dec. 2013 by Thomas Jefferson University 4 pages. https://clnicaltrials.gov/ct2/show/NCT01550523?term=%22diffusion+chamber%22&rank=2 [downloaded Mar. 18, 2017].

(Continued)

*Primary Examiner* — Kimberly Chong
(74) *Attorney, Agent, or Firm* — Cozen O'Connor

(57) ABSTRACT

The present disclosure provides pharmaceutical compositions comprising nucleic acids capable of targeting IGF-1R expression in M2 cells. The present disclosure also provides methods for the selective reduction of M2 cells by targeting expression of IGF-1R in these cells. The present disclosure further provides methods for treating cancer and enhancing therapeutic by targeting expression of IGF-1R in M2 cells in patients. The pharmaceutical composition of the present invention is effective when administered systemically to subjects in need thereof. The ease of administration of the pharmaceutical composition facilitates treatment and enhances patient compliance.

24 Claims, 73 Drawing Sheets
Specification includes a Sequence Listing.

(56) References Cited

OTHER PUBLICATIONS

Andrews, D.W., et al., "Results of a Pilot Study Involving the Use of an Antisense Oligodeoxynucleotide Directed Against the Insulin-Like Growth Factor Type I Receptor in Malignant Astrocytomas", Journal of Clinical Oncology, vol. 19, No. 8, pp. 2189-2200, 2001.

Andrews, D.W., et al., "Phase 1 Trial of Vaccination with Autologous Tumor Cells and Antisense Directed Against the Insulin Growth Factor Type I Receptor (IGF-1R AS ODN) in Patients with Recurrent Malignant Glioma", Department of Neurological Surgery, Thomas Jefferson University, Philadelphia, PA, 10 pages, Feb. 12, 2016.

Baserga, R., et al., "The role of the IGF-I receptor in apoptosis", Vitamins & Hormones, vol. 53, pp. 65-98, 1997.

De Vries, M., et al., "Tumor-Associated Macrophages Are Related to Volumetric Growth of Vestibular Schwannomas", Otology & Neurology, vol. 34, No. 2, pp. 347-352, 2013.

Harshyne, L.A., et al., "Glioblastoma exosomes and IGF-1R/AS-ODN are immunogenic stimuli in a translational research immunotherapy paradigm", Cancer Immunol Immunother, vol. 64, No. 3, pp. 299-309, 2015.

Harshyne, L.A., et al., "Th2 bias in glioblastoma patient peripheral blood", Neuro-Oncology, vol. 18, No. 2, pp. 206-215 (Advance Access Publication Jul. 14, 2015).

International Preliminary Report on Patentability, PCT Application No. PCT/US2016/026970, dated Oct. 10, 2017, 3 pages.

International Search Report, PCT Application No. PCT/US2016/026970, dated Jul. 29, 2016, 4 pages.

Jin, X., et al., "Cell surface Nestin is a biomarker for glioma stem cells", Biochem Biophys Res Commun., vol. 433, No. 4, pp. 496-501, 2013.

Kanno, H., et al., "Expression of CD163 prevents apoptosis through the production of granulocyte colony-stimulating factor in meningioma", Neuro-Oncology, vol. 15, No. 7, pp. 853-865, 2013 (Advance Access publication Mar. 28, 2013).

Martinez, F.O., et al., "Transcriptional Profiling of the Human Monocyte-to-Macrophage Differentiation and Polarization: New Molecules and Patterns of Gene Expression", J. Immunol., vol. 177, pp. 7303-7311, 2006.

Morin-Brureau, M., et al., "Enhancement of glioma-specific immunity in mice by 'NOBEL', an insulin-like growth factor 1 receptor antisense oligodeoxynucleotide", Cancer Immunol Immunother, vol. 64, No. 4, pp. 447-457, 2015.

Okwan-Duodu, D., et al., "Obesity-driven inflammation and cancer risk: role of myeloid derived suppressor cells an alternately activated macrophages", Am. J. Cancer Res., vol. 3, No. 1, pp. 21-33, 2013.

Prosniak, M., et al., "Glioma Grade is Associated with the Accumulation and Activity of Cells Bearing M2 Monocyte Markers", Clinical Cancer Research, vol. 19, No. 14, pp. 3776-3786, 2013 (Published Online First Jun. 5, 2013).

Stein, D., et al., "The polarity of the dorsoventral axis in the *Drosophila* embryo is defined by an extracellular signal", 7, Cell. vol. 65, No. 5, pp. 725-735, 1991.

Written Opinion of the International Searching Authority, PCT Application No. PCT/US2016/026970, dated Jul. 29, 2016.

Dlouhy et al., "Emerging technology in intracranial neuroendoscopy: application of the NICO Myriad," Neurosurgical Focus, Apr. 2011; 30(4):EG, 9 pages. doi: 10.3171/2011.2.FOCUS10312.

Schillaci, R., et al., "Immunization with Murine Breast Cancer Cells Treated with Antisense Oligodeoxynucleotides to Type I Insulin-Like Growth Factor Receptor Induced an Antitumoral Effect Mediated by a CD8+ Response Involving Fas/Fas Ligand Cytotoxic Pathway", The Journal of Immunology, vol. 176, pp. 3426-3437, 2006.

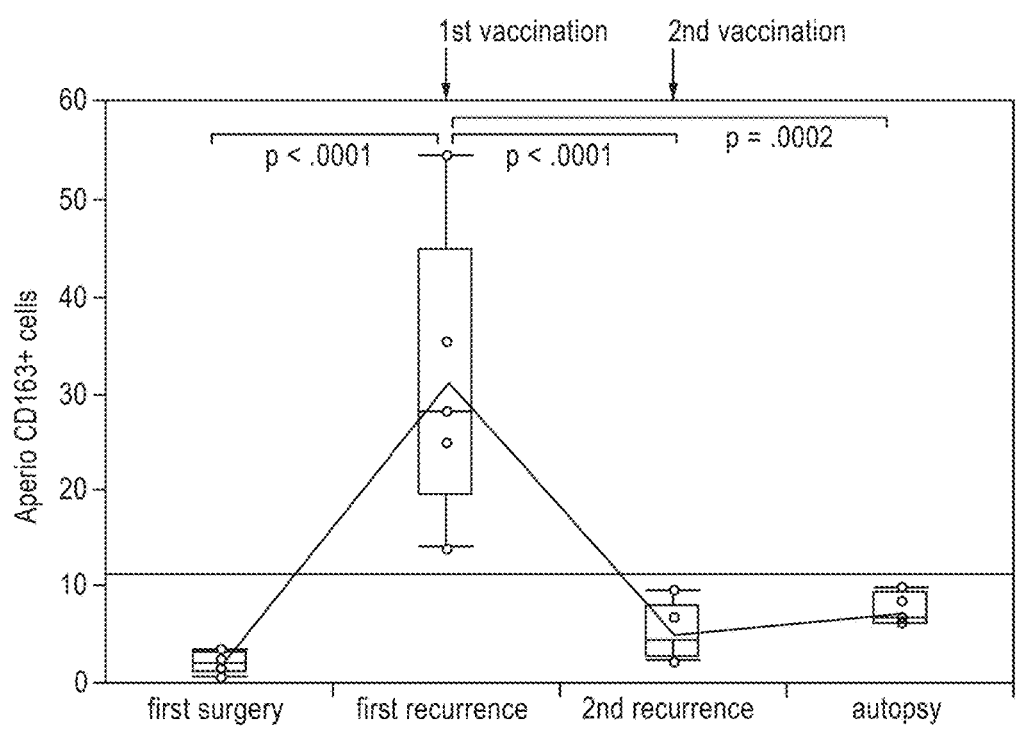

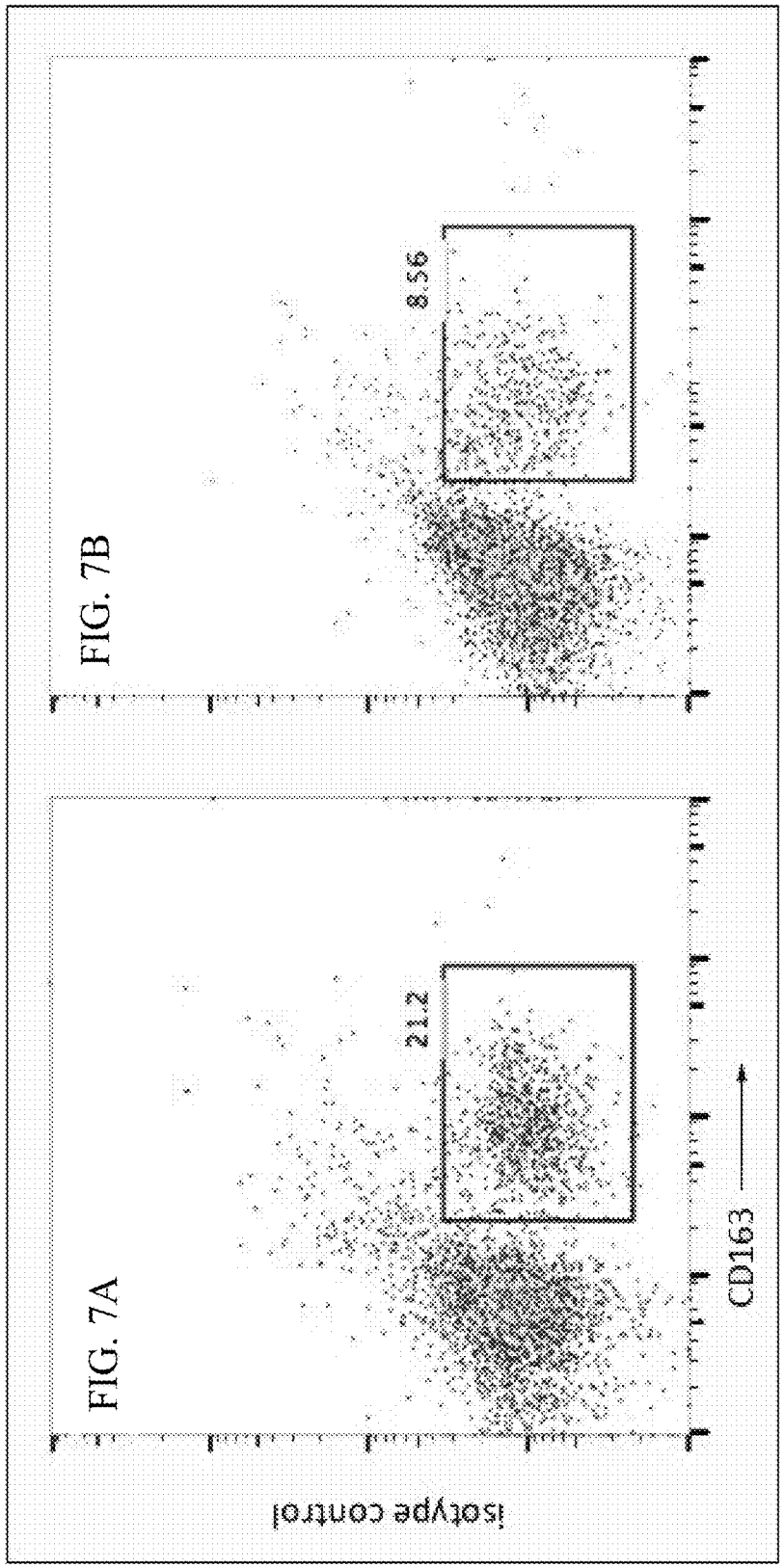

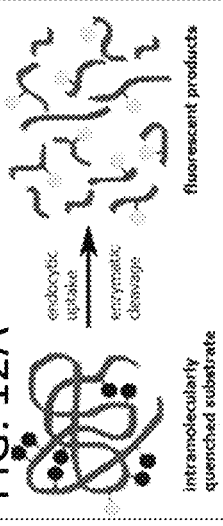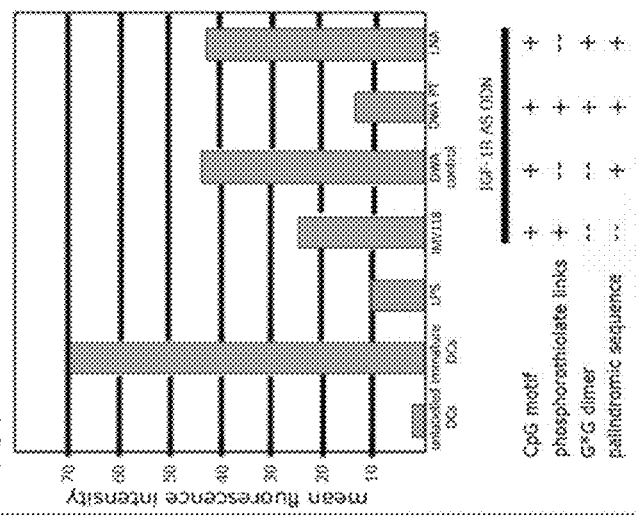

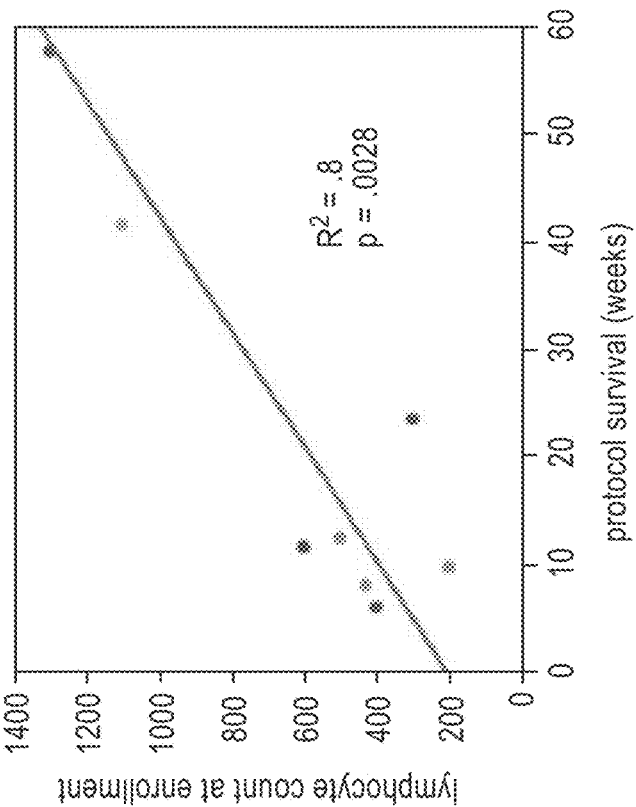
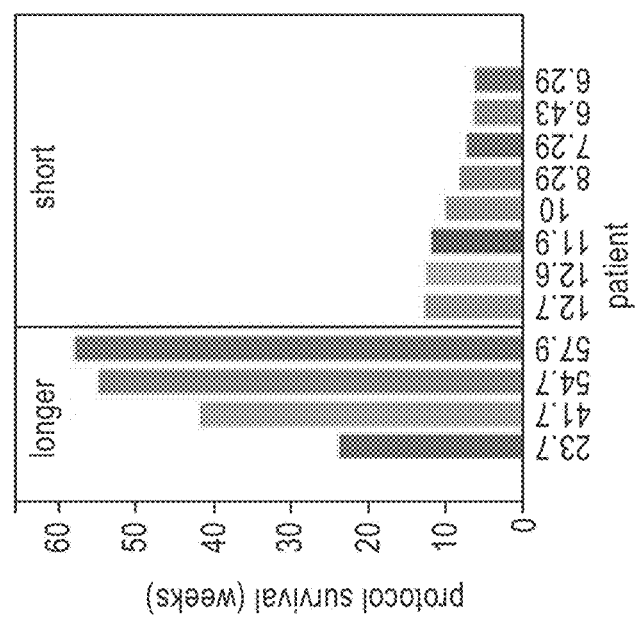

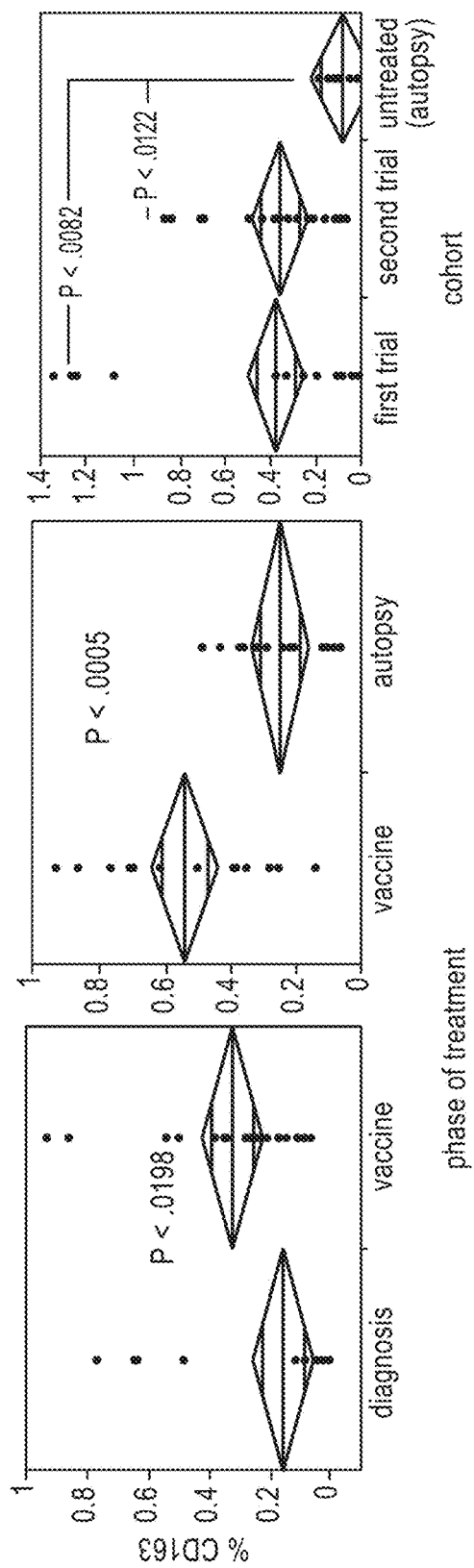

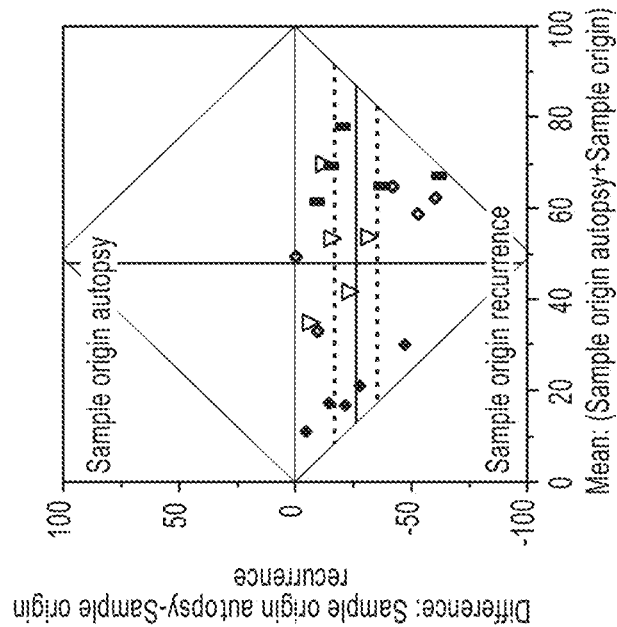
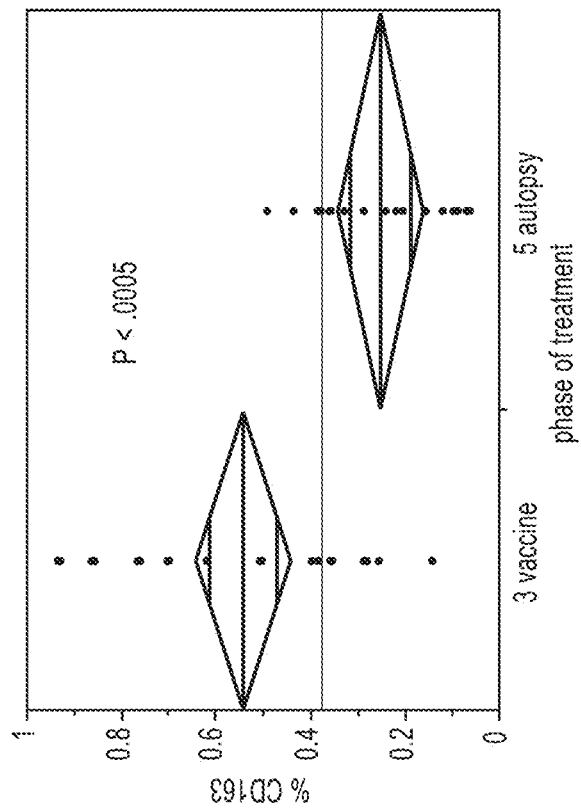
FIG. 26B

Effect on M1 and M2 cells
(AS 24h, then polarize 48h)

Comparison of Means

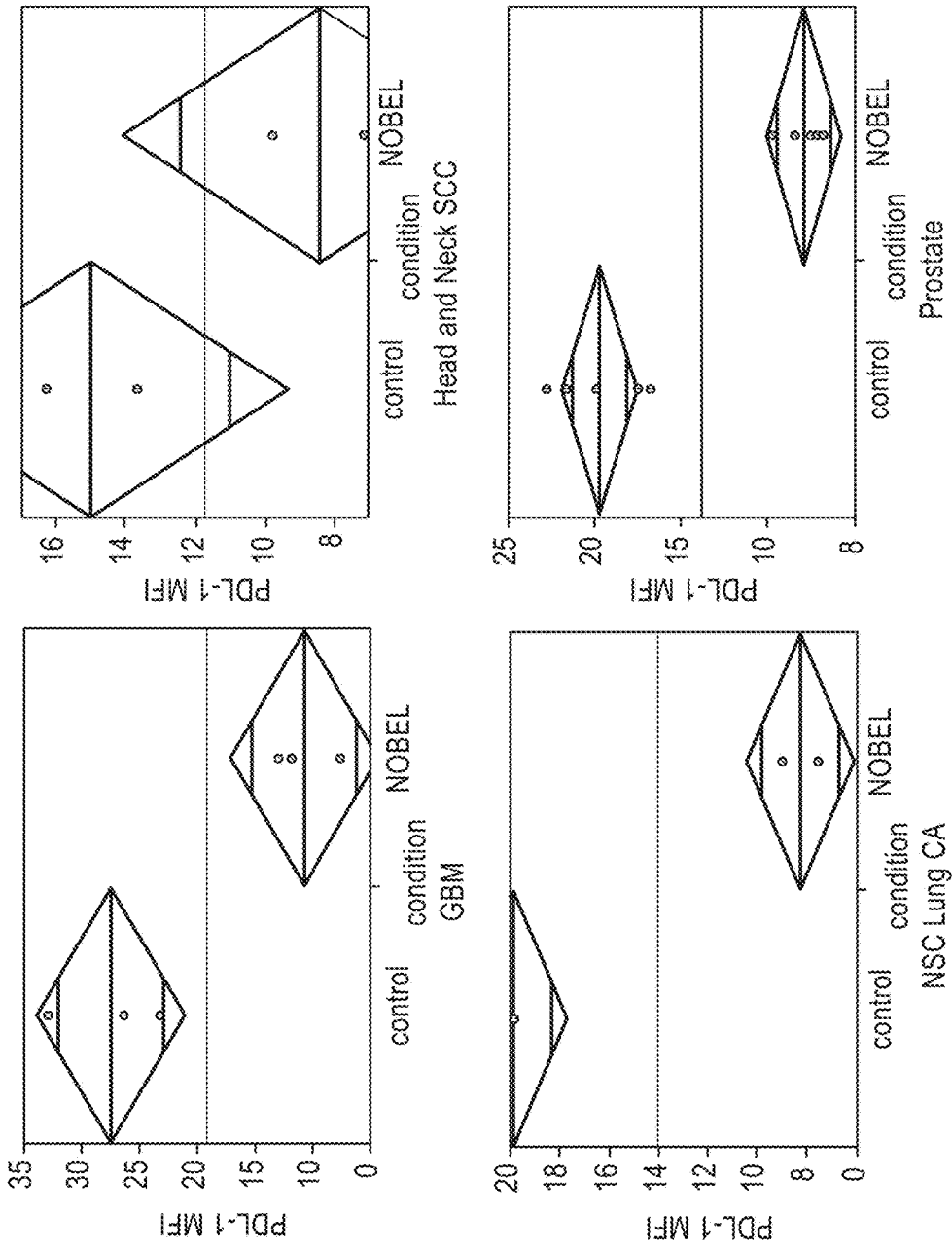
FIG. 31A  Comparison of Means

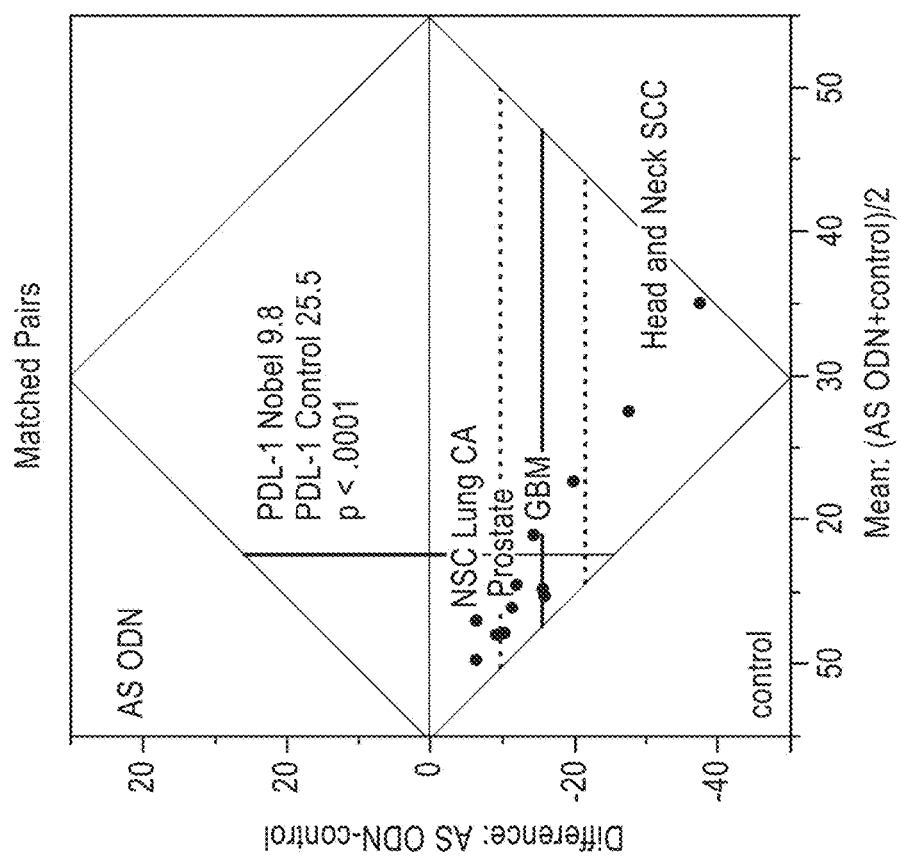

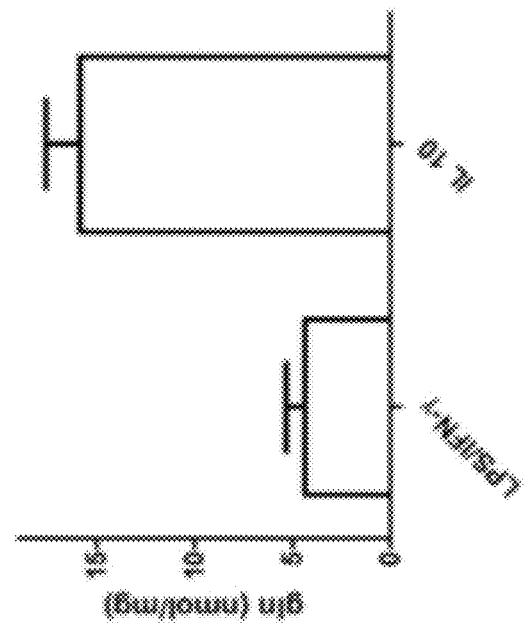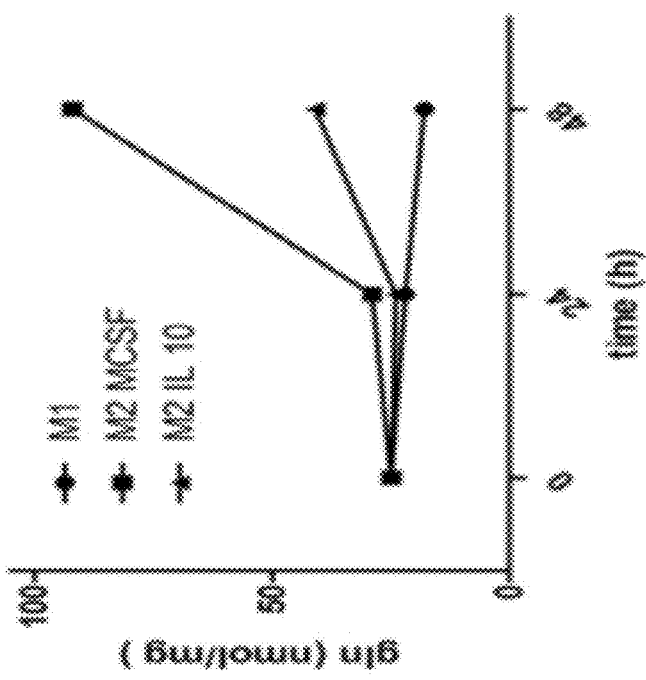
FIG. 32B
FIG. 32A

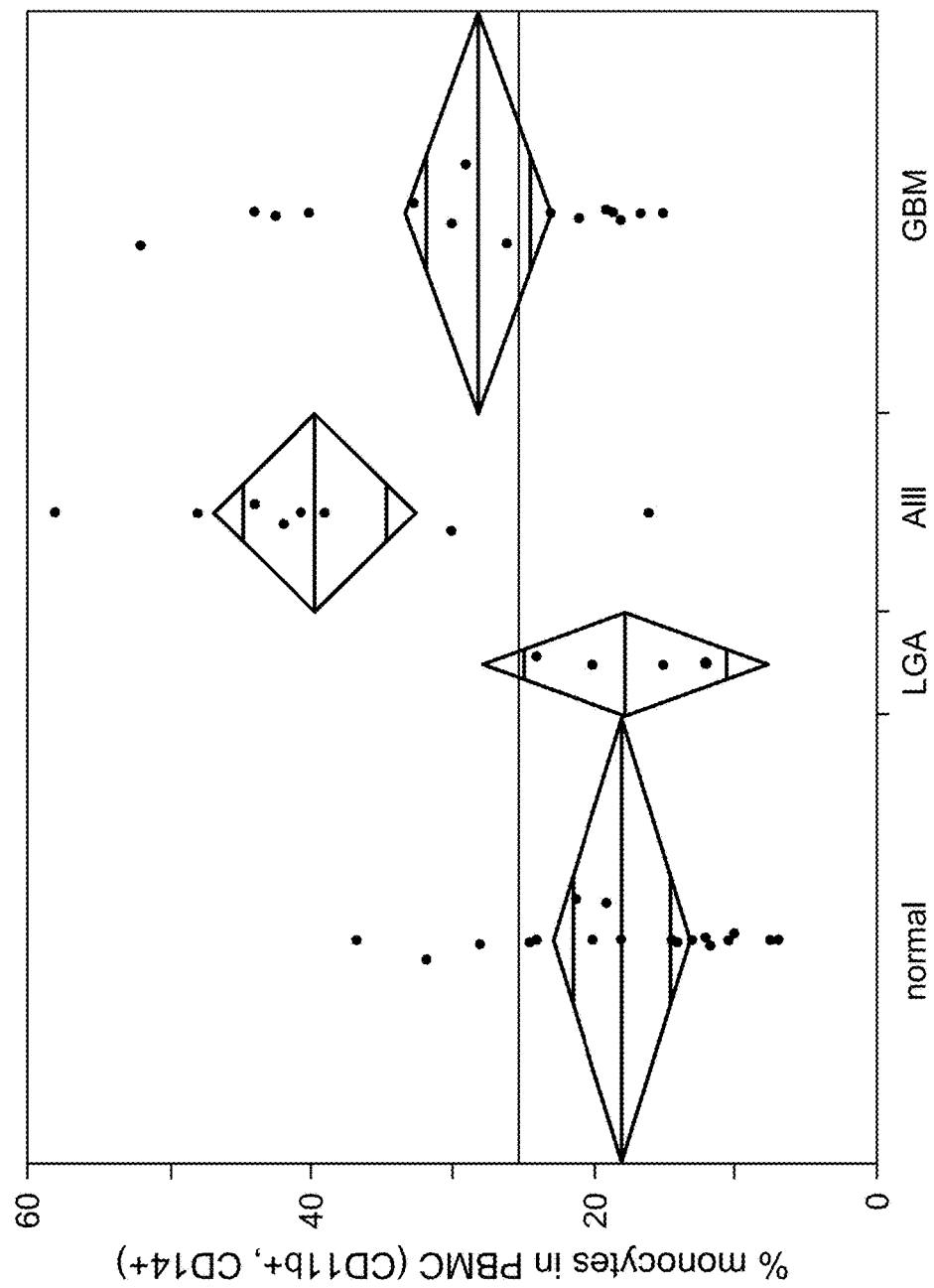

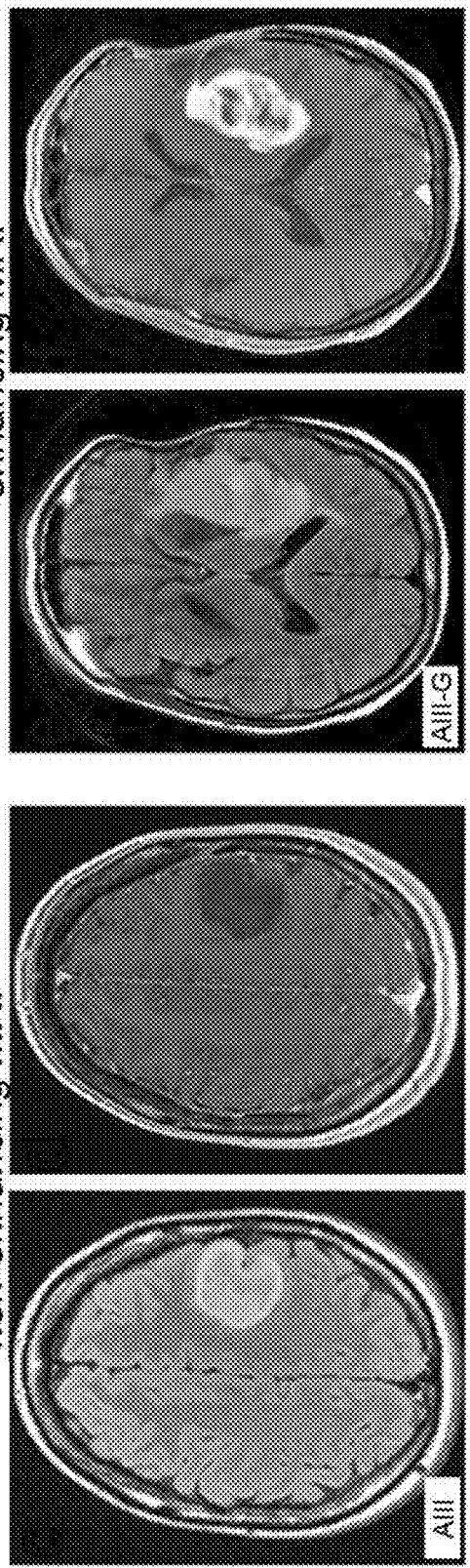

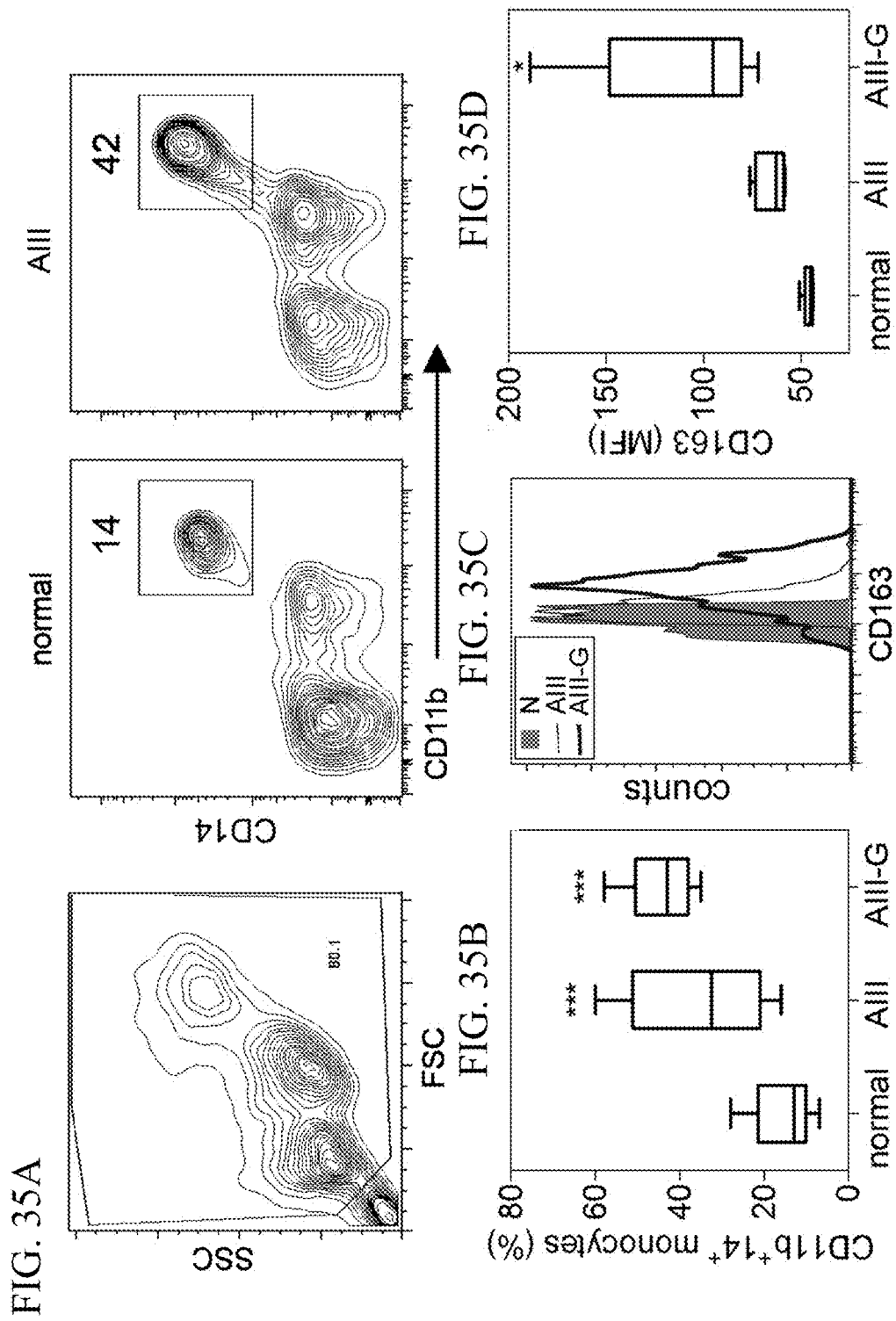

METHODS AND COMPOSITIONS FOR TREATING CANCERS AND ENHANCING THERAPEUTIC IMMUNITY BY SELECTIVELY REDUCING IMMUNOMODULATORY M2 MONOCYTES

CROSS-REFERENCE TO RELATED APPLICATIONS

This application is a continuation of U.S. patent application Ser. No. 15/095,877, filed Apr. 11, 2016, which claims the benefit of U.S. Provisional Application Ser. No. 62/145,758 filed Apr. 10, 2015, the disclosure of which is incorporated herein in its entirety for all purposes.

FIELD OF INVENTION

The present disclosure relates to methods and compositions for treating cancers and enhancing therapeutic immunity by selectively reducing M2 cells by targeting these cells with antisense nucleic acids directed against Insulin-like Growth Factor 1 Receptor (IGF-1R).

DESCRIPTION OF THE TEXT FILE SUBMITTED ELECTRONICALLY

The contents of the text file submitted electronically herewith are incorporated herein by reference in their entirety: a computer readable format copy of the sequence listing (filename: IMVX_002_01US_SeqList_ST25.txt, date recorded: Apr. 11, 2016, file size 12 kilobytes).

BACKGROUND

Monocytes are a type of white blood cell that originate from myeloid progenitors in bone marrow. From there they enter the peripheral blood stream and later migrate into tissues. In the tissues, after exposure to local growth factors, pro-inflammatory cytokines, and microbial compounds, monocytes differentiate into macrophages and dendritic cells. Macrophages derived from monocyte precursors undergo specific differentiation into the classically polarized (M1) macrophages and the non-classically activated (M2) macrophages. Normally, macrophages serve three main functions in the immune system. These are phagocytosis, antigen presentation, and cytokine presentation. In addition, certain types of cancers (such as, for example, breast cancer, astrocytoma, head and neck squamous cell cancer, papillary renal cell carcinoma Type II, lung cancer, pancreatic cancer, gall bladder cancer, rectal cancer, glioma, classical Hodgkin's lymphoma, ovarian cancer, and colorectal cancer) exhibit elevated levels of M2-like macrophages within the tumor and similar M2 monocytes circulating in the periphery. Despite advances in cancer therapy, the prognosis for these cancers remains poor and attempts to treat these cancers using conventional treatments such as, for example, chemotherapy, external beam radiation, and brachytherapy have led to only marginal improvements in progression-free survival and overall survival. Therefore, there is a need in the art to obtain new and improved treatments for such cancers.

SUMMARY OF THE INVENTION

In some aspects, the disclosure provides a pharmaceutical composition comprising an effective amount of an Insulin-like Growth Factor 1 Receptor antisense oligodeoxynucleotide (IGF-1R AS ODN), wherein administering the pharmaceutical composition to a subject having M2 cells in their circulation, tumor microenvironment, or serum that polarizes undifferentiated monocytes towards M2 cells reduces the number of M2 cells in the subject.

In other aspects, the disclosure provides a method for selective elimination of M2 cells in a subject comprising systemically administering to the subject an effective amount of the pharmaceutical composition.

In other embodiments, the disclosure provides a method of treating cancer by reducing the number of M2 cells comprising systemically administering to a subject suffering from the cancer an effective amount of the pharmaceutical composition.

In yet other embodiments, the disclosure provides a method for enhancing immune response in a subject comprising systemically administering to the subject an effective amount of the pharmaceutical composition.

DESCRIPTION OF THE DRAWINGS

FIG. 1 depicts expression of CD163+ cells in the periphery of patients with glioma. This subset of monocytes is initiated by the presence of the tumor, and this subpopulation supports tumor growth and invasion due to its angiogenic and immunosuppressive nature. Glioma grade is associated with the accumulation and activity of cells bearing M2 monocyte markers. The presence of this population of M2-like CD163+ macrophages within the tumor and similar M2 monocytes in the circulating periphery also subverts any pro-inflammatory anti-tumor vaccine strategies.

FIG. 3A details that IGF-1R AS ODN selectively targets the removal of M2 macrophages such that in situations where these cells predominate, their tumor promoting effects can be eliminated and therapeutic Th1 immunity can be rescued. Open circles represent differentiated, unstimulated cells, and closed circles represent differentiated and stimulated cells. FIG. 3B depicts the difference in monocyte subset distribution after treatment with IGF-1R AS ODN according to macrophage polarization.

FIG. 4 depicts quantification of tumor associated CD163+ cells in a patient throughout the course of treatments. Mean and SD of 5400× fields were determined by Aperio quantification. Four time points are provided, a first surgery, first recurrence, second recurrence, and autopsy and the Aperio CD163+ cells on the y axis. FIG. 4 shows that the methods disclosed herein are effective in reducing CD163+ cells for patients that have failed standard therapy.

FIG. 6A-FIG. 6C: Avecia lot production of DWA sequence; FIG. 6D-FIG. 6F: Girindus lot production of NOBEL sequence; FIG. 6A and FIG. 6D: stability of AS ODN in lyophilized powder form; FIG. 6B and FIG. 6E: formulation in sterile saline; FIG. 6C and FIG. 6F: formulation in sterile saline. Stability results of IMV118 LOT # GAI-08-060-S3-B1 reveal the smallest degradation product is ~300 Da, and therefore the measured spectral mass meets the requirement of 5709±300 Da and acceptable stability in storage to date from lot release. The Avecia sequence (DWA) reveals stability over a nine year period.

FIG. 7 shows that circulating CD68+CD163+ cells are reduced in animals at least 14 days after receiving one dose of NOBEL (SEQ ID NO: 1) systemically (i.p.) following GL261 implantation in the CNS. NOBEL is an 18-mer phosphorothioate oligodeoxynucleotide IGF1-R antisense oligodeoxynucleotide (AS ODN) starting with six nucleotides downstream from the initiating methionine codon. NOBEL is manufactured by solid phase organic synthesis using well-established methodology in a synthesizer equipped with a closed chemical column reactor using flow-through technology. Each synthesis cycle sequence on the solid support consists of multiple steps, which are carried out sequentially until the full-length oligonucleotide is established. NOBEL is then lyophilized, packaged in a HDPE container with screw cap and then vacuum-heat-sealed inside a 5-mL Mylar pouch for storage at −80° C. Prior to use, the lyophilized powder is dissolved in saline until a 100 mg/mL solution is achieved. The resulting solution is sterile filtered through a 0.22 μm membrane filter. 1 mL aliquots are filled into USP Type 1 glass vials and sealed with an appropriate rubber stopper and aluminum cap prior to storage at −80° C.

For this experiment, white blood cells were stained with biotinylated anti-mouse CD163 (Biorbyt), washed, and a secondary streptavidin-APC added. After two washes and fixation, cells were permeabilized and stained intracellularly with anti-mouse CD68-PE, followed by two washes with perm-buffer and a final PBS wash to close membranes. Samples were run on a Millipore Guava flow cytometer and analyzed using FlowJo. Samples taken at sacrifice show a substantial shift in WBC populations following i.p. administration of NOBEL. FIG. 7A. PBS i.p. injection control; FIG. 7B. NOBEL i.p. injection.

FIG. 12 shows that the CpG motif, 5'G*G motif, and phosphorothioate linkages all provide an additional maturation stimuli to dendritic cells. FIG. 12A: Immature DCs are highly endocytic and engulf large amounts of fluorescent protein (upper panel) resulting in higher fluorescent intensities. FIG. 12B: Monocyte-derived DC were incubated in the presence of various IGF-1R/AS ODN (1 μg/ml) for 24 hrs. LPS-treated DCs (1 μg/ml) served as a positive control for maturation. Immature DCs engulfed large amounts of fluorescent protein resulting in higher fluorescent intensities (depicted by larger bars). Mature DCs (activated) down-regulate endocytosis and as a result, take up less fluorescent protein and possess low fluorescent intensities (depicted by smaller bars). CpG motifs contained in IGF-1R/AS ODN also provide maturation stimuli to DCs (see control and LNA DC). Phosphorothioate linkages provide an additional maturation stimuli to DC (see NOBEL DC). 5' G*G motif provides a third maturational stimuli to DCs (see DWA PT DC). The oligomers tested included SEQ ID NO: 1 (NOBEL), SEQ ID NO: 11 (IDT1220 phosphorothioate AS ODN (IDT1220)), SEQ ID NO: 15 (DWA phosphorothioate AS ODN (DWA PT)), SEQ ID NO: 16 (DWA locked nucleic acid AS ODN (LNA)), and SEQ ID NO: 17 (DWA phosphodiester AS ODN (DWA control)).

FIG. 14 shows NOBEL (SEQ ID NO: 1) titration in GL261. Cells were plated 20 k per well in 96-well plate with growth media and incubated for 4 hr (37 C, 5% $CO_2$ humidified); growth media was removed and serum-free Opti-MEM (100 μL) with desired AS ODN concentration was added to each well. Cells were returned to culture for an additional 24 hr.

FIG. 19A-FIG. 19D depicts a safety assessment study. FIG. 19A. overall survival of patients in trial; FIG. 19B. overall survival related to interval between surgeries; FIG. 19C. protocol survival with two survival cohorts. Nine patients died of disease progression while one died of intracerebral hemorrhage and two of sepsis. Overall protocol survival was 48.2 weeks and 9.2 weeks, respectively for longer (N=4) and short (N=8) survival cohorts (log-rank=0.0025). FIG. 19C. Excluding non-disease progression cause of death, median survival was 48.2 weeks and 10 weeks, respectively for longer (N=4) and short cohorts (N=5) respectively (log-rank=0.0049); FIG. 19D. excluding one outlier (long cohort) linear regression revealed high correlation between protocol survival and lymphocyte count at enrollment ($R^2$=0.8, p=0.0028).

FIG. 20A. examples of short survival cohort. TJ12: A-D; TJ10: E-H; A, E: pre-operative T1-gadolinium enhanced axial images; G: T1-gadolinium-enhanced coronal image; C: pre-operative axial FLAIR image; B, D, F, H: respective 3 month post-operative images; FIG. 20B. examples of longer survival cohort. TJ06: A-D; TJ09: E-H. A, E: pre-operative T1-gadolinium-enhanced axial images; C, F: pre-operative axial FLAIR images; B, D, F, H: respective 3 month post-operative images; FIG. 20C. relationship between relative cerebral blood volume in tumor v. apparent diffusion coefficient in short survival cohort; FIG. 20D. longer survival cohort; there is a high correlation between the apparent diffusion coefficient (ADC) and relative cerebral blood volume (rCBV) ($R^2$=0.96, p=0.0005); FIG. 20E. summary of cytokine responses in the longer survival cohort (N=3); FIG. 20F. example of CD163+ cell loss as it relates to rCBV and ADC over time in patient TJ06; also assay of activated nitric oxide synthetase, an agent of hyperemia, reflected as serum nitrate levels (Greiss assay) as they relate to rCBV.

FIG. 21A-FIG. 21C shows an examination of explanted chambers and pathological specimens. FIG. 21A. photomicrograph composite of chamber explant from TJ09; left column: PBS chamber; right column: vaccine chamber; upper row: H&E stain of outer surface of membranes; lower row: CD163+ immunostain of outer surface membranes; FIG. 21B. immunofluorescent stains for CD163 (red); a. CD163+ TAMs in tumor of patient TJ14 at initial resection; b. CD163+ TAMs in tumor of patient TJ14 at recurrence prior to vaccination; CD163+ TAMs were increased; c. CD163+ TAMs in tumor of patient TJ14 at second recurrence; a loss of TAMs in tumor microenvironment was observed, and CD163 TAMs were found associated only with blood vessel; d, e, f. higher magnifications, respectively; FIG. 20C. Aperio immunostain quantification of CD163+ TAMs according to stage of treatment (Left Two Panels); also noted are similar levels in both Phase I trials but significantly lower levels in undiagnosed, untreated patients who underwent autopsy (Right Panel).

FIG. 22A. absolute CD4 and CD8 counts compared to relative amounts of WBC among PBMC; FIG. 22B. levels of CCL21 and CXCL12; FIG. 22C. relationship of relative T-cell and macrophage counts; FIG. 22D. relationship of relative proportion of CD14+CD16− macrophages with CCR2 and MCP-1 (CCL2); FIG. 22E. putative Th-1 cytokine responses after vaccinations.

FIG. 24 depicts radiographic responses of anatomic tumors. FIG. 24A and FIG. 24B: patient TJ06 and FIG. 24A and FIG. 24D, patient TJ07; FIG. 24B and FIG. 24D: delayed PET/CT images in same axial registration. In FIG. 24B note photopenia including lack of normal increased metabolism of left temporal lobe cortical ribbon compared to right temporal lobe; small area of increased metabolism in anterolateral temporal lobe. The majority of enhancement in FIG. 24A is interpreted as inflammation. In FIG. 24D note distinct correlation of increased metabolism with corresponding volume of enhancement in FIG. 24C which is interpreted as disease progression.

FIG. 26A-FIG. 26D depicts an examination of explanted chambers and pathologic specimens. FIG. 26A left panel: Comparison of means for number of immunopositive cells/ 400× field CD163 TAMs at initial diagnosis v. recurrence prior to vaccination; right panel: matched pairs comparison mean difference 19.2% increase, p<0.0001; FIG. 26B left panel: Comparison of means for number of CD163 TAMs at recurrence prior to vaccination v. autopsy; right panel: matched pairs comparison mean difference −26.35% decrease, p<0.0001; FIG. 26C. retrospective comparison of CD163 TAMs in paraffin samples from the original trial and the current trial v. six autopsy specimens from undiagnosed and untreated glioblastomas; FIG. 26D. assessment of IGF-1R+ cells in paraffin sections obtained at initial diagnosis, recurrence prior to vaccination, and at autopsy.

FIG. 27.

FIG. 28A. absolute CD4 and CD8 counts compared to relative amounts of WBC among PBMC; FIG. 28B. levels of CCL21 and CXCL12; FIG. 28C. relationship of relative T-cell and macrophage counts; FIG. 28D. relationship of relative proportion of CD14+CD16− macrophages with CCR2 and MCP-1 (CCL2); FIG. 28E. putative Th-1 cytokine responses after vaccinations.

FIG. 30A. comparison of means for PBS control v. IGF-1R AS ODN (NOBEL, 250 µg) treatment of CD163+ macrophages; FIG. 30B. matched pairs analysis reveals highly significant decrease in M2 cell population.

FIG. 31A and FIG. 31B show that monocytes polarized towards the M2 CD163+ phenotype by treatment with sera from patients with different cancers show upregulation of both CD163 as well as PDL-1; in both cases treatment with AS ODN knocks down both CD163 and PDL-1 by selectively targeting this population of cells. FIG. 31A. comparison of means for PBS control v. IGF-1R AS ODN (NOBEL, 250 µg) treatment of CD163+ macrophages expressing PDL-1; FIG. 30B. matched pairs analysis reveals highly significant decrease in this cell population reflected as significant reduction of PDL-1.

FIG. 32 shows that monocytes polarized towards M2 by treatment with IL-10 produce substantially more glutamine (gln) than monocytes polarized towards M1 by treatment with LPS/IFNγ and are therefore more likely to promote the growth of tumor cells. Normal human monocytes were polarized towards M1 and M2 in vitro by treatment with LPS/IFNγ and MCSF or IL10 respectively. FIG. 32A. levels of glutamine accumulating in the culture medium at various time points; FIG. 32B. shows intracellular glutamine levels assessed at 24 hours of culture.

FIG. 33A-FIG. 33C shows the difference in circulating CD163+ monocytes between normal individuals and astrocytoma patients. FIG. 33A: normal individual with ~6% CD14+ monocytes in their circulation with intermediate levels of CD163. Two changes are observed in the cancer patient—higher numbers of monocytes and the monocytes have higher levels of CD163. Other cells (red box) do not have CD163 at all. FIG. 33B: normal individuals can have a wide range of monocytes, due to infections etc. (FIG. 33B, cells positive for CD11b+CD14) but these are elevated in patients with malignant astrocytomas. The histogram in FIG. 33C shows that monocytes from cancer patients have higher levels of CD163 on their CD14 monocytes than control cells (red histogram).

FIG. 35 shows that the numbers of circulating monocytes are elevated in AIII and AIII-G patients and express increasing levels of the M2 marker CD163. PBMC from 18 randomly selected Anaplastic Astrocytoma (AA) patients (i.e., patients with astrocytomas characterized morphologically by WHO histological criteria as grade III) and 24 normal donors were stained with antibodies specific for CD11b, CD14, and CD163 and assessed by flow cytometry. Forward scatter (FSC) and side scatter (SSC) profiles were used to establish a live cell gate and monocytes were defined as live cells expressing CD11b and CD14 (FIG. 35A). Representative contour plots for the live gate and analysis of CD11b and CD14 positivity in PBMC from a normal and an AA donor are shown in FIG. 35A where axes are presented as log scale and the numbers indicate the frequency of gated cells. FIG. 35B is a summary chart showing the frequency of CD11b+CD14$^+$ monocytes in PBMC from 12 patients with AIII, 6 patients with AIII-G, and 24 normal individuals determined by flow cytometry. The statistical significance of differences in cell percentages between normal individuals and AA patient subsets was assessed by Student's t test (, p<0.01). The median fluorescence intensity (MFI) for CD163 staining of CD11b+CD14+ gated monocytes is overlayed from representative histogram plots of AIII, AIII-G, and normal blood specimens in FIG. 35**C. Axes are presented as log scale. The MFI for CD163-staining of the gated monocyte subset in PBMC samples from the different donor groups are presented in FIG. 35D.

DETAILED DESCRIPTION

Figures 1A, 1B:
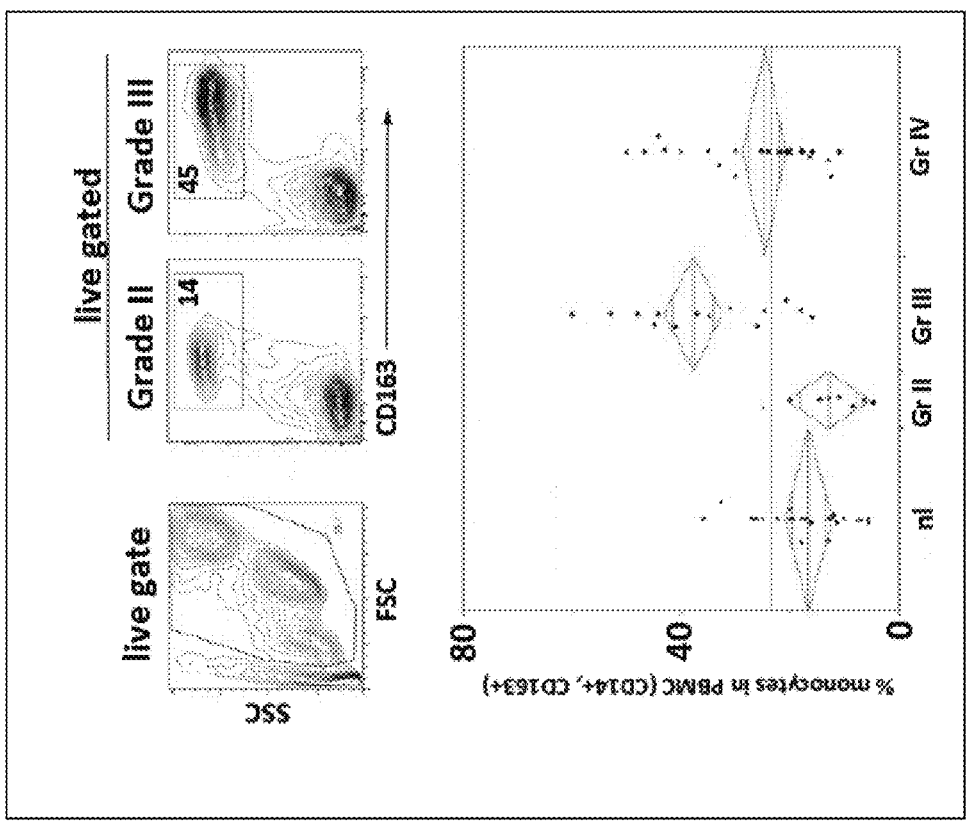
FIG. 1A. flow cytometry reflecting an increase in CD14+ cells in WHO Grade III astrocytomas is depicted.
FIG. 1B. graphical representation comparing levels of CD163+ cells according to WHO grade. Grade III and Grade IV tumors show significantly different % monocytes in PMBC as compared to either normal subjects or WHO Grade II astrocytomas.
Figure 2A:
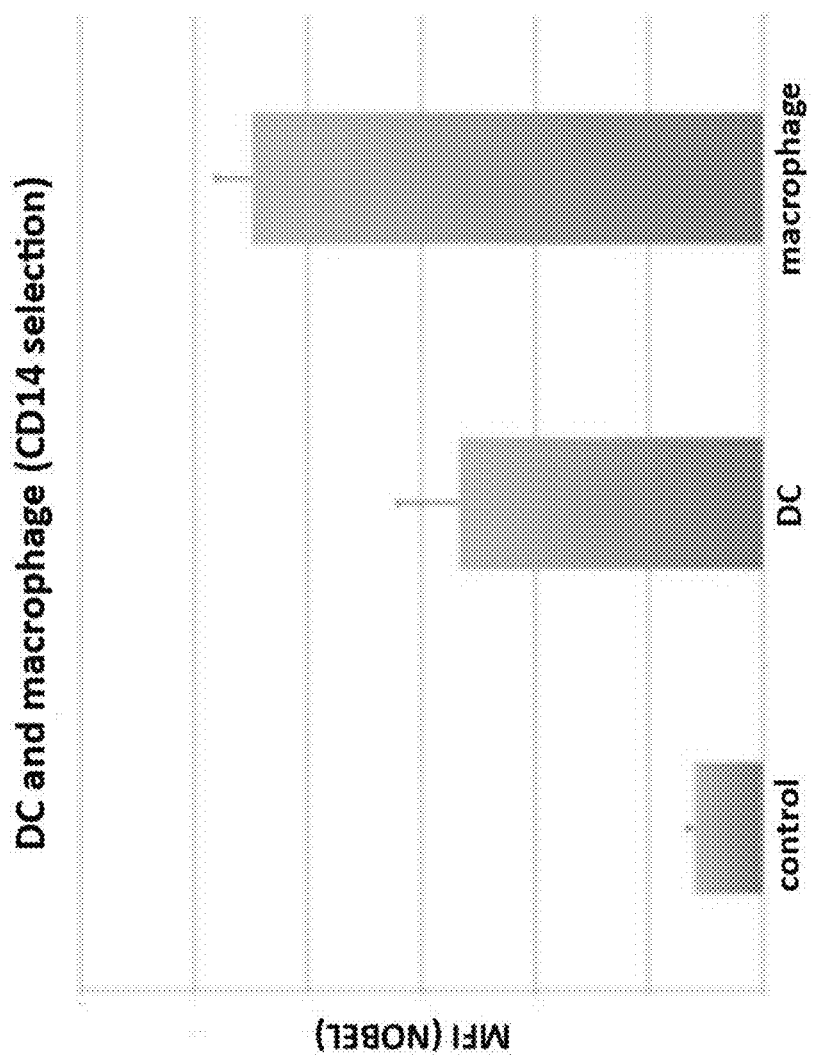
FIG. 2A and FIG. 2B depict uptake of labeled antisense nucleic acids directed against Insulin-like Growth Factor 1 Receptor (IFG-1R AS ODN) according to cell type (FIG. 2A) and immunotype (FIG. 2B). Macrophages (CD14+) derived from tumor and matched blood samples in glioma patients avidly uptake antisense directed against the insulin-like growth factor type 1 receptor (IGF-1R AS ODN).
Figure 2B:
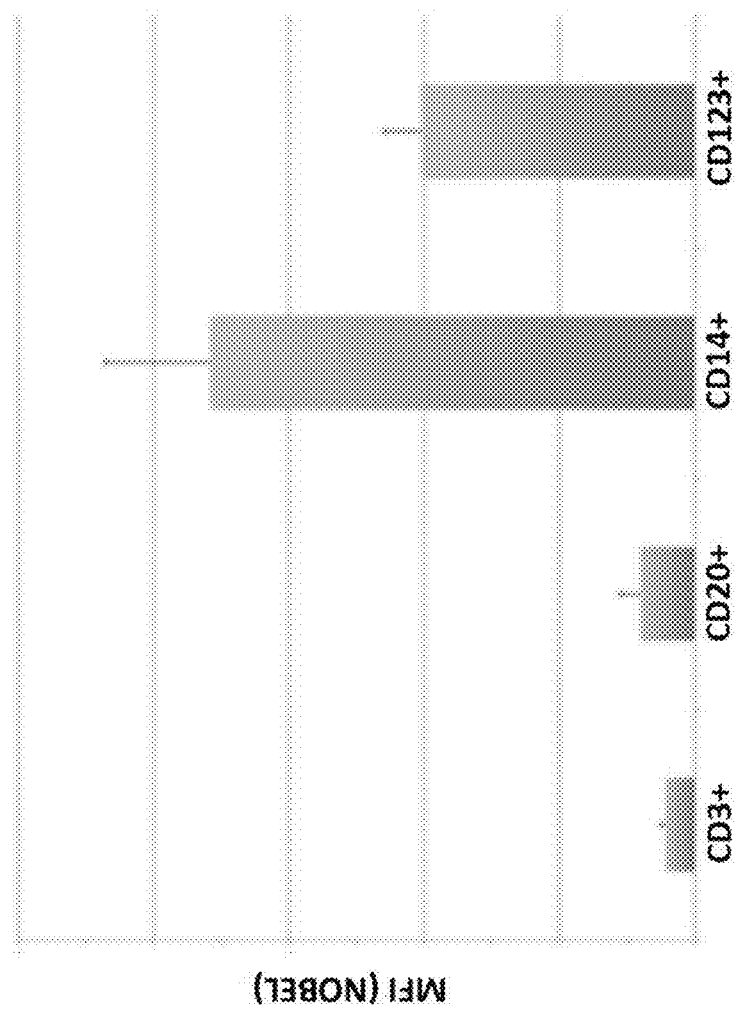

The present disclosure shows, for the first time, that a critical distinction between M1 and M2 cells is that the M2 subpopulation produces higher levels of the insulin-like growth factor type 1 receptor (IGF-1R) than the M1 subpopulation. This indicates that IGF-1R plays a critical role in the polarization and survival of the M2 cells. Indeed, the present disclosure shows that although both M1 and M2 cells avidly uptake antisense nucleic acids directed against IGF-1R (IGF-1R AS ODN), the IGF-1R AS ODN induces a selective reduction in M2 cells derived from cancer patients over M1 cells in a dose-dependent manner. More importantly, the present disclosure shows that the selective reduction of M2 cells leads to a regression of the cancer in these patients. Therefore, this specification provides, for the first time, a viable and efficient mechanism of treating certain cancers by selectively reducing the number of M2 cells in patients by systemically administering IGF-1R AS ODN.

Additionally, in patients suffering from certain types of cancers including, but not limited to, glioma, astrocytoma, breast cancer, head and neck squamous cell cancer, papillary renal cell carcinoma Type II, lung cancer, pancreatic cancer, gall bladder cancer, rectal cancer, classical Hodgkin's lymphoma, ovarian cancer, and colorectal cancer, M2 cells cause the tumor environment to be immunomodulatory towards Type 2 immunity, which suppresses Type 1 immunity and defeats an immunotherapy strategy. M2 cells, thereby, attenuate induction of therapeutic anti-tumor immunity. Consequently, treatments that seek to improve Th1 immunity either fail or have reduced efficacy in view of the M2 cells present in these patients. The present disclosure shows for the first time that reducing the M2 subpopulation also promotes Type 1 immunity in cancer patients. The disclosure shows that by targeting and neutralizing the M2 cell population, the capacity to engender Type 1, protective anti-tumor immunity is restored in cancer patients, thereby facilitating treatments using immunotherapy strategies.

Even more significantly, the present disclosure shows that the selective reduction of M2 cells by administration of the IGF-1R AS ODN provides a mechanism for delaying the onset of cancer or even preventing cancer in subjects. Therefore, using the IGF-1R AS ODN to selectively knockdown M2 cells provides a new and significant immunotherapy approach for the treatment and prevention of cancer as well as for enhancing therapeutic immunity in cancer patients. Therefore, the present disclosure provides new information about the immune system and supports a therapeutic intervention involving targeted elimination of M2 cells associated with poor prognosis in patients with a variety of cancers.

Accordingly, the present disclosure provides pharmaceutical compositions comprising nucleic acids capable of targeting IGF-1R expression in M2 cells. The present disclosure also provides methods for the selective reduction of M2 cells by targeting expression of IGF-1R in these cells. The present disclosure further provides methods for treating cancer by targeting expression of IGF-1R in M2 cells in patients. Importantly, the pharmaceutical composition of the present invention is effective when administered systemically to subjects in need thereof. The ease of administration of the pharmaceutical composition facilitates treatment and enhances patient compliance.

The term "selective as used herein refers to an effect which affects M2 cells, but does not affect M1 cells. Alternatively, it may refer to an effect which affects M2 cells to a greater extent in comparison to M1 cells. For example, a selective reduction in the number of M2 cells does not affect the number of M1 cells, or causes a greater reduction in the number of M2 cells in comparison to a reduction in the number of M1 cells.

The term "targeting IGF-1R expression" or "targets IGF-1R expression" as used herein refers to administering a nucleic acid that has a sequence designed to bind to the IGF-1R.

The term "M2 cells" as used herein encompasses M2 macrophages present within tumors of a subject and/or M2 monocytes circulating in the periphery of the subject.

The term "M1 cells" as used herein encompasses M1 macrophages present within the tissues of a subject and/or M1 monocytes circulating in the periphery of the subject.

As used herein, terms such as "a," "an," and "the" include singular and plural referents unless the context clearly demands otherwise.

As used herein, the term "about" when preceding a numerical value indicates the value plus or minus a range of 10%. For example, "about 100" encompasses 90 and 110.

In some embodiments, the disclosure provides a pharmaceutical composition comprising an effective amount of a nucleic acid that targets IGF-1R expression in M2 cells, wherein administering the pharmaceutical composition to a patient suffering from cancer causes a reduction in M2 cells.

In certain embodiments, the disclosure provides a pharmaceutical composition comprising an effective amount of a nucleic acid capable of targeting IGF-1R expression in M2 cells, wherein administering the pharmaceutical composition to a patient suffering from cancer causes a downregulation of expression of IGF-1R in M2 cells. In other embodiments, the disclosure provides a pharmaceutical composition comprising an effective amount of a nucleic acid capable of targeting IGF-1R expression in M2 cells, wherein administering the pharmaceutical composition to a patient suffering from cancer causes a downregulation of expression of genes other than IGF-1R in M2 cells.

In some embodiments, the nucleic acid downregulates the expression of genes downstream of IGF-1R pathway in a cell. In certain aspects, the downstream gene is hexokinase (Hex II). In some embodiments, the nucleic acid downregulates the expression of housekeeping genes in the cell. In some aspects, the housekeeping gene is L13.

In some embodiments the nucleic acid is a naturally occurring nucleic acid. In other embodiments, the nucleic acid is a non-naturally occurring nucleic acid. In certain aspects the nucleic acid is recombinantly produced. In some embodiments, the nucleic acid is recombinantly produced in a microorganism. In some aspects, the nucleic acid is recombinantly produced in bacteria. In other embodiments, the nucleic acid is recombinantly produced in a mammalian cell line. In yet other embodiments, the nucleic acid is recombinantly produced in an insect cell line.

In certain aspects, the nucleic acid is chemically synthesized. In certain embodiments, the nucleic acid is manufactured by solid phase organic synthesis. In some aspects, the synthesis of the nucleic acid is carried out in a synthesizer equipped with a closed chemical column reactor using flow-through technology. In some embodiments, each synthesis cycle sequence on the solid support consists of multiple steps, which are carried out sequentially until the full-length nucleic acid is obtained. In certain embodiments, the nucleic acid is stored in a liquid form. In other embodiments, the nucleic acid is lyophilized prior to storing. In some aspects, the lyophilized nucleic acid is dissolved in water prior to use. In other embodiments, the lyophilized nucleic acid is dissolved in an organic solvent prior to use. In yet other embodiment, the lyophilized nucleic acid is formulated into a pharmaceutical composition. In some aspects the pharmaceutical composition is a liquid pharmaceutical composition. In other aspects, the pharmaceutical composition is a solid pharmaceutical composition.

In some embodiments the nucleic acid is an RNA. In other embodiments, the nucleic acid is a DNA. In yet other embodiments, the nucleic acid is an RNAi molecule. In further embodiments, the nucleic acid is an oligonucleotide.

In certain embodiments, the nucleic acid is an antisense oligomer. In some aspects, the nucleic acid is an antisense oligodeoxynucleotide (AS ODN). Antisense oligomers work at the molecular level by binding to a targeted complimentary sequence of mRNA by Watson and Crick base-pairing rules. The translation of target mRNA is inhibited by an active and/or passive mechanism when hybridization occurs between the complementary helices. In the passive mechanism, hybridization between the mRNA and exogenous nucleotide sequence leads to duplex formation that prevents the ribosomal complex from reading the message. In the active mechanism, hybridization promotes the binding of RnaseH, which destroys the RNA but leaves the AS ODN intact to hybridize with another complementary mRNA target. Either or both mechanisms inhibit translation of a protein contributing to or sustaining a malignant phenotype. As therapeutic agents, they are far more selective and as a result, more effective and less toxic than conventional drugs. The presence of one or more phosphorothioate modifications stabilize the oligomer by conferring nuclease resistance and thereby increase its half-life.

In some embodiments, the nucleic acid comprises a modified phosphate backbone. In certain aspects, the phosphate backbone modification renders the nucleic acid more resistant to nuclease degradation. In certain embodiments, the modification is a locked nucleic acid modification. In other embodiments, the modification is a phosphorothioate linkage. In certain aspects, the nucleic acid contains one or more phosphorothioate linkages. In certain embodiments, the phosphorothioate linkages renders the nucleic acid more resistant to nuclease cleavage. In some embodiments, the nucleic acid may be partially phosphorothioate-linked. For example, up to about 1%, up to about 3%, up to about 5%, up to about 10%, up to about 20%, up to about 30%, up to about 40%, up to about 50% up to about 60%, up to about 70%, up to about 80%, up to about 90%, up to about 95%, or up to about 99% of the nucleic acid may be phosphorothioate-linked. In some embodiments, the nucleic acid is fully phosphorothioate-linked. In other embodiments, phosphorothioate linkages may alternate with phosphodiester linkages. In certain embodiments, the nucleic acid has at least one terminal phosphorothioate monophosphate.

In some embodiments, the nucleic acid comprises one or more CpG motifs. In other embodiments, the nucleic acid does not comprise a CpG motif. In certain aspects, the one or more CpG motifs are methylated. In other aspects, the one or more CpG motifs are unmethylated. In certain embodiments, the one or more unmethylated CpG motifs elicit an innate immune response when the nucleic acid is administered to a subject. In some aspects, the innate immune response is mediated by binding of the unmethylated CpG-containing nucleic acid to Toll like Receptors (TLR). In some aspects, the TLR is TLR9. In other aspects, binding of TLR to the unmethylated CpG-containing nucleic acid causes activation of TLR9. In certain aspects, the activated TLR9 is expressed on B-cells. In other aspects, the activated TLR is expressed on plasmacytoid dendritic cells. In certain aspects, the activation of TLR9 may be measured by secretion of cytokines by B-cells. In one aspect, the cytokine is IL-6. In another aspect, the cytokine is IL-10. In other aspects, the activation of TLR9 may be measured by secretion of cytokines by plasmacytoid dendritic cells. In one aspect, the cytokine is IFNα. In another aspect, the cytokine is IFNβ. In yet another aspect, the cytokine is TNFα.

In certain embodiments, the nucleic acid comprises at least one terminal modification or "cap". The cap may be a 5' and/or a 3'-cap structure. The terms "cap" or "end-cap" include chemical modifications at either terminus of the oligonucleotide (with respect to terminal ribonucleotides), and including modifications at the linkage between the last two nucleotides on the 5' end and the last two nucleotides on the 3' end. The cap structure may increase resistance of the nucleic acid to exonucleases without compromising molecular interactions with the target sequence or cellular machinery. Such modifications may be selected on the basis of their increased potency in vitro or in vivo. The cap can be present at the 5'-terminus (5'-cap) or at the 3'-terminus (3'-cap) or can be present on both ends. In certain embodiments, the 5'- and/or 3'-cap is independently selected from phosphorothioate monophosphate, abasic residue (moiety), phosphorothioate linkage, 4'-thio nucleotide, carbocyclic nucleotide, phosphorodithioate linkage, inverted nucleotide or inverted abasic moiety (2'-3' or 3'-3'), phosphorodithioate monophosphate, and methylphosphonate moiety. The phosphorothioate or phosphorodithioate linkage(s), when part of a cap structure, are generally positioned between the two terminal nucleotides on the 5' end and the two terminal nucleotides on the 3' end.

In certain embodiments, the nucleic acid targets the expression of specific genes in a cell. In some embodiments, the nucleic acid targets the expression of one or more growth factors in a cell. In some embodiments, the growth factor is Insulin like Growth Factor 1 Receptor (IGF-1R). IGF-1R is a tyrosine kinase cell surface receptor that shares 70% homology with the insulin receptor. When activated by its ligands (IGF-I, IGF-II and insulin), it regulates broad cellular functions including proliferation, transformation and cell survival. The IGF-1R is not an absolute requirement for normal growth, but it is essential for growth in anchorage-independent conditions that may occur in malignant tissues. A review of the role of IGF-IR in tumors is provided in Baserga et al., *Vitamins and Hormones*, 53:65-98 (1997), which is incorporated herein by reference in its entirety.

In certain embodiments, the nucleic acid is an oligonucleotide directed against DNA or RNA of a growth factor or growth factor receptor, such as, for example, IGF-IR.

In certain embodiments, the cell is a mammalian cell. In other embodiments, the cell is a cell of the immune system including, but not limited to, monocytes, neutrophils, eosinophils, basophils, leukocytes, Natural Killer (NK) cells, lymphocytes, T cells, B cells, dendritic cells, mast cells, and macrophages.

In certain embodiments, the cell is a macrophage. In certain aspects, the macrophage is a M2 macrophage. In certain aspects, the M2 macrophage expresses one or more cell surface markers including, but not limited to, CD11b, CD14, CD15, CD23, CD64, CD68, CD163, CD204, CD206, and/or other M2 macrophage markers commonly known in the art.

In other embodiments, the cell is a monocyte. In certain aspects, the monocyte is a M2 monocyte. In certain aspects, the M2 monocyte expresses one or more cell surface markers including, but not limited to, CD11b, CD14, CD15, CD23, CD64, CD68, CD163, CD204, CD206, and/or other M2 monocyte markers commonly known in the art.

In certain embodiments, the nucleic acid downregulates IGF-1R expression in any cell. In other embodiments, the nucleic acid downregulates IGF-1R expression in M2 cells. In certain embodiments, IGF-1R expression in M2 cells is downregulated by at least about 1%, at least about 2%, at least about 5%, at least about 10%, at least about 20%, at least about 30%, at least about 40%, at least about 50%, at least about 60%, at least about 70%, at least about 80%, at least about 90%, or at least about 95% in comparison to M2 cells not treated with the nucleic acid. IGF-1R expression in M2 cells may be measured by quantitative RT-PCR.

In certain aspects, IGF-1R expression in M2 cells is downregulated in about 10 minutes, about 20 minutes, about 30 minutes, about 40 minutes, about 50 minutes, about 1 hour, about 2 hours, about 3 hours, about 6 hours, about 12 hours, about 24 hours, about 48 hours, or about 72 hours after administration of the nucleic acid to the subject.

In some embodiments, IGF-1R expression in M2 cells remains downregulated in the subject for at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 3 weeks, at least about 4 weeks, at least about 5 weeks, or at least about 6 weeks after receiving one dose of the nucleic acid.

In some aspects, the downregulation of expression of IGF-1R in M2 cells causes a selective reduction of M2 cells in a subject in comparison to M1 cells. In certain aspects, targeting the expression of IGF-1R in M2 cells causes a selective reduction of M2 cells in a subject in comparison to M1 cells.

In certain embodiments, M2 cells in a subject are reduced by at least about 2%, at least about 5%, at least about 10%, at least about 20%, at least about 30%, at least about 40%, at least about 50%, at least about 60%, at least about 70%, at least about 80%, at least about 90%, or at least about 95% in comparison to a subject in need of treatment with the nucleic acid targeting IGF-1R expression in M2 cells; for example, the subject prior to treatment. In some embodiments, the M2 cells in the subject are reduced by at least about 40%. In other aspects, the M2 cell population is eliminated. For example, after administration of the pharmaceutical composition of the present invention, the M2 cell population may be about 1%, about 2%, about 5%, or about 10% of the population before administration of the pharmaceutical composition. M2 cells in a subject may be measured using FACS. In certain aspects, after treatment the M2 cells are eliminated; i.e., undetectable by FACS.

In certain aspects, the reduction in M2 cells is observed in about 10 minutes, about 20 minutes, about 30 minutes, about 40 minutes, about 50 minutes, about 1 hour, about 2 hours, about 3 hours, about 6 hours, about 12 hours, about 24 hours, at about 48 hours, or about 72 hours after administration of the nucleic acid to the patient.

In some embodiments, the reduction in M2 cells in the subject is sustained for at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 3 weeks, at least about 4 weeks, at least about 5 weeks, or at least about 6 weeks after receiving one dose of the nucleic acid.

In some embodiments, targeting the expression of IGF-1R prevents undifferentiated monocytes from being polarized to M2 cells. In other embodiments, targeting the expression of IGF-1R in M2 cells causes the M2 cells to either lose their M2 phenotypic and functional properties, or undergo cell death. In certain embodiments, the cell death is necrosis. In other embodiments, the cell death is apoptosis. Apoptosis, for purposes of this invention, is defined as programmed cell death and includes, but is not limited to, regression of primary and metastatic tumors. Apoptosis is a programmed cell death which is a widespread phenomenon that plays a crucial role in the myriad of physiological and pathological processes. Necrosis, in contrast, is an accidental cell death which is the cell's response to a variety of harmful conditions and toxic substances. In yet other embodiments, targeting the expression of IGF-1R in M2 cells causes the M2 cells to undergo cell cycle arrest.

In certain embodiments, the nucleic acid of the invention is an antisense deoxynucleotide directed against IGF-1R (IGF-1R AS ODN). The full length coding sequence of IGF-1R is shown in SEQ ID NO:19. In certain aspects, the nucleic acid may have at least about 70%, at least about 75%, at least about 80%, at least about 85%, at least about 90%, at least about 95%, at least about 96%, at least about 98%, or 100% identity to the IGF-1R AS ODN. Percentage identity can be calculated using the alignment program ClustalW2, available at www.ebi.ac.uk/Tools/msa/clustalw2/ using default parameters.

In certain embodiments, the nucleic acid comprises nucleotide sequences complementary to the IGF-1R signal sequence, comprising either RNA or DNA. The signal sequence of IGF-1R is a 30 amino acid sequence. In other embodiments, the nucleic acid comprises nucleotide sequences complementary to portions of the IGF-1R signal sequence, comprising either RNA or DNA. In some embodiments, the nucleic acid comprises nucleotide sequences complementary to codons 1-309 of IGF-1R, comprising either RNA or DNA. In other embodiments, the nucleic acid comprises nucleotide sequences complementary to portions of codons 1-309 of IGF-1R, comprising either RNA or DNA.

In certain embodiments, the nucleic acid is at least about 5 nucleotides, at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, or at least about 50 nucleotides in length. In some embodiments, the nucleic acid is from about 15 nucleotides to about 22 nucleotides in length. In certain aspects, the nucleic acid is about 18 nucleotides in length.

In certain embodiments, the nucleic acid forms a secondary structure at 18° C., but does not form a secondary structure at about 37° C. In other embodiments, the nucleic acid does not form a secondary structure at about 18° C. or at about 37° C. In yet other embodiments, the nucleic acid does not form a secondary structure at any temperature. In other embodiments, the nucleic acid does not form a secondary structure at 37° C. In particular embodiments, the secondary structure is a hairpin loop structure.

In some aspects, the nucleic acid comprises any of SEQ ID NOS: 1-14, or fragments thereof. In certain embodiments, the nucleic acid may have at least about 70%, at least about 75%, at least about 80%, at least about 85%, at least about 90%, at least about 95%, at least about 96%, at least about 98%, or 100% identity to any of SEQ ID NOS: 1-14, or fragments thereof.

In some aspects, the nucleic acid consists of any of SEQ ID NOS: 1-14. In certain aspects, the nucleic acid is SEQ ID NO: 1. SEQ ID NO: 1 is referred to as NOBEL. NOBEL is an 18-mer oligodeoxynucleotide with a phosphorothioate backbone and a sequence complimentary to codons 2 through 7 in the IGF-1R gene. As such, NOBEL, is an antisense oligonucleotide directed against IGF-1R (IGF-1R AS ODN). The NOBEL sequence, derived as the complimentary sequence of the IGF-1R gene at the 5' end, is:

```
5' -TCCTCCGGAGCCAGACTT- 3'.
```

NOBEL has a stable shelf life and is resistant to nuclease degradation due to its phosphorothioate backbone. Administration of NOBEL can be provided in any of the standard methods associated with introduction of oligodeoxynucleotides known to one of ordinary skill in the art. Advantageously, the AS ODNs disclosed herein, including NOBEL, may be administered with little/no toxicity. Even levels of about 2 g/kg (scaled) based on mice tests (40 µg in the tail vain) did not reveal toxicity issues. NOBEL can be manufactured according to ordinary procedures known to one of ordinary skill in the art.

The pharmaceutical compositions disclosed herein contain the nucleic acid in addition to a pharmaceutically acceptable carrier or diluent; for example, the composition may contain saline (0.9% sodium chloride).

Dosages for the nucleic acid in human subjects may be about 0.025 g/kg, about 0.05 g/kg, about 0.1 g/kg, about 0.15 g/kg, or about 0.2 g/kg. In certain aspects, the nucleic acid is supplied as a lyophilized powder and re-suspended prior to administration. When resuspended the concentration of the nucleic acid may be about 50 mg/ml, about 100 mg/ml, about 200 mg/ml, about 500 mg/ml, about 1000 mg/ml, or a range between those amounts.

In certain embodiments, the subject is an animal. In other aspects, the subject is a human. In some embodiments, the subject is suffering from a disease. In certain aspects, the disease is cancer. In certain embodiments, the cancer includes, but is not limited to, breast cancer, astrocytoma, head and neck squamous cell cancer, papillary renal cell carcinoma Type II, lung cancer, pancreatic cancer, gall bladder cancer, rectal cancer, glioma, classical Hodgkin's lymphoma, ovarian cancer, and colorectal cancer. In certain aspects, the cancer is glioma. In particular aspects, the patient has malignant glioma. In particular aspects, the malignant glioma is a recurrent malignant glioma.

In certain embodiments, a subject who is a candidate for treatment with the nucleic acid is identified by measuring the levels of circulating monocytes in their blood. In some embodiments, the candidate has an elevated number of circulating monocytes in comparison to a healthy subject. As used herein, the term "healthy subject" refers to a subject not suffering from cancer or any other disease and not in need of treatment with the nucleic acid of the invention. In some aspects, the circulating monocytes include, but are not limited to, CD11b+, CD14+, CD15+, CD23+, CD64+, CD68+, CD163+, CD204+, or CD206+ monocytes. In certain aspects, the levels of one or more circulating monocytes are elevated by at least about 1.3 fold, at least about 1.5 fold, at least about 1.8 fold, at least about 2 fold, at least about 3 fold, at least about 4 fold, at least about 5 fold, at least about 10 fold, at least about 20 fold, at least about 30 fold, at least about 40 fold, at least about 50 fold, at least about 60 fold, at least about 70 fold, at least about 80 fold, at least about 90 fold, or at least about 100 fold in comparison to a healthy subject. In particular embodiments, the levels of one or more circulating monocytes are elevated by about 2 fold in comparison to a healthy subject. Levels of circulating monocytes in the subject may be measured using Fluorescence-Activated Cell Sorting (FACS).

In certain aspects, the subject has an elevated number of circulating CD14+ monocytes in comparison to a healthy subject. In certain aspects, the levels of circulating CD14+ monocytes are elevated by at least about 1.3 fold, at least about 1.5 fold, at least about 1.8 fold, at least about 2 fold, at least about 3 fold, at least about 4 fold, at least about 5 fold, at least about 10 fold, at least about 20 fold, at least about 30 fold, at least about 40 fold, at least about 50 fold, at least about 60 fold, at least about 70 fold, at least about 80 fold, at least about 90 fold, or at least about 100 fold in comparison to a healthy subject. In particular embodiments, the levels of the circulating CD14+ monocytes are elevated by about 2 fold in comparison to a healthy subject.

In certain embodiments, the circulating CD14+ monocytes have an elevated level of CD163 in comparison to a healthy subject. In some aspects, the levels of CD163 on the circulating CD14+ monocytes are elevated by at least about 2 fold, at least about 3 fold, at least about 4 fold, at least about 5 fold, at least about 10 fold, at least about 20 fold, at least about 30 fold, at least about 40 fold, at least about 50 fold, at least about 60 fold, at least about 70 fold, at least about 80 fold, at least about 90 fold, or at least about 100 fold in comparison to a healthy subject. In particular embodiments, the levels of CD163 on the circulating CD14+ monocytes are elevated by about 2 fold in comparison to a healthy subject.

In other embodiments, a subject who is a candidate for treatment with the nucleic acid has serum that polarizes undifferentiated monocytes towards M2 cells. In certain aspects, incubation of the subject's sera with undifferentiated monocytes induces the expression of one or more cell surface markers on the monocytes including, but not limited to, CD11b, CD14, CD15, CD23, CD64, CD68, CD163, CD204, and/or CD206. In other aspects, incubation of the subject's sera with undifferentiated monocytes elevates the expression of one or more cell surface markers on the monocytes in comparison to monocytes not incubated with the subject's sera. In certain aspects, the cell surface markers include, but are not limited to, CD11b, CD14, CD15, CD23, CD64, CD68, CD163, CD204, and/or CD206. In some aspects, the levels of one or more surface markers are elevated by at least about 1.3 fold, at least about 1.5 fold, at least about 1.8 fold, at least about 2 fold, at least about 3 fold, at least about 4 fold, at least about 5 fold, at least about 10 fold, at least about 20 fold, at least about 30 fold, at least about 40 fold, at least about 50 fold, at least about 60 fold, at least about 70 fold, at least about 80 fold, at least about 90 fold, or at least about 100 fold in comparison to undifferentiated monocytes not incubated with the subject's sera. In particular embodiments, the levels of one or more surface markers are elevated by about 2 fold in comparison to undifferentiated monocytes not incubated with the subject's sera. Monocytes polarized by a subject's sera may be measured using FACS.

In yet other embodiments, a subject who is a candidate for treatment with the nucleic acid is identified by performing a tumor biopsy on the subject. In some embodiments, tumors from the subject are assayed for the presence of monocytes. In certain aspects, the monocytes include, but are not limited to, CD11b+, CD14+, CD15+, CD23+, CD64+, CD68+, CD163+, CD204+, or CD206+ monocytes. The presence of monocytes in the tumors may be assayed using immunohistochemistry.

In certain embodiments, a subject who is a candidate for treatment with the nucleic acid shows CD163+M2 cells greater than about 10%, about 15%, about 20%, about 25%, about 30%, about 35%, about 40%, about 45%, or about 50% of the subjects total peripheral blood mononuclear cells (PBMCs). In certain aspects, the subject shows CD163+M2 cells greater than about 20% of the subject's total PBMCs.

In certain embodiments, a subject who is a candidate for treatment with the nucleic acid is suffering from WHO grade II, WHO grade III, or WHO grade IV tumor. In certain aspects, the subject is suffering from WHO grade II tumor. In some aspects, the tumor is an astrocytoma. In certain embodiments, the tumor is selected from grade II astrocytoma, AIII (IDH1 R132H mutant grade III astrocytoma), AIII-G (IDH1 wild-type grade III with characteristics of glioblastoma multiforme astrocytoma), or grade IV astrocytoma. In some aspects the grade IV astrocytoma is glioblastoma multiforme.

In some embodiments, a subject who is a candidate for treatment with the nucleic acid is identified by measuring the levels of a specific set of cytokines. In some embodiments, the subject has elevated levels of these cytokines in comparison to a healthy subject. In other embodiments, the subject is identified by detecting specific micro RNA (miRNA) present in the tumor. In particular embodiments, the subject has elevated levels of these miRNAs in comparison to a healthy subject.

In some embodiments, the nucleic acid induces regression of the cancer in the patient. In other embodiments, the nucleic acid induces a reduction of the cancer in the patient. In yet other embodiments, the nucleic acid induces an elimination of the cancer in the patient.

In some embodiments, the nucleic acid induces regression of glioma tumor in the patient. In other embodiments, the nucleic acid induces a reduction of glioma tumor in the patient. In yet other embodiments, the nucleic acid induces an elimination of glioma tumor in the patient.

In certain embodiments, the nucleic acid is formulated into a pharmaceutical composition. In some aspects, the pharmaceutical composition is formulated in a liquid form. In other aspects, the pharmaceutical composition is formulated in a solid form. In certain aspects, the pharmaceutical composition is formulated for oral administration. In certain embodiments, the pharmaceutical composition is in the form of a capsule. In other embodiments, the pharmaceutical composition is in the form of a tablet. In some aspects, the tablet is a fast-release tablet. In other aspects, the tablet is a controlled-release tablet. In other aspects, the pharmaceutical composition is formulated for intraperitoneal administration. In yet other aspects, the pharmaceutical composition is formulated for intravenous administration. In further aspects, the pharmaceutical composition is formulated for intramuscular administration.

In certain embodiments, the pharmaceutical composition is introduced into a diffusion chamber and the diffusion chamber is surgically implanted into the rectus sheath of a subject for a therapeutically effective time (see, for example, U.S. Pat. No. 6,541,036, which is incorporated herein by reference in its entirety).

As discussed, the present disclosure shows that M2 cells (but not M1 cells) avidly uptake antisense nucleic acids directed against IGF-1R (IGF-1R AS ODN) and the IGF-1R AS ODN induces a selective reduction in M2 cells derived from cancer patients over M1 cells in a dose-dependent manner. More importantly, the present disclosure shows that the selective reduction of M2 cells leads to a regression of the cancer in these patients.

Therefore, in certain embodiments is provided a method for the selective elimination of M2 cells in a patient suffering from cancer comprising administering to the patient an effective amount of the pharmaceutical composition.

In other embodiments is provided a method of treating cancer by targeting expression of IGF-1R in M2 cells comprising administering to a patient suffering from the cancer an effective amount of the pharmaceutical composition.

In certain embodiments, the method of treating cancer further comprises combination therapy. In some embodiments, the combination therapy comprises radiation therapy. In other embodiments, the combination therapy comprises chemotherapy. In certain aspects, the radiation therapy or chemotherapy is administered to the patient subsequent to administration of the pharmaceutical composition. In certain embodiments, radiation therapy or chemotherapy is administered to the patient at least about 1 hour, at least about 2 hours, at least about 3 hours, at least about 6 hours, at least about 12 hours, at least about 24 hours, at least about 48 hours, at least about 72 hours, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 3 weeks, at least about 4 weeks, at least about 5 weeks, or at least about 6 weeks subsequent to administration of the pharmaceutical composition.

anti-tumor immunity. Table 1 below, for example, summarizes possible immune modulations attributed to gliomas that may be at least in part caused by M2 cells in gliomas.

TABLE 1

Immunomodulatory Capabilities of Gliomas.

| Modulations | Consequence |
|---|---|
| Systemic and regional depletion of type 1 Th cells | Lack of antigen-specific recognition of tumor cells by the Th1 cells that drive CTL and NK responses |
| Lack of MHC Class I molecules on tumor cells | Loss of recognition by cytotoxic T cells |
| MHC class II expression on tumor cells | Regional depletion of Th1 cells |
| TGFβ production by tumor cells | Suppression of certain T-, B- and NK-cell and macrophages responses |
| Prostaglandin $E_2$ and IL-10 production by tumor cells | Suppression of Th1 and professional APC functions |
| Production of colony-stimulating factors | Recruitment and polarization of macrophages |
| Chemokine production by tumor cells | Chemotaxis of T cells and macrophages into tumor tissue; differentiation of macrophages |
| Presence of IL-1 autocrine loop in tumor cells | Partial activation of T cells and macrophages |
| Production of IL-1RA by tumor cells | Regulation of IL-1 autocrine loop; suppression of IL-1 mediated immune cascade reaction |
| Lack of IFN-α/β genes in tumor cells | Reduced innate immune reactivity |
| M2, MDSC and Treg infiltration in gliomas | Suppression of anti-tumor cytolytic T cell response |

In certain aspects, the pharmaceutical composition is administered to the patient subsequent to administration of the radiation therapy or chemotherapy. In certain embodiments, pharmaceutical composition is administered to the patient at least about 1 hour, at least about 2 hours, at least about 3 hours, at least about 6 hours, at least about 12 hours, at least about 24 hours, at least about 48 hours, at least about 72 hours, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 3 weeks, at least about 4 weeks, at least about 5 weeks, or at least about 6 weeks subsequent to administration of the radiation therapy or chemotherapy.

In certain embodiments, the radiation therapy includes, but is not limited to, internal source radiation therapy, external beam radiation therapy, and systemic radioisotope radiation therapy. In certain aspects, the radiation therapy is external beam radiation therapy. In some embodiments, the external beam radiation therapy includes, but is not limited to, gamma radiation therapy, X-ray therapy, intensity modulated radiation therapy (IMRT), and image-guided radiation therapy (IGRT). In certain embodiments, the external beam radiation therapy is gamma radiation therapy.

In certain embodiments, the AS ODN may be administered pre-operatively; for example prior to surgery to reduce tumor burden. For example, the AS ODN may be administered up to 24 hours, up to 36 hours, up to 48 hours or up to 72 hours before surgery. In particular aspects, the pharmaceutical composition may be administered about 48 to about 72 hours before surgery. Typically, in such circumstances, the administration is by intravenous bolus.

As discussed, in patients suffering from certain cancers including, but not limited to, glioma, astrocytoma, breast cancer, head and neck squamous cell cancer, papillary renal cell carcinoma Type II, lung cancer, pancreatic cancer, gall bladder cancer, rectal cancer, classical Hodgkin's lymphoma, ovarian cancer, and colorectal cancer, M2 cells cause the tumor environment to be immunomodulatory towards Type 2 immunity, which suppresses Type 1 immunity. M2 cells, thereby, attenuate induction of therapeutic Treatment of such cancer patients with the nucleic acid of the invention would eliminate or modify the M2 cells, which would have direct inhibitory consequences for tumor growth as well as and promote immunity response. Furthermore, it would be preferential in certain embodiments to treat such patients with a combination of the nucleic acid and a vaccination to promote immunity. Accordingly, in certain embodiments, it is advantageous to provide a method of treatment, wherein the nucleic acid is provided, alone, or in combination with a further medicament, for selectively targeting M2 cells. Through the elimination of these cells, tumor production and promotion is mitigated and reduced, and immune modulating factors are further modified.

Therefore, in certain embodiments is provided a method for enhancing immune response in a patient suffering from cancer by targeting expression of IGF-1R in M2 cells comprising administering to a patient suffering from the cancer an effective amount of the pharmaceutical composition.

Combination Therapy

The reduction in M2 cells may be accomplished along with stimulation of an anti-tumor immune response, referred to herein as a vaccination therapy. In certain embodiments, the vaccination therapy comprises placing tumor cells cultured in vitro or ex vivo in a medium supplemented with a pro-apoptotic agent for a period of time, such as, for example, 3 to 48 hours, washing the tumor cells with buffer to eliminate any trace of the pro-apoptotic agent, and subsequently transferring the cells to a diffusion chamber, which is then implanted into the subject (see, for example, U.S. Pat. No. 6,541,036, which is incorporated herein by reference in its entirety). In certain embodiments, the diffusion chamber contains tumor cells which are derived from the same type of tumor to which regression is induced by the pharmaceutical composition of the present invention. In other embodiments, the tumor cells placed in the diffusion chamber are of a different type than the tumor to which regression is induced.

In certain embodiments, the diffusion chamber is implanted into a subject prior to systemically administering the pharmaceutical composition of the present invention to the subject. In other embodiments, the diffusion chamber is implanted into a subject subsequent to systemically administering the pharmaceutical composition. In yet other embodiments, the diffusion chamber implanted into a subject also contains the pharmaceutical composition. In some aspects, a diffusion chamber containing the pharmaceutical composition and autologous tumor cells, treated in vitro or ex vivo as described above, is implanted into a subject. In other aspects, a diffusion chamber containing the pharmaceutical composition and tumor cells from a subject, treated in vitro or ex vivo as described above, is implanted to the subject. In certain embodiments, implanting the diffusion chamber into a subject further reduces the number of M2 cells in the subject in comparison to a subject who is administered the pharmaceutical composition alone.

In some embodiments, the chamber is implanted into the subject's abdomen. In certain embodiments, the diffusion chamber is surgically implanted into the rectus sheath of a subject for a therapeutically effective time.

In some aspects, the pharmaceutical composition is administered to the subject subsequent to the administration of the vaccination therapy. In certain aspects, the pharmaceutical composition is administered to the subject at least about 1 hour, at least about 2 hours, at least about 3 hours, at least about 6 hours, at least about 12 hours, at least about 24 hours, at least about 48 hours, at least about 72 hours, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 3 weeks, at least about 4 weeks, at least about 5 weeks, or at least about 6 weeks subsequent to administration of the pharmaceutical composition. In certain embodiments, the vaccination therapy is administered to the subject at least about 48 hours subsequent to the administration of the vaccination therapy.

In certain aspects, the vaccination therapy is administered to the subject subsequent to the administration of the pharmaceutical composition. In certain embodiments, the vaccination therapy is administered to the subject at least about 1 hour, at least about 2 hours, at least about 3 hours, at least about 6 hours, at least about 12 hours, at least about 24 hours, at least about 48 hours, at least about 72 hours, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 3 weeks, at least about 4 weeks, at least about 5 weeks, or at least about 6 weeks subsequent to administration of the pharmaceutical composition. In certain embodiments, the vaccination therapy is administered to the subject at least about 48 hours subsequent to the administration of the pharmaceutical composition.

In some embodiments, the method for enhancing immune response comprises administering a second pharmaceutical composition subsequent to the vaccination therapy. In certain embodiments, the second pharmaceutical composition is administered to the subject at least about 1 hour, at least about 2 hours, at least about 3 hours, at least about 6 hours, at least about 12 hours, at least about 24 hours, at least about 48 hours, at least about 72 hours, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 3 weeks, at least about 4 weeks, at least about 5 weeks, or at least about 6 weeks subsequent to administration of the vaccination therapy.

In other embodiments, the vaccination therapy is administered to the subject subsequent to the administration of the second pharmaceutical composition. In certain embodiments, the vaccination therapy is administered to the subject at least about 1 hour, at least about 2 hours, at least about 3 hours, at least about 6 hours, at least about 12 hours, at least about 24 hours, at least about 48 hours, at least about 72 hours, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 3 weeks, at least about 4 weeks, at least about 5 weeks, or at least about 6 weeks subsequent to administration of the second pharmaceutical composition.

In certain embodiments, the pharmaceutical composition and the second pharmaceutical composition are the same. In other embodiments, the pharmaceutical composition and the second pharmaceutical composition are different.

Typically, the tumor cells are irradiated prior to implantation; for example, the cells may be treated with gamma irradiation at an amount of about 1 Gy, about 2 Gy, about 4 Gy, about 5 Gy, about 6 Gy, about 10 Gy, or up to 15 Gy. In certain embodiments, the cells may be irradiated at least once, at least twice, at least three times, at least four times, or at least five times.

In certain embodiments is provided a method for preventing or delaying cancer in a subject by targeting expression of IGF-1R in M2 cells comprising administering to with the subject an effective amount of the pharmaceutical composition. In some embodiments, the subject is an animal. In other embodiments, the subject is a human. In certain aspects, the human is predisposed to the cancer by virtue of being continuously exposed to one or more carcinogens that increase the risk of that cancer. In certain aspects, these carcinogens include, but are not limited to cigarette smoke, tobacco, and asbestos. In other aspects, the human is genetically predisposed to the cancer.

In certain embodiments, are provided methods for treating, preventing, or delaying diseases including, but not limited to, Alzheimer's disease, inflammatory bowel disease, insulin resistance in type 2 diabetes, and psoriasis in a subject by targeting expression of IGF-1R in M2 cells comprising administering to with the subject an effective amount of the pharmaceutical composition.

EXAMPLES

Example 1: Immunohistochemistry for IGF-1R in Glioblastoma Multiforme Specimens

Original magnification 200× (panels A, B, C, D), 400× (panel E). In order to evaluate the relevance of IGF-1R expression in glioblastoma multiforme, 18 consecutive glioblastoma cases were stained with anti-IGF-1R alpha (Santa Cruz Biotechnology, Santa Cruz, Calif.). immunohistochemistry for IGF-1R alpha was performed on routine formalin fixed paraffin embedded sections (FIG. 5). Steam heat-induced epitope retrieval of the sections enhanced with Target Retrieval Solution (#1699, Dako Corporation, Carpinteria, Calif.) was followed by automated immunostaining (Dako autostainer, model # LV-1, Dako Corporation) or IGF-1R alpha (Santa Cruz Biotechnology, Santa Cruz, Calif.) at a dilution of 1:500. Detection as achieved with a rabbit secondary antibody MACH 3 Rabbit HRP Kit, Biocare Medical) and AB solution (3,3'-diaminobenzidine in chromagen solution, Dako Corporation). All tumors demonstrated IGF-1R immunoreactivity.

Example 2: Drug Substance, Formulation and Stability of NOBEL

As described above, NOBEL is an 18-mer oligodeoxynucleotide has a phosphorothioate backbone and is as an antisense directed against the insulin-like growth factor type 1 receptor (IGF-1R AS ODN) starting with six nucleotides downstream from the initiating methionine codon. The molecular weight for the free acid is 5708.71 Daltons. The molecular weight for the sodium salt is 6082.40 Daltons. The sequence of NOBEL, derived as the complimentary sequence of the IGF-1R gene at the 5' end, is: 5'-TCCTC-CGGAGCCAGACTT-3'.

NOBEL is manufactured by solid phase organic synthesis using well-established methodology in a synthesizer equipped with a closed chemical column reactor using flow-through technology. Each synthesis cycle sequence on the solid support consists of multiple steps, which are carried out sequentially until the full-length oligonucleotide is established. The drug substance, which is a lyophilized powder, is packaged in a HDPE container with screw cap and then vacuum-heat-sealed inside a 5-mL Mylar pouch for storage at −80° C.

The drug product consists of the new drug substance dissolved in saline until a 100 mg/mL solution is achieved. The resulting solution is sterile filtered through a 0.22 m membrane filter. 1 mL aliquots are filled into USP Type 1 glass vials and sealed with an appropriate rubber stopper and aluminum cap prior to storage at −80° C. This formulation has proven to be stable over nine years (last test date) in two independent formulations when reconstituted in sterile normal saline (FIG. 6).

Example 3: Preclinical Assessment of Toxicity in Mice

The purpose of this study was to evaluate the toxicity of the test article, NOBEL, when administered as a single dose via intravenous injection to mice; after dosing, animals were observed postdose for approximately 48 hours (Day 3 interim sacrifice) or 14 days (Day 15 terminal sacrifice) to assess the reversibility, persistence, or delayed occurrence of effects. This study was conducted according to Good Laboratory Practice and compliant with standards established by the Food and Drug Administration. Male and female Crl: CD1(ICR) mice were assigned to groups, and doses were administered as indicated in the following table. Animals were dosed once at a volume of 100 µL via intravenous injection in a tail vein with vehicle/diluent [0.9% Sodium Chloride for Injection, USP (sterile saline)] or NOBEL (provided as 100 mg/mL in sterile saline) (see Table 2).

TABLE 2

NOBEL Dosing Regimen in Mice

| Group[a] | No. of Animals[b] | | Dose Level (mg/mouse) | Dose Concentration (mg/mL) |
| --- | --- | --- | --- | --- |
| | Male | Female | | |
| 1 (Control) | 15 | 15 | 0 | 0 |
| 2 (Low) | 15 | 15 | 0.01 | 0.01 |
| 3 (High) | 15 | 15 | 0.04 | 0.04 |

[a]Group 1 received vehicle/diluent (sterile saline) only.
[b]Animals designated for interim sacrifice (10 animals/sex/group) were sacrificed approximately 48 hours after dose administration. Animals designated for terminal sacrifice (five animals/sex/group) were sacrificed 14 days after dose administration.

Assessment of toxicity was based on mortality, clinical observations, body weight, food consumption, and clinical and anatomic pathology. All animals survived to their scheduled necropsy on Day 3 or 15 of the dosing phase. No test article-related clinical observations or changes in food consumption occurred. No statistically significant effects on body weight were observed. However, slightly lower body weight (93.8% of controls) occurred by Day 15 of the dosing phase in males given 0.04 mg/mouse. This trend was observed as early as Day 8 of the dosing phase in these males and was considered test article-related but not adverse because no clinical changes in body condition or hydration status occurred. No test article-related body weight effects were observed in males given 0.01 mg/mouse or in females.

NOBEL administration had no effect on clinical pathology test results. Among interim sacrifice animals, lung weights in females given 0.01 mg/mouse, testis weights in males given 0.01 or 0.04 mg/mouse, and thymic weights in males given 0.04 mg/mouse were higher. Among terminal sacrifice animals, brain weights in males given 0.01 or 0.04 mg/mouse and lung weights in females given 0.04 mg/mouse were higher. None of these organ weight changes had any correlative microscopic observations. Test article dependency was unknown. Regardless, none of the weight differences could be considered adverse. None of the macroscopic or microscopic observations were considered test article-related.

In conclusion, NOBEL given as a single intravenous bolus injection to male and female mice at a dose level of 0, 0.01, or 0.04 mg/mouse was well tolerated and not associated with any clinical observations, changes in food consumption, clinical pathology changes, or macroscopic or microscopic changes. Minor, test article-related changes in body weight and increases in brain and lung weights of uncertain relationship to the test article were not considered adverse. Therefore, the no observed adverse effect level is considered to be 0.04 mg/mouse.

Example 4: Selective Knockdown of M2 (CD163+) Macrophages

NOBEL selectively knocks down CD163+ cells in both humans and mice. Serum derived from patients with malignant gliomas as well as a variety of other cancers including, but not limited to, astrocytoma, breast cancer, head and neck squamous cell cancer, papillary renal cell carcinoma Type II, lung cancer, pancreatic cancer, gall bladder cancer, rectal cancer, classical Hodgkin's lymphoma, ovarian cancer, and colorectal cancer will differentiate monocytes into the CD163+ phenotype that take up NOBEL at low micromolar concentrations resulting in knockdown of this phenotype.

Figures 8A, 8B:
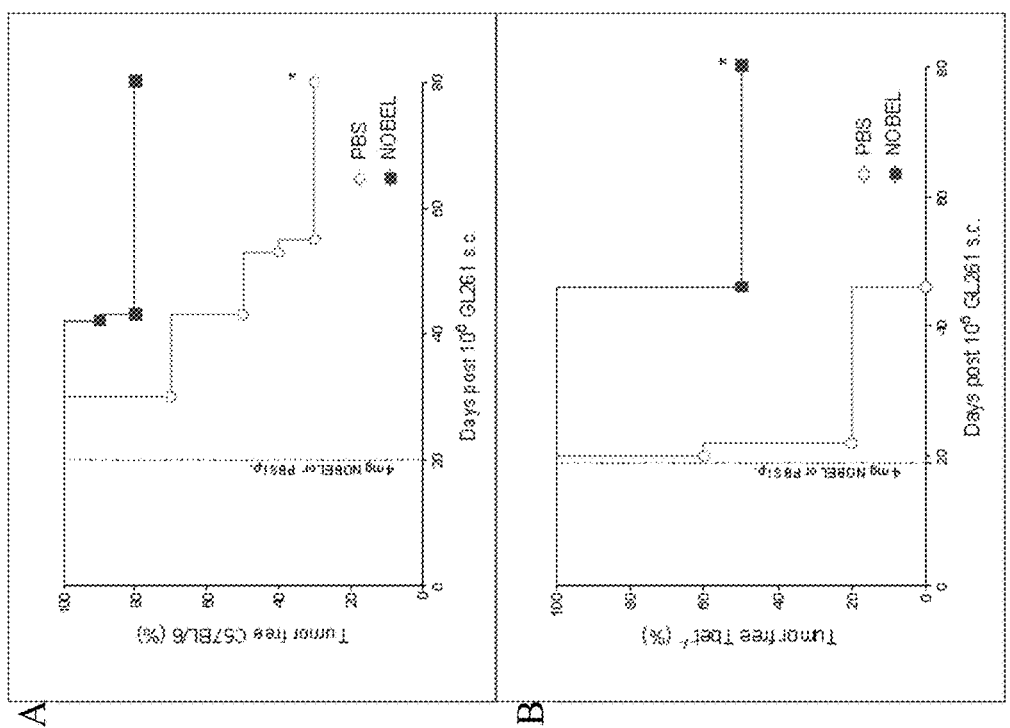
FIG. 8 (FIG. 8A and FIG. 8B) shows that the administration of NOBEL (SEQ ID NO: 1) alone prior to tumor development is effective at delaying the onset of GL261 cell outgrowth. 20 and 50% of C57 and Tbet knockout mice, respectively, develop tumors after i.p. NOBEL, compared with 60 and 100% of C57 and Tbet knockout animals that received vehicle i.p. (PBS), respectively. Significance was assessed using the log rank test (*=p<0.05).

In a C57B/6 mouse model intraperitoneal antisense administration twenty days after flank tumor inoculation resulted in knockdown of tumor-induced CD163 cells for at least 14 days (see FIG. 7). GL261 cells were implanted in the flanks of C57BL/6 and Tbet−/− mice, and then at approximately 20 days later animals received either PBS or 4 mg NOBEL alone as a systemic, intraperitoneal injection (FIG. 8). Tbet−/− mice that are unable to mount anti-tumor type 1 immunity and reject GL261 tumors were included to differentiate between effects on the balance of type 1 and type 2 immunity versus knockdown of M2 cells. In both cases, the administration of a single dose of NOBEL alone just prior to the detection of palpable tumors delayed the formation of tumors for significant periods. Long term survival was also promoted with 80% of C57 mice and 50% of Tbet knockout mice failing to grow tumors (FIG. 8). Mixing NOBEL with GL261 cells has little effect on tumor growth in the absence of an intact immune system (Morin- Brureau et al, *Cancer Immunol. Immunother.*, 64:447-457 (2015)) and a mix of NOBEL with GL261 cells at implantation in Tbet mice also does not interfere with tumor growth. The important conclusion here is that the effects of IGF-R1 AS ODN on GL261 at the induction of tumor immunity are distinct from those acting upon tumor growth some time later. One requires the co-administration of tumor as antigen and NOBEL as immune stimulant while the other has systemic effects that are independent of the response to antigen. The knockdown of M2 cells and possibly other cells involved in promoting tumor growth is evidently sufficient to prevent tumor growth even when the recipient animal is unable to mount a therapeutic type 1 response. The data suggests that the loss of M2 cells from the tumor microenvironment results in failure of the tumor cells to thrive.

Example 5: Administration of IGR-1R AS ODN to Glioma Patients

From the current studies we determined suitable doses to administer in recurrent glioma cohorts glioma in the following dosing schedules: 0.025 g/kg, 0.05 g/kg, 0.1 g/kg, 0.15 g/kg, and 0.2 g/kg.

Patients receiving one of the above doses are patients having recurrent glioma and who receive escalating pre-operative intravenous bolus infusion of the IGF-1R 48 to 72 hours before surgery. A second bolus infusion may be further administered depending on quantitation of the M2 cell population. This dosing schedule also works for other cancers including, but not limited to, astrocytoma, breast cancer, head and neck squamous cell cancer, papillary renal cell carcinoma Type II, lung cancer, pancreatic cancer, gall bladder cancer, rectal cancer, classical Hodgkin's lymphoma, ovarian cancer, and colorectal cancer Example 6: Different IGF-1R AS ODN Sequences Different IGF-1R antisense sequences are bioactive in some or all of the multi-modality effects of the NOBEL sequence (5'-TCCTCCGGAGCCAGACTT-3' (SEQ ID NO: 1)). The 18-mer NOBEL sequence has both IGF-1R receptor downregulation activity as well as TLR agonist activity, and further experimentation in mice suggest that both activities are necessary for in vivo anti-tumor immune activity. While the AS ODN molecule has anti-tumor activity, the complimentary sense sequence does not, despite also having a CpG motif. The entire open reading frame of the IGF-1R exon (4104 base pairs) was surveyed and ten additional CpG motifs, including IDT1220, were identified, (SEQ ID NOs: 2-11) (Table 3). In addition, several additional IGF-1R antisense sequences (SEQ ID Nos: 12-14) that did not contain CpG motifs were also identified (Table 3).

TABLE 3

Potential additional downstream sequences for IGF-1R AS ODN Formulation

| Sequences with ACGA Motif | Corresponds to IGF-1R Codons | SEQ ID NO: |
| --- | --- | --- |
| 5'-TCCTCCGGAGCCAGACTT-3' | 2-7 | 1 |
| 5'-TTCTCCACTCGTCGGCC-3' | 26-32 | 2 |
| 5'-ACAGGCCGTGTCGTTGTC-3' | 242-248 | 3 |
| 5'-GCACTCGCCGTCGTGGAT-3' | 297-303 | 4 |

TABLE 3 -continued

Potential additional downstream sequences for IGF-1R AS ODN Formulation

| Sequences with ACGA Motif | Corresponds to IGF-1R Codons | SEQ ID NO: |
| --- | --- | --- |
| 5'-CGGATATGGTCGTTCTCC-3' | 589-595 | 5 |
| 5'- TCTCAGCCTCGTGGTTGC-3' | 806-812 | 6 |
| 5'-TTGCGGCCTCGTTCACTG-3' | 1,033-1,039 | 7 |
| 5'-AAGCTTCGTTGAGAAACT-3' | 1,042-1,048 | 8 |
| 5'-GGACTTGCTCGTTGGACA-3' | 1,215-1,221 | 9 |
| 5'-GGCTGTCTCTCGTCGAAG-3' | 1,339-1,345 | 10 |
| 5'-CAGATTTCTCCACTCGTCGG-3' | 27-34 | 11 |
| 5'-CCGGAGCCAGACTTCAT-3' | 1-6 | 12 |
| 5'-CTGCTCCTCCTCTAGGATGA-3' | 407-413 | 13 |
| 5'-CCCTCCTCCGGAGCC-3' | 4-8 | 14 |

Example 7: Activation of Toll-Like Receptor 9 by NOBEL

Figure 9:
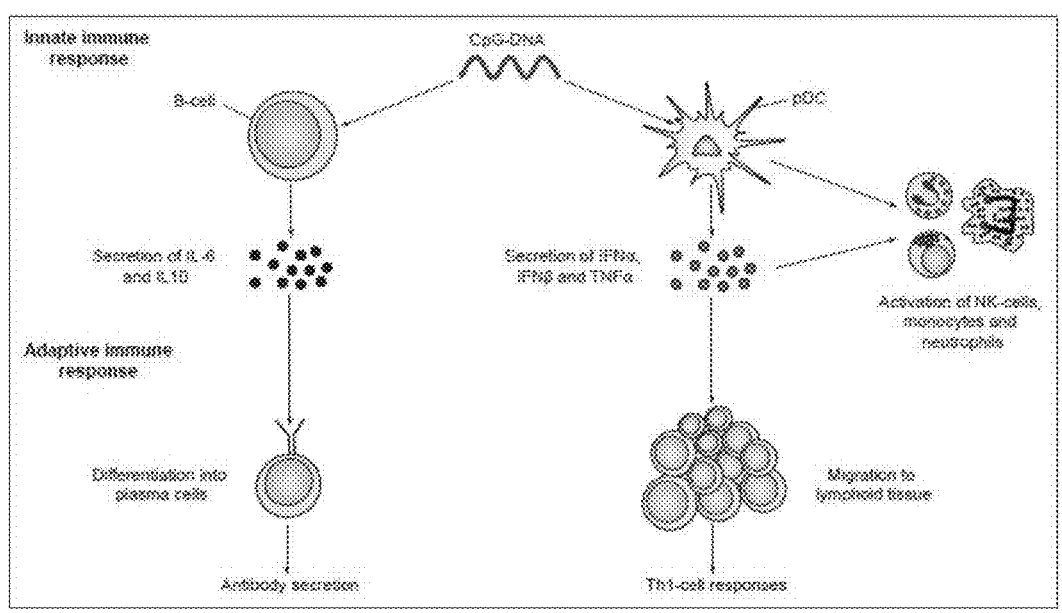
FIG. 9 shows that Cytosine-phosphorothioate-guanosine-DNA activates TLR9 expressed on B-cells and plasmacytoid dendritic cells (DCs).

The front-line defense in the immunologic response to invading pathogens involves interactions between pathogen structures and an array of receptors including toll-like receptors (TLRs) that activate the innate immune system. This arm of the immune system recognizes generic classes of molecules produced by a variety of pathogens including bacteria, viruses, fungi, and parasites, all of which are essential for the survival of the invading pathogen. These pathogen-associated molecular patterns, or PAMPS, are recognized by pathogen related receptors, or PRRs, expressed in immune effector cells, notably dendritic cells. These PRRs were named toll-like receptors due to homology to the toll protein characterized in drosophila originally characterized by Nusslein-Volhard in 1991. Stein et al., *Cell* 65:725-35 (1991). The activating effects of TLRs, are important in directing the type of ensuing adaptive immune response. There are currently 10 known human TLRs and TLR9 is of particular interest. TLR9 binds fragments of DNA that include an unmethylated cytosine-guanosine sequence unique to bacteria and viruses. The human CpG dinucleotide is invariably methylated, rendering autologous human DNA tolerogenic if exposed to the immune system. The unmethylated CpG motif, particularly when nested in a favorable flanking nucleotide hexamer sequence, elicits a powerful innate immune response (FIG. 9). When compared to antisense gene translation silencing drug levels, responses are seen at 1000-fold lower concentrations.

Figure 10:
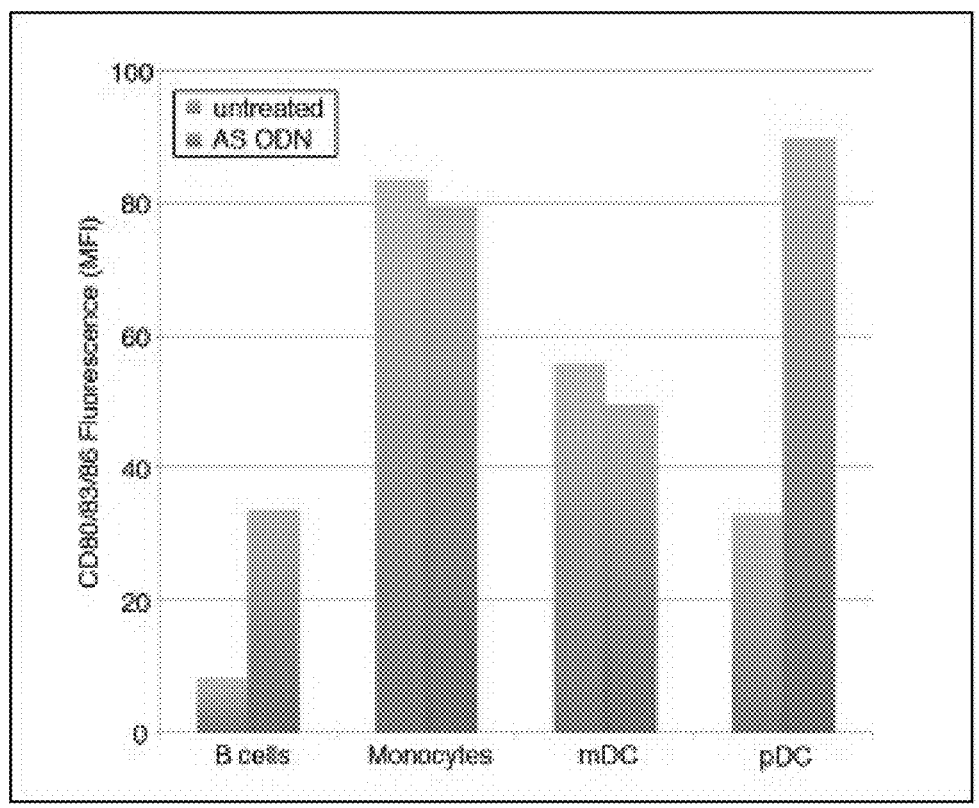
FIG. 10 shows that antigen-presenting cells take up AS ODN and express increased costimulatory molecules and express levels of CD80/83/86 in PBMC before and after AS ODN treatment; mDC, myeloid dendritic cell; pDC, plasmacytoid dendritic cell.

The NOBEL sequence was found to activate both plasmacytoid DCs and B cells. In vitro AS ODN uptake experiments with PBMC were performed and assayed for activation of immune cell subsets. The highest uptake of AS ODN occurred in endocytic antigen presenting cells: monocytes, dendritic cells (DC), and B cells while negligible uptake was observed in T cells or NK cells. AS ODN-treated plasmacytoid dendritic cells (pDC), and B cells, increased expression of costimulatory molecules important in T cell activation (CD80, 83, and 86). Despite observing the highest levels of AS ODN uptake, expression levels of CD80, 83, and 86 were unaltered in monocytes and myeloid dendritic cells (FIG. 10).

Example 8: Dendritic Cell Activation and Maturation after NOBEL Treatment

Figure 11:
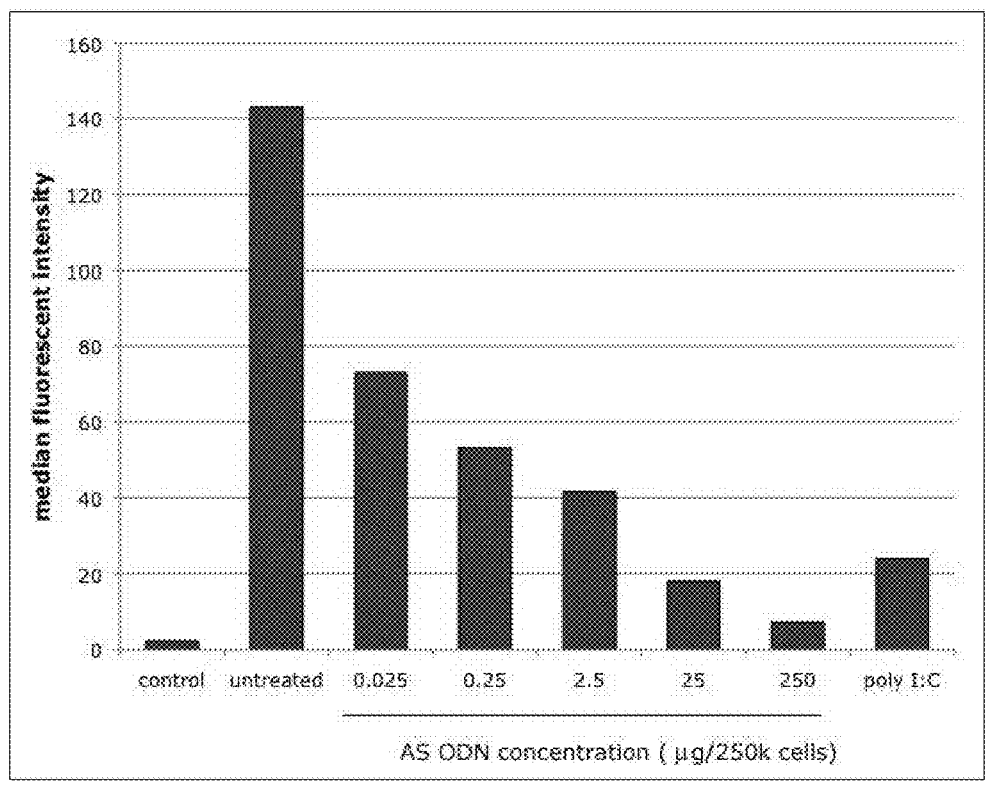
FIG. 11 shows that NOBEL (SEQ ID NO: 1) activates monocyte-derived dendritic cells (DC) as determined by decreased median fluorescence intensity. Immature DCs engulfed large amounts of fluorescent protein resulting in higher fluorescent intensities (depicted by larger bars). Mature DCs (activated) down-regulate endocytosis and as a result, take up less fluorescent protein and possess low fluorescent intensities (depicted by smaller bars). Treatment of monocyte-derived dendritic cells with IGF-1R AS ODN reveals a striking dose-dependent maturation response.

Treatment of monocyte-derived dendritic cells with NOBEL reveals a striking dose-dependent maturation response (FIG. 11). Immature DC were obtained by culturing CD14+ PBMC in rGM-CSF and rIL-4 for 4 days. Immature DC were treated with NOBEL for 36 hours. Poly I:C was used as a positive control for DC maturation. Treated-DC were harvested, incubated with a fluorescent protein, and analyzed with a flow cytometer. High endocytic capacity is a hallmark of immature DC which is rapidly and dramatically reduced upon maturation signals. NOBEL treatment decreased endocytic capacity in DC in a dose-dependent manner.

Example 9: Optimal AS ODN Sequence

Figure 13B:
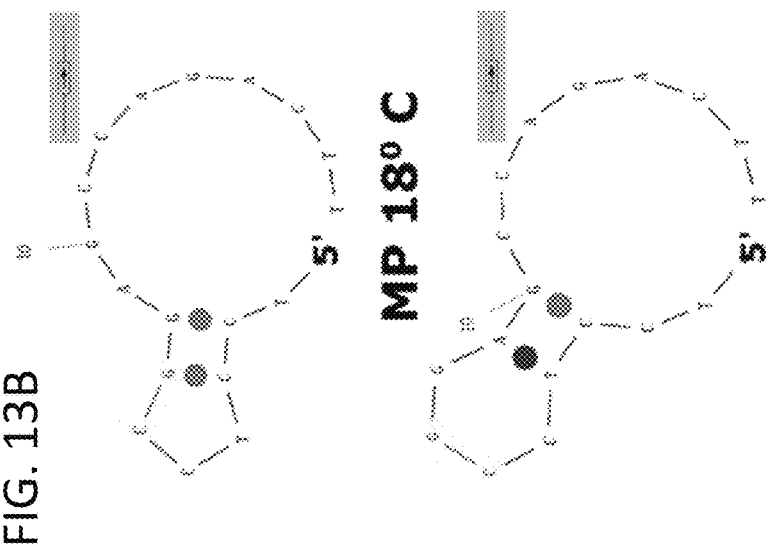
FIG. 13B. the NOBEL (SEQ ID NO: 1) sequence at 37° C. has no hairpin loop (shaded insets) at the 5' side of a CpG motif for two alternate secondary structures with MP at 18° C., allowing for greater likelihood of targeted base pairing and also CpG.
Figure 13A:
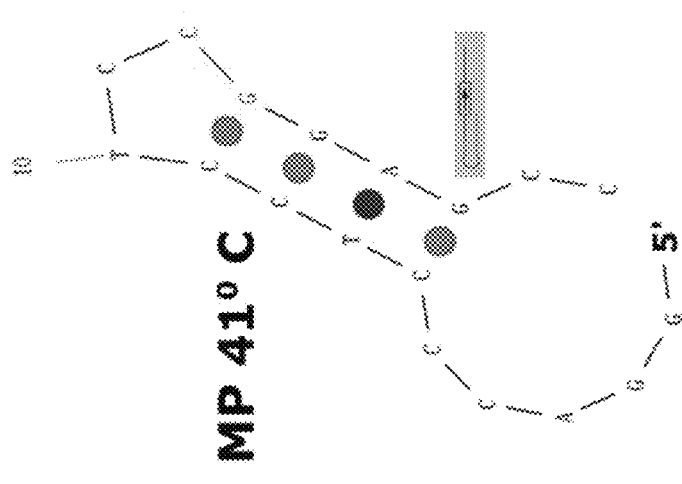
FIG. 13 shows that FIG. 13A. the DWA sequence at 37° C. maintains a hairpin loop secondary structure (shaded inset) at the 5' side possibly affecting base-pairing to targeted mRNA sequence.

As a guideline to screening more IGF-1R AS ODN sequences, sequences at the 5' end of a targeted mRNA transcript have the greatest likelihood of binding to an mRNA sequence according to Watson-Crick base-pairing rules. This biological activity is attributable to the favorable sequence which yields a higher probability of a linear molecule at body temperature unlike the DWA sequence which is more likely to form a stable 5' hairpin loop at body temperature (FIG. 13). As noted above, the biological activity is attributable to include accessibility to the targeted mRNA sequence as well as the unmethylated CpG dinucleotide which should be accessible from the 5' end of the molecule and ideally a linear molecule at body temperature. Despite these guidelines the DWA sequence, while having no capability of IGF-1R downregulation, appeared better at DC maturation (FIG. 12). The biological activities of the different IGF-1R AS ODNs are summarized in Table 4 below.

Figures 14A, 14B:
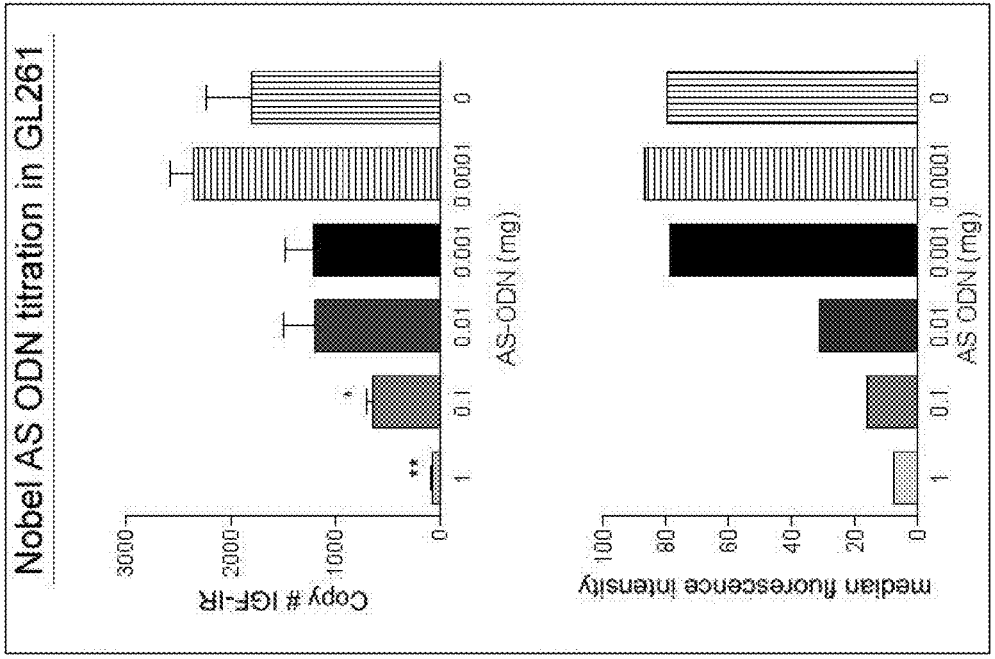
FIG. 14A. Effects of NOBEL titration on IGF-1R expression in GL261 cells. Copy number IGF-1R versus final mg per well in microtiter plate (or mg per 20 k cells). Cells were plated. Significance was determined with ANOVA analysis (*=P<0.05; **=P<0.001).
FIG. 14B. Cells were harvested, stained with an antibody specific for mouse IGF-1R, and analyzed with a flow cytometer. Median fluorescence intensity is plotted versus final AS ODN concentration (mg per 20 k cells). IGF-1R expression was significantly reduced in GL261 cells treated with 1 mg Nobel AS ODN per well (P<0.001), as well as in cells treated with 0.1 mg Nobel AS ODN per well (P<0.05).
Figure 15:
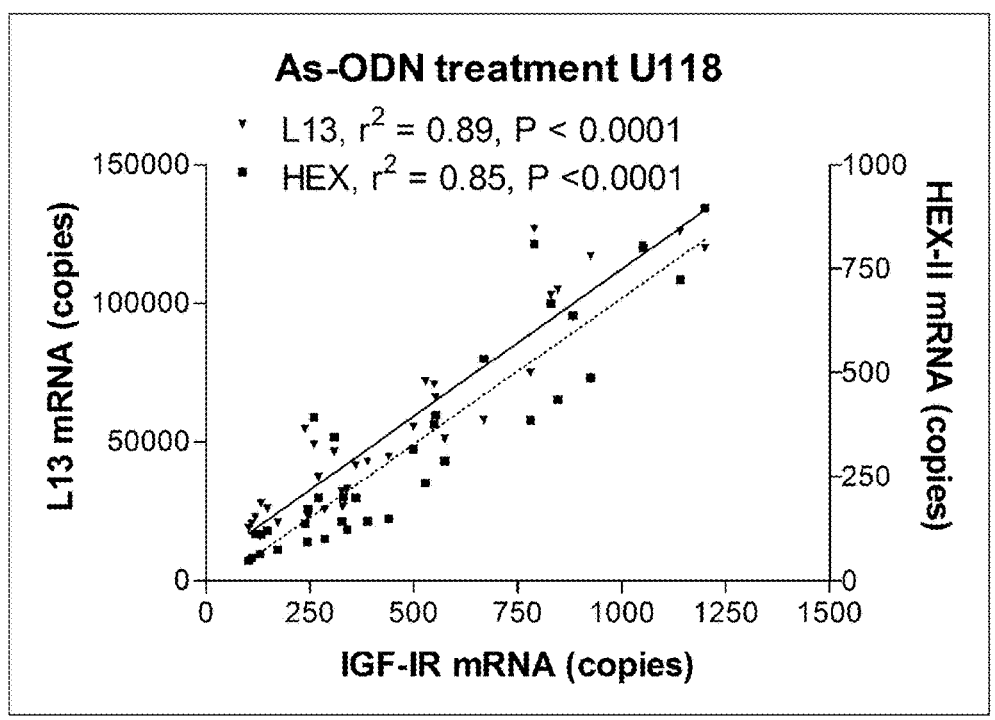
FIG. 15 shows the results of quantitative RT-PCR to assess downstream downregulation of hexokinase isotype 2 mRNA. The expression of L13, IGF-1R and HexII genes in NOBEL (SEQ ID NO: 1)-treated cells of the human glioma line U118 is linearly correlated. Specific mRNA copy numbers for the housekeeping gene L13 (▼) and hexokinase 2 [HEX](■) plotted against IGF-1R copy numbers detected in individual cultures treated with NOBEL at different concentrations are shown. The solid line represents the best-fit linear regression line between L13 and IGF-1R and the dotted line represents the best-fit linear regression line between Hex-II and IGF-1R with $r^2$ representing the degree of linearity (out of 1.0) and P the significance of the slope.

Example 10: Downregulation of IGF-1R: Summary of Biospecificity and Bioactivity of NOBEL Two assays were designed to assess the biospecificity of the AS ODN sequence:

a. Quantitative RT-PCR to assess downregulation of IGF-1R mRNA—this assay was designed to confirm Watson-Crick base-pairing between cellular IGF-1R transcribed mRNA and the AS ODN. GL261 mouse cells were obtained from NCI-Frederick DTP, DCTD Tumor Bank Repository (Frederick, Md.) and in RPMI supplemented with 10% FBS, 4 Mm L-glutamine (Fisher), 50 µg/mL gentamicin (GIBCO) and 0.05 Mm 2-ME (Sigma). As shown in FIG. 14, IGF-1R expression was significantly reduced in GL261 cells treated with 1 mg Nobel AS-ODN per well (P<0.001), as well as in cells treated with 0.1 mg Nobel AS ODN per well (P<0.05).

b. Quantitative RT-PCR to assess downstream downregulation of hexokinase isotype 2 mRNA—IGF-1 induces hexokinase RNA expression in cancer cells. It was predicted that reduced IGF-1R activation by IGF-1 as a consequence of IGF-1R downregulation by AS-ODN treatment should lead to a similar reduction in hexokinase expression. As shown in FIG. 15, this is the case with the reduction in IGF-1R mRNA being highly correlated with downregulation of hexokinase II. A 90% reduction in IGF-1R copy number corresponded to a 90% reduction in hexokinase II copy number. A downregulation of housekeeping genes was also expected, in this case seen as a 75% decrease in L13, since inhibition of the IGF-1R slows growth kinetics and metabolism in vitro.

Figure 16:
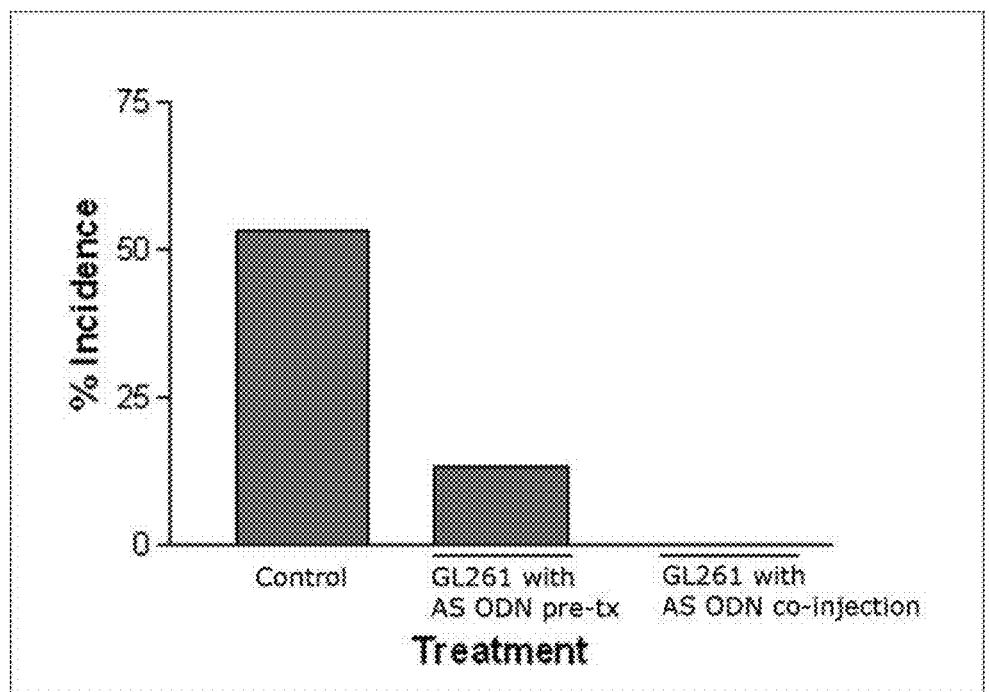
FIG. 16 shows the cumulative tumor growth in C57/B6 mice injected with $10^6$ GL261 cells two weeks post AS ODN treatment. All mice in the AS ODN group were injected in the flank once with $10^6$ NOBEL (SEQ ID NO: 1)-treated GL261 (overnight AS ODN treatment, 20 mg/$5 \times 10^6$ GL261) and challenged two weeks post treatment in the opposite flank with WT GL261; mice in AS ODN/GL261 mix group were injected in the flank once with NOBEL (20 mg/$5 \times 10^6$ GL261) mixed with untreated GL261 cells immediately prior to injection and challenged two weeks post treatment in the opposite flank with WT GL261. Tumors developed from the post treatment challenge (WT GL261).
Figure 17:
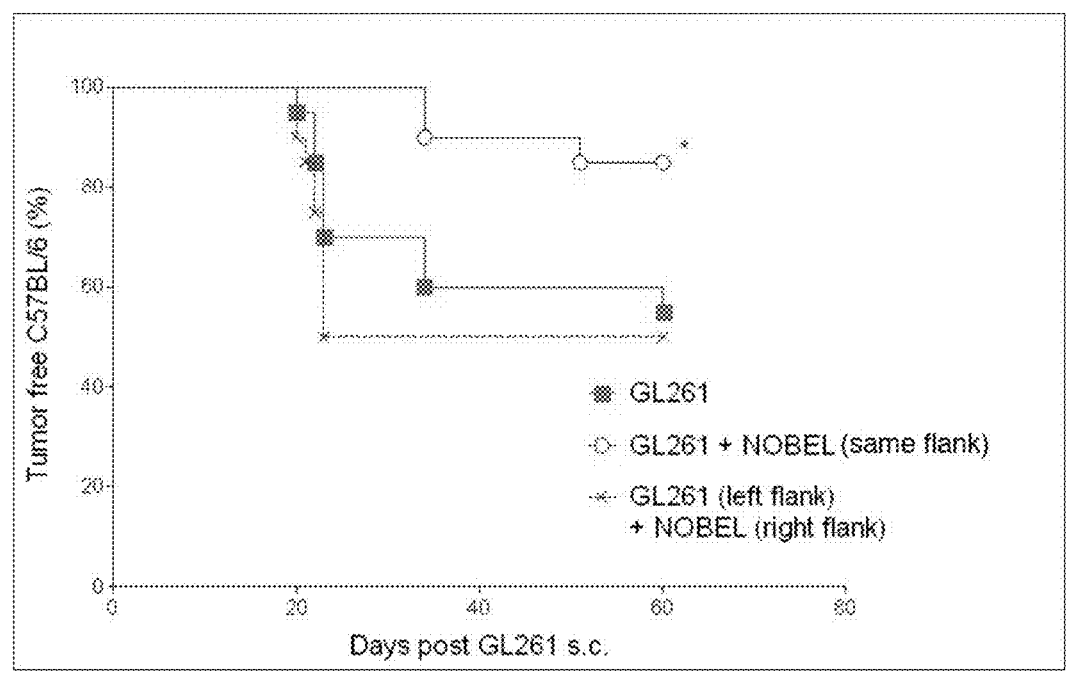
FIG. 17 shows that the combination of GL261 cells and NOBEL (SEQ ID NO: 1) at site of administration prevents tumor formation in a subcutaneous model.

Example 11: Bioactivity of the IGF-1R AS ODN: Mouse Flank Model to Assess Vaccine Capability of the NOBEL Sequence Against Tumor Challenge C57/BL6 mice were obtained from Jackson Laboratory (Bar Harbor, Me.) and Taconic Farms, Inc. and used between 8 and 10 weeks of age. Mice were anesthetized in a chamber containing isoflurane and injected in the flank with $10^6$ GL261 in 100 µL PBS using a 1 mL BD Falcon syringe and 21 G BD needle (Fisher). AS ODN GL261 cell preparations were injected in the left flank whereas wild-type GL261 cells were injected in the right flank two weeks later. Mice were checked at least twice a week for tumor development. It should be noted for these studies that GL261 cells are well known to be immunostimulatory when placed in the flanks of congenic mice such that roughly 50% of such animals are expected to develop anti-tumor cell immunity in the absence of intervention. As seen in FIG. 16, pretreatment with AS-ODN treated GL261 cells reduced WT GL261 tumor growth from 53% in control mice to 13%, whereas pretreatment with a GL261 AS ODN mixture (4 mg NOBEL per $10^6$ GL261) reduced WT GL261 tumor take to 0%. Of interest, the efficacy of the vaccine was lost when GL261 and NOBEL were injected in opposite flanks of the mouse (FIG. 17). These data suggest that although AS ODN-treated GL261 and the antisense molecule contribute to an anti-tumor response, the most effective vaccine involves simultaneous injection of autologous tumor cells with the IGF-1R AS ODN. Also of interest, the NOBEL sense sequence, which is palindromic around the CpG motif, is not effective at stimulation of anti-tumor immunity suggesting that the biological effectiveness of the CpG motif is related to the bioactivity of the IGF-1R AS ODN beyond the CpG motif alone.

TABLE 4

Summary of Biological Activities of Different IGF-1R AS ODNs.

| SEQ. | Formulation | IGF-1R Codons | CpG/APC activation | M2 Macrophage inhibition | IGF-1R Down-regulation | In vivo Vaccine capability | Radio-sensitizer |
|---|---|---|---|---|---|---|---|
| Nobel | Phosphorothioate | 2-7 | + | + | + | + | + |
| DWA | Phosphorothioate | 4-9 | ++ | + | -- | + | N/A |
| DWA | Locked nucleic acid | 4-9 | N/A | N/A | N/A | N/A | N/A |
| IDT1220 | Phosphorothioate | 407-413 | +++ | + | -- | N/A | N/A |
| Avanti-10 (BioPath Holdings) | p-ethoxy in neutral lipid carrier | 2-7 | N/A | + | N/A | N/A | N/A |

Example 12: NOBEL is Capable of Radiosensitization

Figure 18:
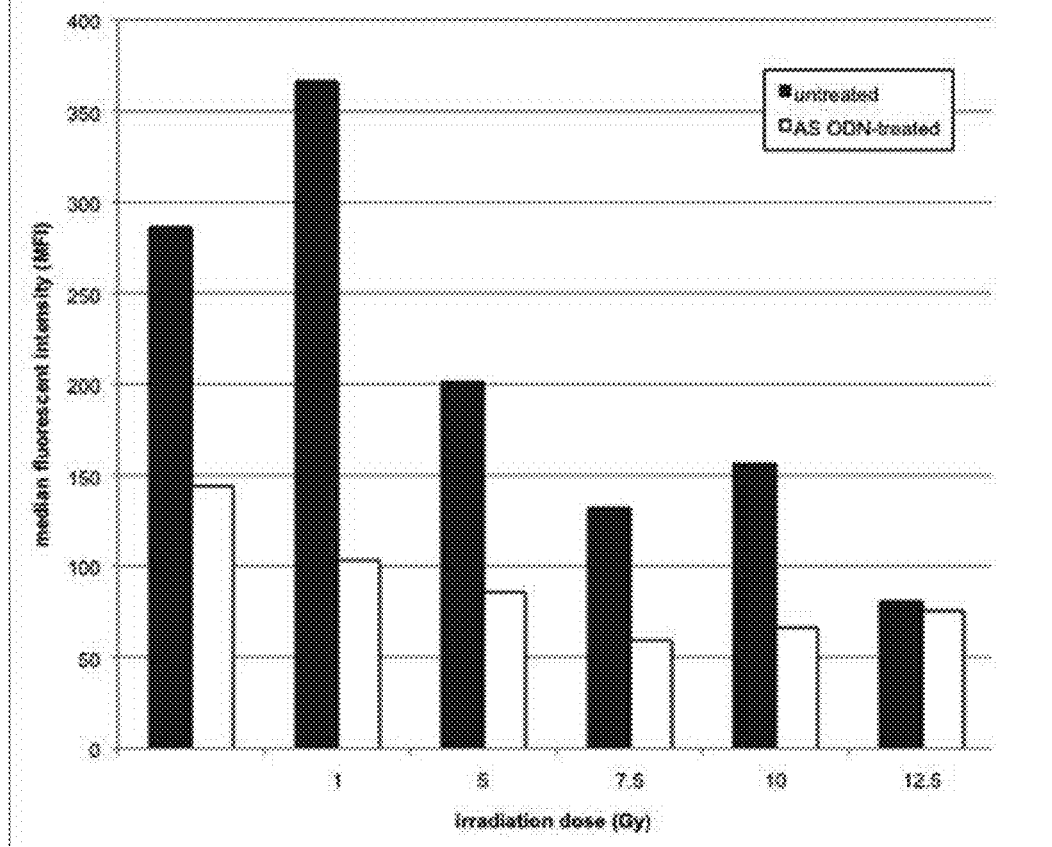
FIG. 18 shows that NOBEL (SEQ ID NO: 1) induces radiosensitization.

U118 cells were incubated in the presence or absence of NOBEL (4 mg/10$^7$ cells) for 24 hrs. Cells were harvested, irradiated, and returned to culture (with or without new NOBEL) in the presence of Click-iTedu reagent (10 µM final concentration). Following a 72 h incubation, cultures were developed according to the manufacturer's protocol. As shown in FIG. 18, Nobel AS ODN caused radiosensitivity of U118 human glioblastoma cells throughout a range of radiation doses from one to fifteen Gy with an isoeffect plateau beyond 5 Gy.

Example 13: Treatment of Astrocytoma

WHO Grade IV astrocytoma (glioblastoma) is a uniformly fatal primary intracranial malignancy with a median survival of 18 months. Twelve patients diagnosed with recurrent glioblastoma who were judged to be good surgical candidates were enrolled for treatment. All patients had failed standard therapy including surgery, temozolamide chemotherapy and conformal radiation therapy. A summary of enrolled patients and their disease courses is included in Table 5. All patients were treated with a 3 month course of subcutaneous enoxaparin at 40 mg/day.

The combination product consisting of autologous tumor cells removed at surgery then treated overnight with an IGF-1R As ODN prior to being added to semi-permeable chambers and irradiated. The vaccine product used the 18-mer IGF-1R AS ODN with the sequence 5'-TCCTCCG-GAGCCAGACTT-3', one frameshift downstream from the previous sequence; and, based on its immunostimulatory properties, addition of 2 µg of exogenous antisense to each chamber (C-v). The protocol was also amended to include a chamber containing PBS (C-p). Up to 10 chambers were implanted in the rectus sheath. Autologous tumor cell supernatants obtained during the plating phase of vaccine preparation and explanted chamber contents were flash-frozen for exploratory research objectives.

Study objectives included assessment of safety and radiographic responses including tumor relative cerebral blood volume (rCBV), apparent diffusion coefficient (ADC), and PET/CT with $^{18}$fluorodeoxyglucose dual-time image acquisition at 90 and 240 minutes. Exploratory objectives included serial assessments of peripheral blood mononuclear cells (PBMC) and chemokines/cytokines in sera, chamber fluids and cell cultures utilizing multiplexed analysis (Luminex).

Immunological Assessments

Plasma leukopheresis was performed one week before surgery for baseline assessment of immune parameters. Blood was also obtained post-operatively as previously described[1]. Sera and cell fractions were separated by centrifugation and cells were treated with red blood cell lysis buffer and white blood cells either quantified by flow cytometry or stored in DMSO at –80° C. as were serum samples. Flow cytometry was performed as previously described using an EasyCyte 8HT (Millipore) and fluorescently-conjugated mAb specific for human CD4, CD8, CD11b, CD14, CD16, CD20, CD45, CD56, CD80, CD83, and CD86 (all from BD Biosciences), and CD163 (R&D Systems). Post-collection analysis was performed with FlowJo software (Tree Star Inc, Ashland, Oreg.). Soluble cytokine factors were quantified using Luminex bead arrays (human cytokine/chemokine panels I, II, and III from Millipore). To assess T cell polyfunctionality prior to treatment and post operatively, PBMC from patients and normal controls were stimulated in vitro with phorbol 12-myristate 13-acetate (PMA) and ionomycin (Sigma Aldrich) and the cytokines and chemokines released into culture quantified by Luminex. Tumor tissue sections were assessed by immunohistochemistry for IGF-1R, CD163, CD14, CD206, CD204, CD3, CD4, and CD8. Where possible, Aperio quantification of immunopositive cells was used. Otherwise immunostaining was qualitatively assessed by an experienced neuropathologist (LEK) using an ordinal scale from 0 (no staining) to 6 (strong diffuse staining).

Levels of cytokines/chemokines in sera prior to and 2 days following surgery, the contents of the explanted chambers as well as supernatants from overnight tumor cell cultures (SN) were all quantitated by Luminex. Membranes from paired vaccine and control chambers were embedded in paraffin for immunohistopathologic examination.

TABLE 5

| Subject | Age | KPS | Interval between surgeries (weeks) | # chambers implanted | Original lymphocyte count (cells/mm2) | Lymphocyte count at enrollment (cells/mm2) | Previous treatments | IDH-1 mutation |
|---|---|---|---|---|---|---|---|---|
| TJ01 | 39 | 70 | 177 | 10 | N/A | 400 | S, RT + TMZ, Bev | – |
| TJ02 | 57 | 80 | 90 | 9 | N/A | 1570 | S, RT + TMZ | – |
| TJ03 | 75 | 70 | 32 | 7 | 700 | 300 | S, RT + TMZ | – |
| TJ06/R[1] | 66 | 80 | 54 | 8 | 2000 | 1300 | S, RT + TMZ | – |
| TJ07 | 43 | 80 | 215 | 10 | 500 | 430 | S, RT + TMZ | + |
| TJ08 | 55 | 80 | 52 | 8 | 1000 | 500 | S, RT + TMZ | – |
| TJ09 | 57 | 80 | 61 | 7 | 1400 | 300 | S, RT + TMZ | – |
| TJ10 | 47 | 60 | 376 | 7 | N/A | 1800 | S, RT + TMZ | – |
| TJ11 | 39 | 70 | 32 | 11* | 2400 | 200 | S, RT + TMZ | – |
| TJ12 | 60 | 80 | 74 | 7 | 1100 | 600 | S, RT + TMZ | – |
| TJ13 | 64 | 80 | 182 | 11 | N/A | 2100 | S, RT + TMZ | – |
| TJ14/R | 77 | 90 | 30 | 9/11 | 1800 | 1100 | S, RT + TMZ | – |

[1]Compassionate retreatment;
*Protocol amendment to include control chamber filled with phosphate buffered saline;
S: surgery;
RT: radiation therapy;
TMZ: temozolamide chemotherapy;
Bev: bevacizumab chemotherapy;
IDH-1: isocitrate dehydrogenase-1

Safety Assessment and Clinical Course

Figure 19A:
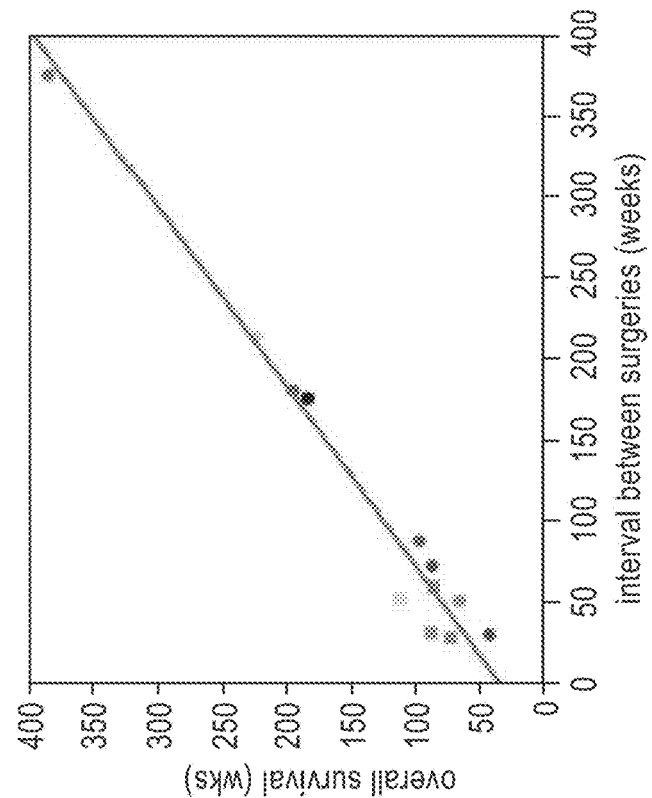
Figure 19B:
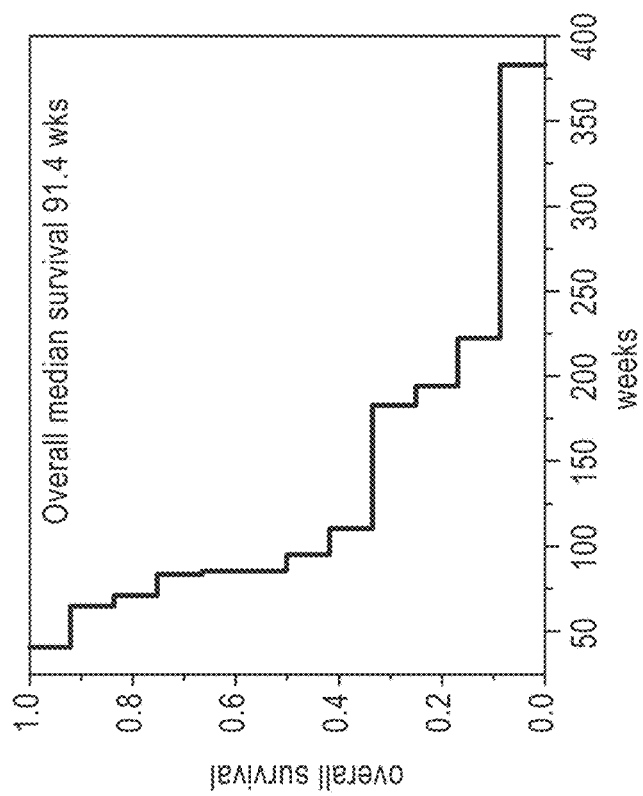

Of 54 severe adverse events recorded, only one SAE was related to the protocol involving a thrombus from a femoral port used for plasma leukopheresis. The incidence of DVT in the trial was 8.3%. Nine patients succumbed to tumor progression while three patients died from other causes including intracranial hemorrhage and septicemia (*candida glabrata, klebsiella pneumonia*). Five autopsies were performed. All patients were either weaned off steroids in the post-operative period or maintained on a daily dose as clinically indicated. Median overall survival was 91.4 weeks and correlated highly with the interval between initial surgery and surgery for recurrence. Following recurrent tumor surgery and autologous cell vaccination two significantly different protocol survival cohorts of 48.2 and 10 weeks were identified as longer and short survival cohorts, respectively. (FIG. 19A-FIG. 19C). Excluding one outlier (TJ03), we documented a significant correlation between protocol survival and degree of lymphopenia at enrollment (FIG. 19D). Comparison of values at initial diagnosis and at protocol enrollment indicated that the mean lymphocyte count had dropped significantly (65%) after standard therapy (eight available paired samples, p=0.012, paired t-test). There was no significant difference between lymphocyte counts at enrollment and at the last available lymphocyte counts after vaccination (data not shown).

Radiographic Responses

Figure 20A:
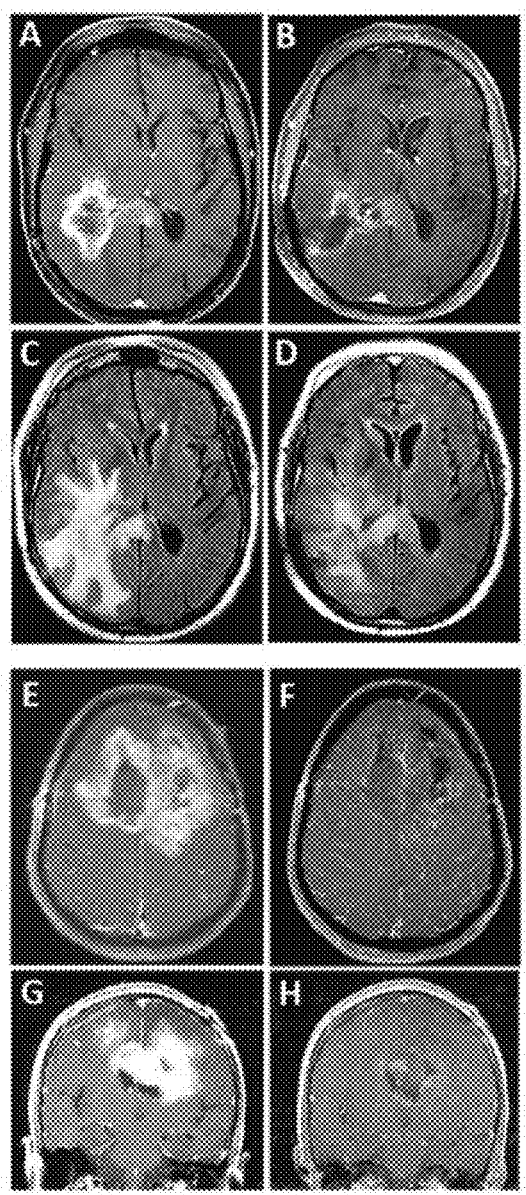
FIG. 20A-FIG. 20F depicts radiographic responses of anatomic tumors.
Figure 20B:
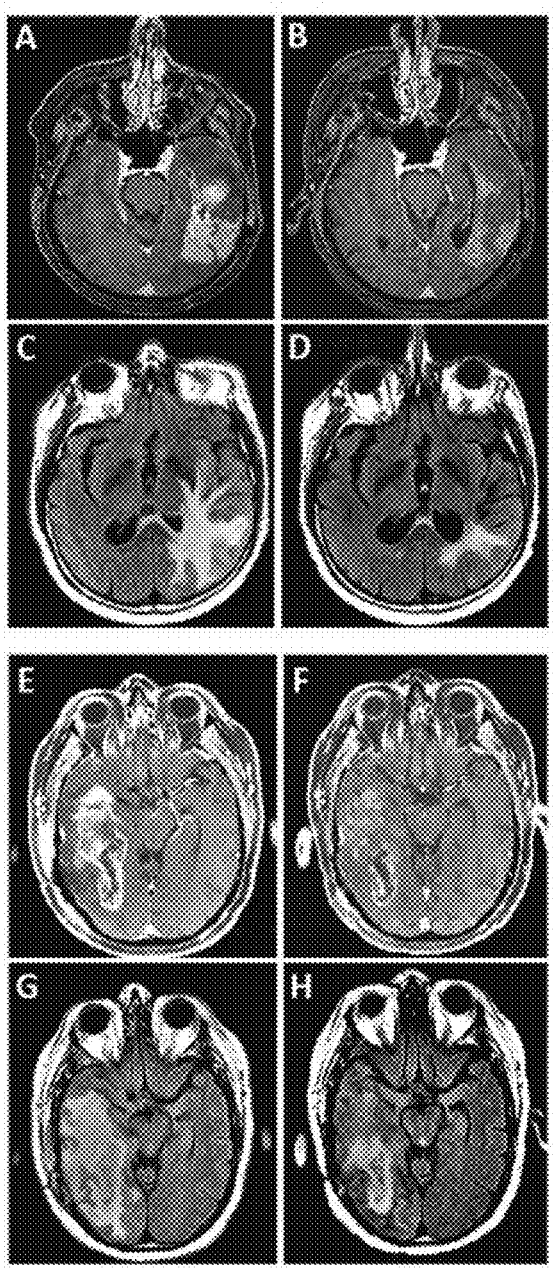
Figure 20C:
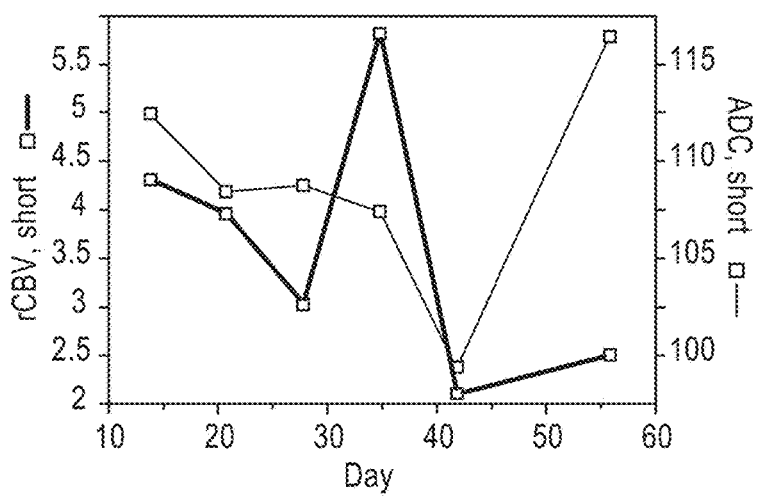
Figure 20D:
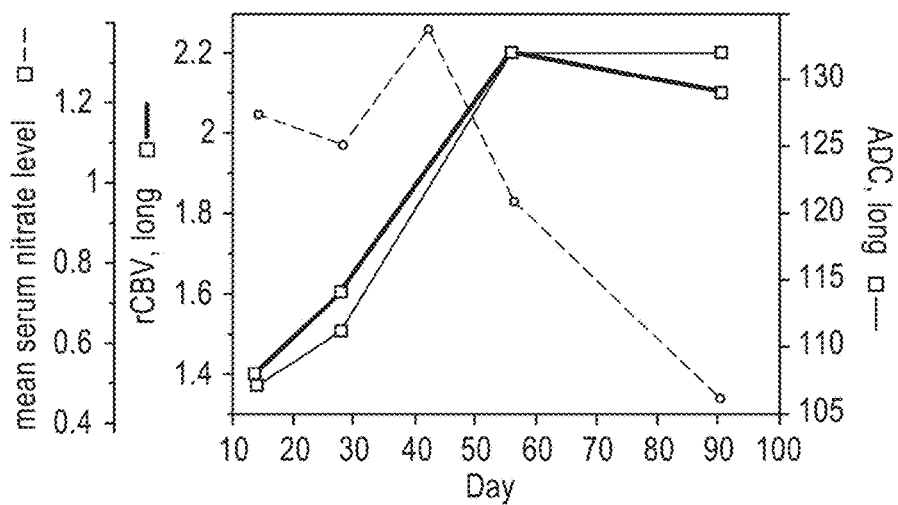
Figure 20E:
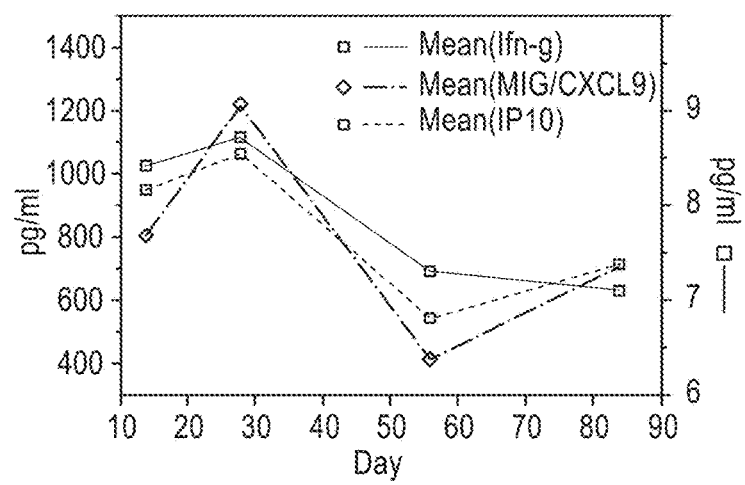
Figure 20F:
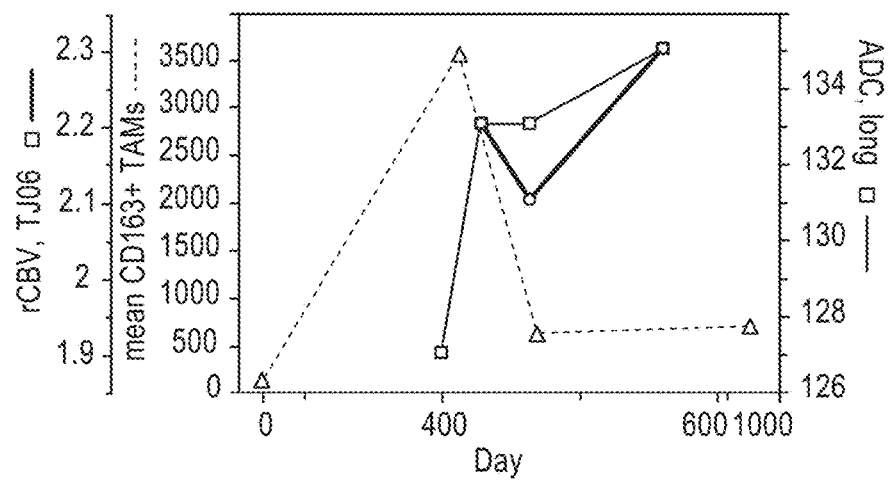

Anatomic tumor responses were scored and examples are noted in FIG. 20A and FIG. 20B. Standard MRI anatomic improvements did not correlate with survival, but additional imaging criteria did. Three of the four longer survival cohort (TJ03, TJ06, and TJ09) had a paradoxical increase in rCBV highly correlated with an increasing apparent diffusion coefficient (ADC, see FIG. 20C). This was considered paradoxical because these patients, despite perfusion data suggesting disease progression, had ADC values reflecting cell loss within the tumor. In the case of TJ06, a significant and sustained decrease in the CD163+ macrophage population was noted at second vaccination that carried forward to autopsy (FIG. 20D and see below). In two of these cases PET/CT criteria consistent with inflammation were observed, corroborating these findings (FIG. 24). Summary cytokine plots favored a pro-inflammatory process in these three patients (FIG. 20E).

Examination of Explanted Chambers and Pathologic Specimens

Figure 3A:
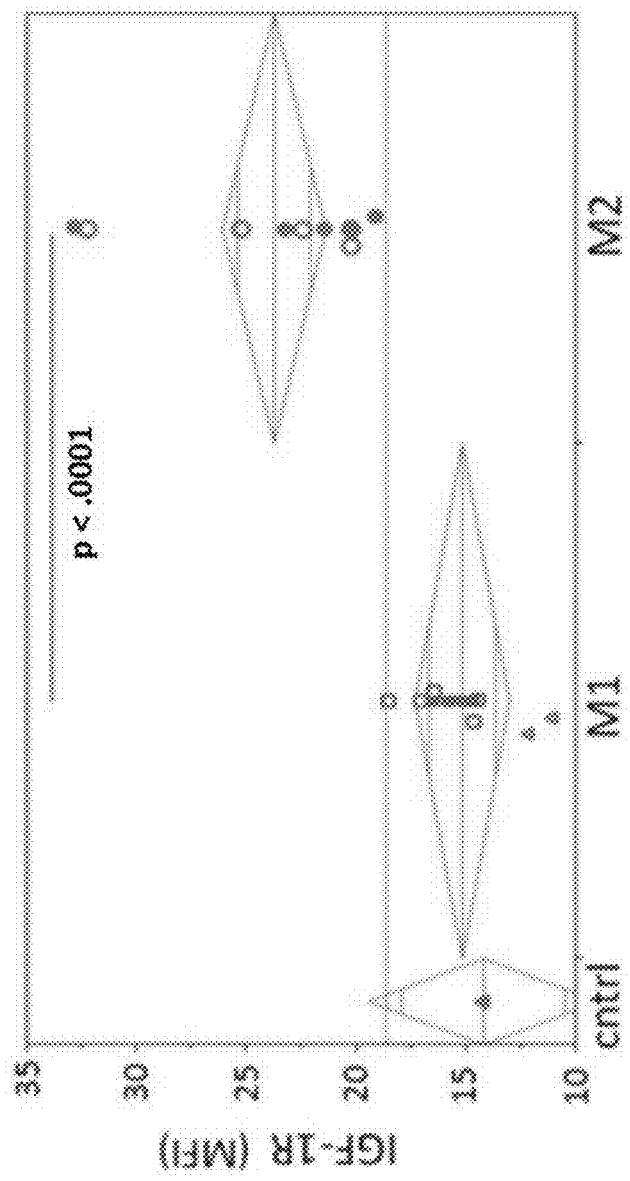
FIG. 3A and FIG. 3B depict flow cytometry of cells with expression of Insulin-like Growth Factor 1 Receptor (IFG-1R). Normal peripheral monocytes polarized to M2 cells in vitro overexpress the IGF-1R compared to macrophages induced to an M1 polarization. Further, the IGF-1R AS ODN selectively induces cell death in the M2 subpopulation in a dose-dependent manner.
Figure 3B:
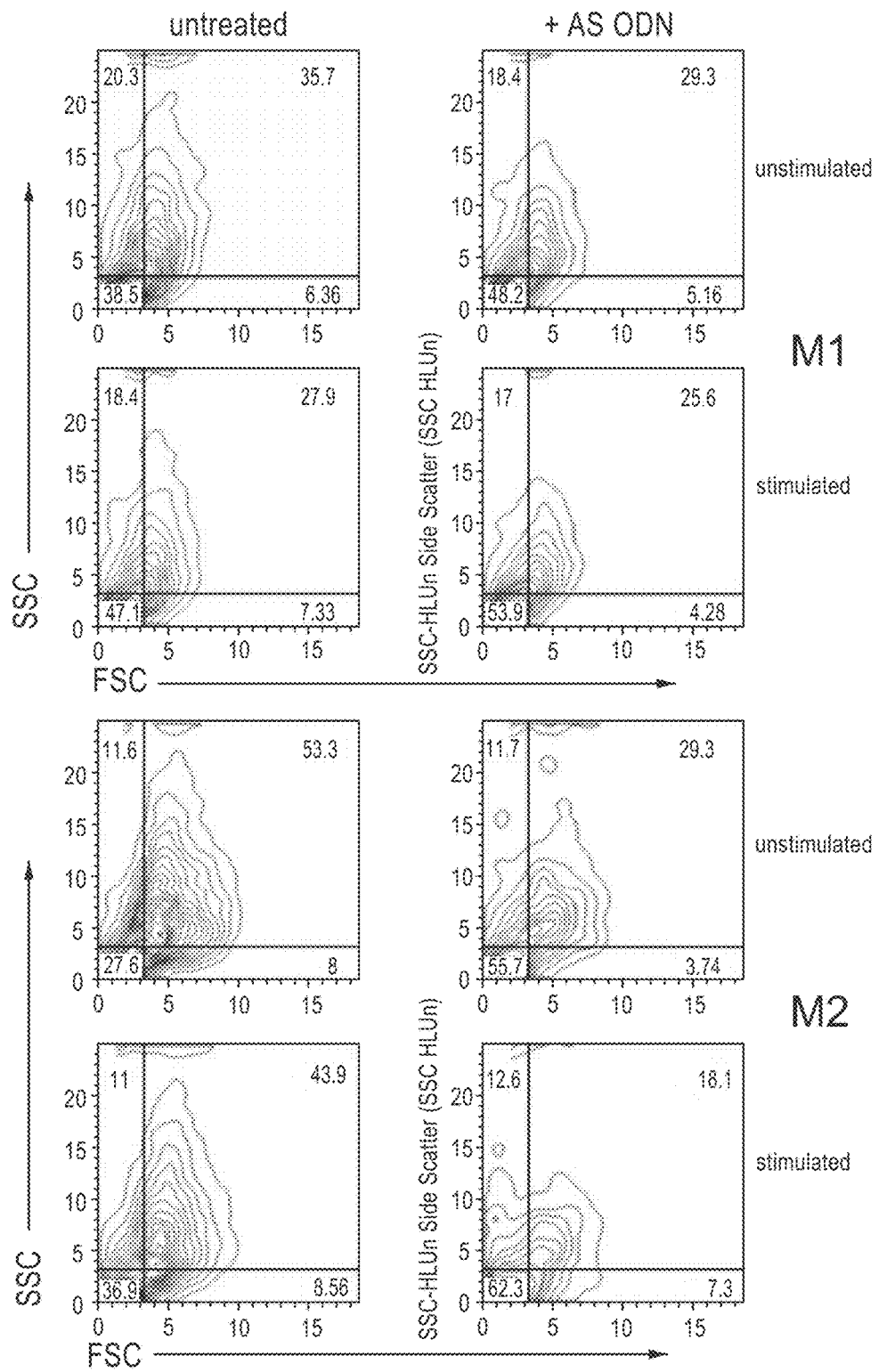
Figure 5A:
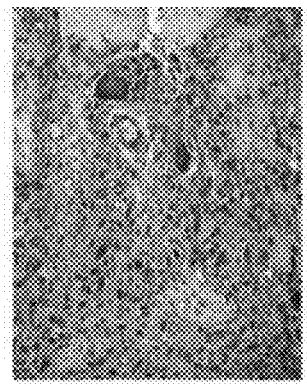
FIG. 5 shows immunohistochemistry for IGF-1R in 6 consecutive glioblastoma multiforme specimens (FIG. 5A-FIG. 5F). All tumors demonstrated IGF-1R immunoreactivity indicating the presence of one or more IGF-1R-expressing cells in the tumor microenvironment and identifying IGF-1R as a target for cancer therapy.
Figure 5B:
Figure 5C:
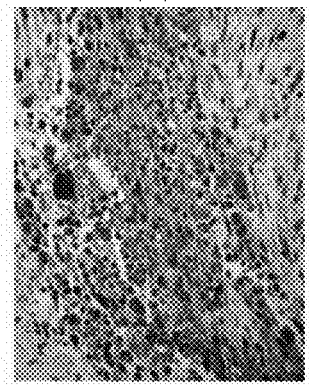
Figure 5D:
Figure 5E:
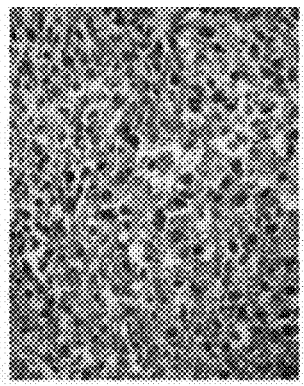
Figure 5F:
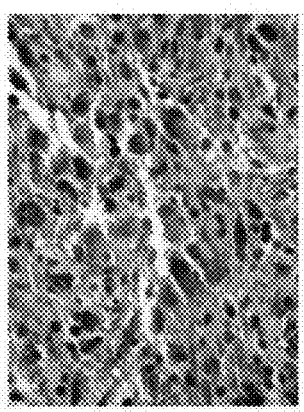
Figure 6A:
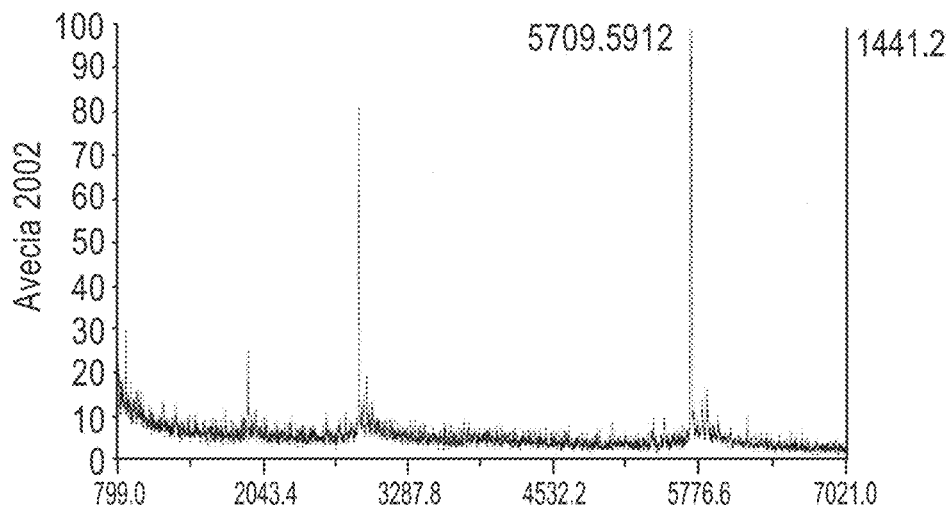
FIG. 6A-FIG. 6F depict mass spectrometry of two different sequence lots of IGF-1R AS ODN.
Figure 6B:
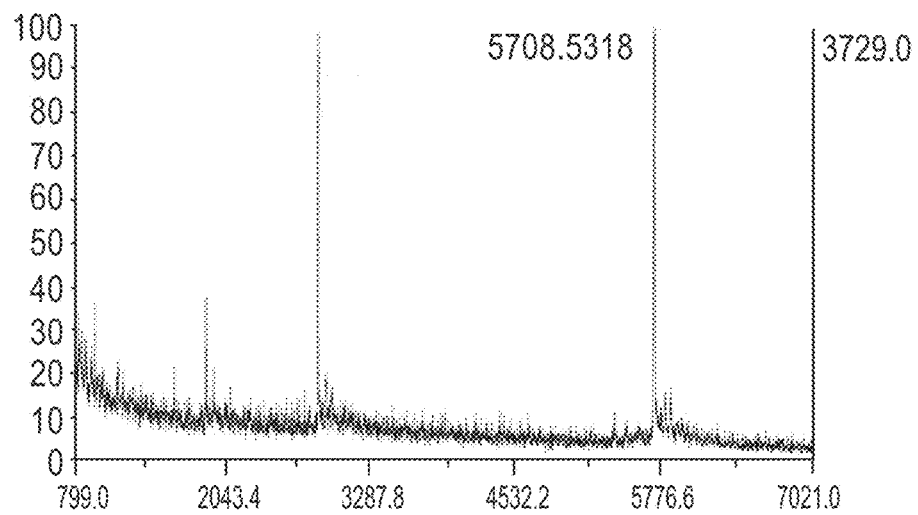
Figure 6C:
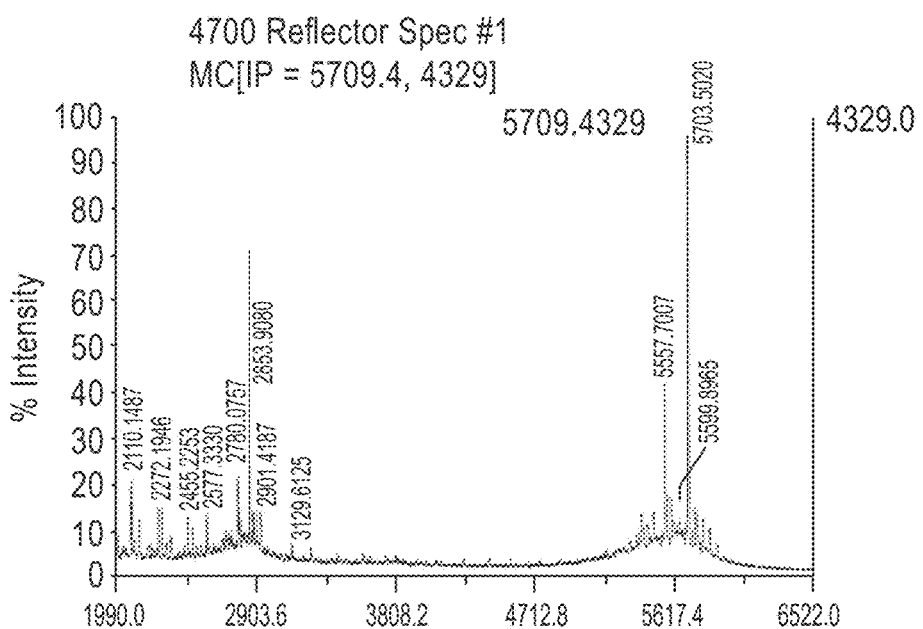
Figure 6D:
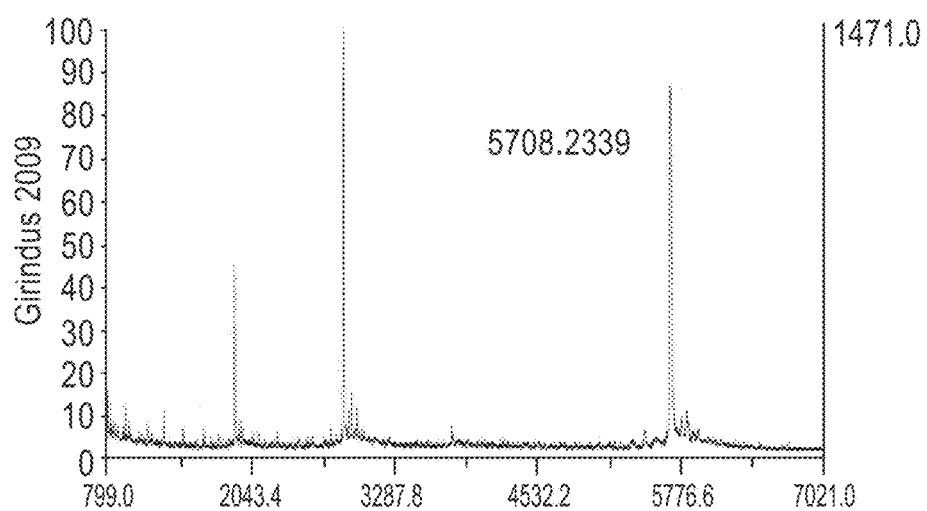
Figure 6E:
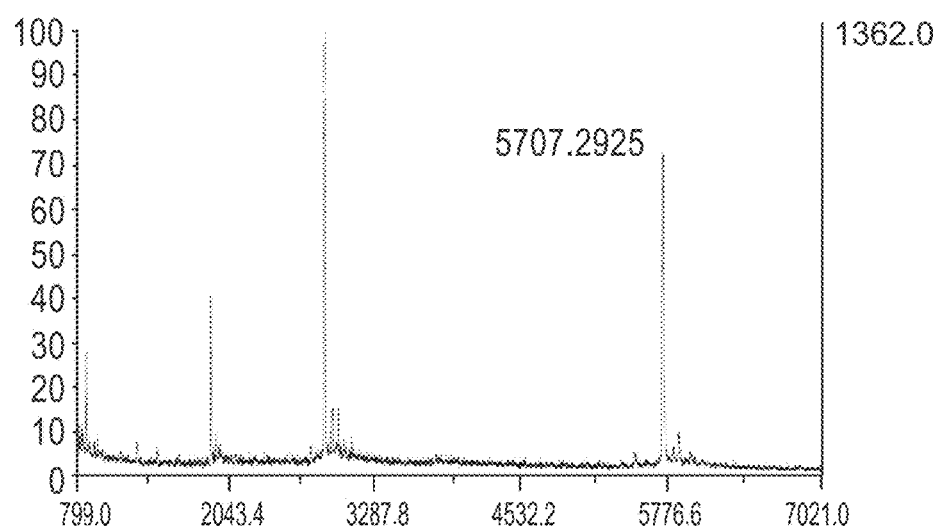
Figure 6F:
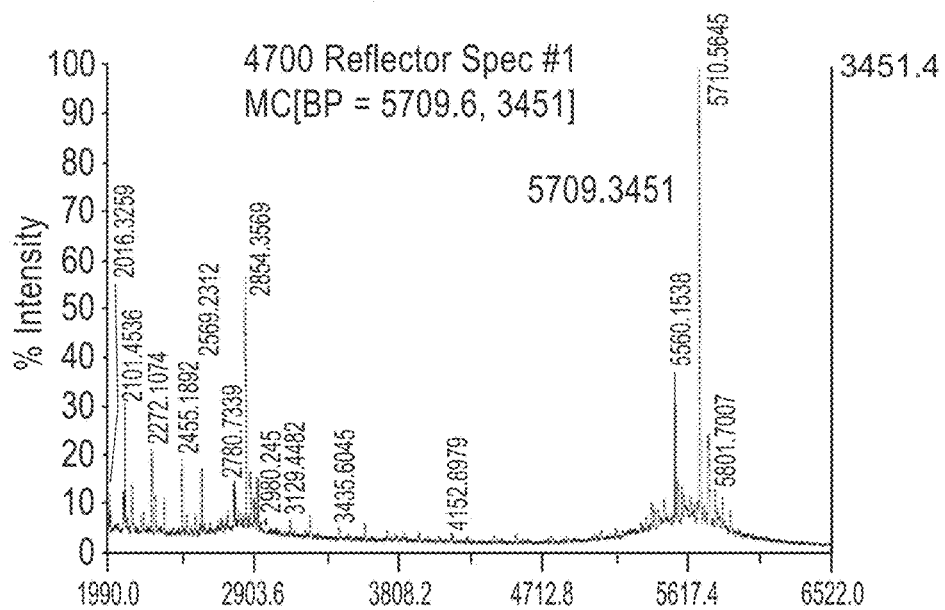
Figure 25:
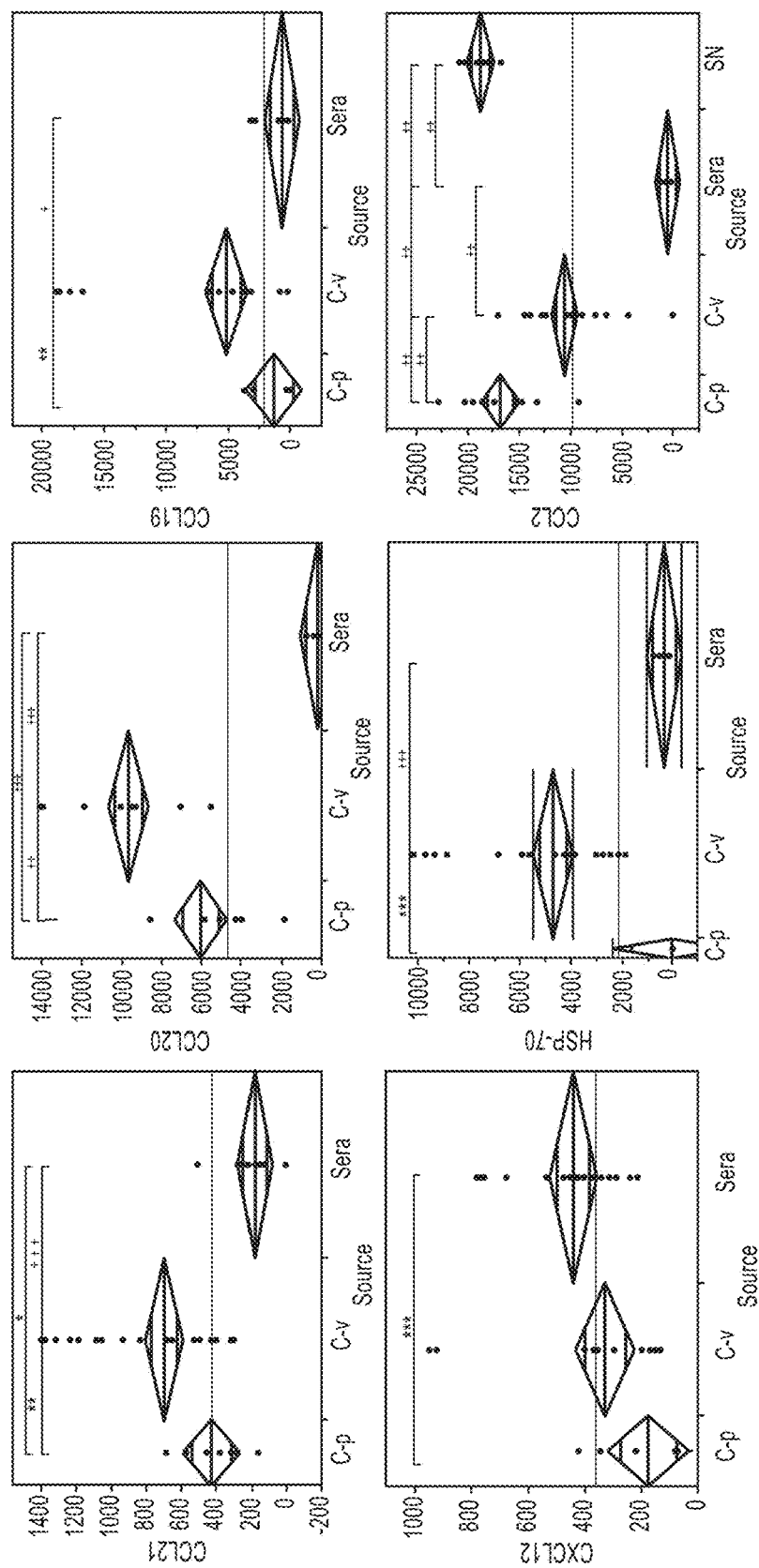
FIG. 25 shows a comparison of mean cytokine levels by source (pg/ml) (C-p, PBS chamber; C-v, vaccine chamber; sera; SN, autologous tumor cell supernatant). CCL21 is significantly elevated in the vaccine chamber compared to both C-p and sera. CCL20 is significantly elevated in C-v and C-p v. sera; CCL19 was significantly elevated in C-v vs. C-p or sera. HSP-70 is significantly elevated over sera; CCL2 is significantly elevated over sera; CXCL12 is the only cytokine significantly elevated in sera vs. C-p. *p<0.035, p<0.025, *p<0.015, †P<0.004, ††p<0.0002, †††p<0.0001.

Explanted chambers were structurally intact and contained no viable cells by Trypan blue exclusion. Histologic analysis of membranes from the chambers revealed that CD15+ neutrophils and CD163+ macrophages were coating the outer surface of membranes from both C-p and C-v chambers but with a dramatic increase on C-v (FIG. 3A). The chamber contents reflected the products of the encapsulated cells and inward diffusion of factors from the surrounding environment, with the control C-p chamber controlling for the latter. Chemokines elevated in C-v by comparison with C-p included CCL21, CCL20, and CCL19, all of which were also significantly increased over serum levels. CXCL12 was elevated in C-v and sera by comparison with C-p (FIG. 25 and Table 6). Also, significant elevations of HSP-70 and granzyme B in C-v compared to sera were noted (3826 pg/ml v. 327 pg/ml, p=0.0015, and 37 pg/ml v. 12 pg/ml, p=0.01, respectively). These results demonstrate that the methods disclosed herein induce pro-inflammatory immune responses that enhance anti-cancer effect.

TABLE 6

Matched pairs analysis of cytokines derived from three sources in each of five study subjects.

| Cytokine (pg/ml) | | | Matched pairs comparison |
|---|---|---|---|
| CCl21 | C-v | 635 | C-v > C-p, p = .0385 |
| Source | C-p | 383 | serum < C-v = .0318 |
| (N = 5) | serum | 214 | |
| CCl20 | C-v | 9430 | serum < C-v, p < .0001 |
| Source | C-p | 6686 | serum < C-p, p < .016 |
| (N = 5) | serum | 156 | |
| CXCL12 | C-v | 394 | C-v > C-p, p = .0224 |
| Source | C-p | 154 | Serum > C-p, p = .012 |
| (N = 5) | serum | 490 | C-v vs. serum, NS |

Figure 21A:
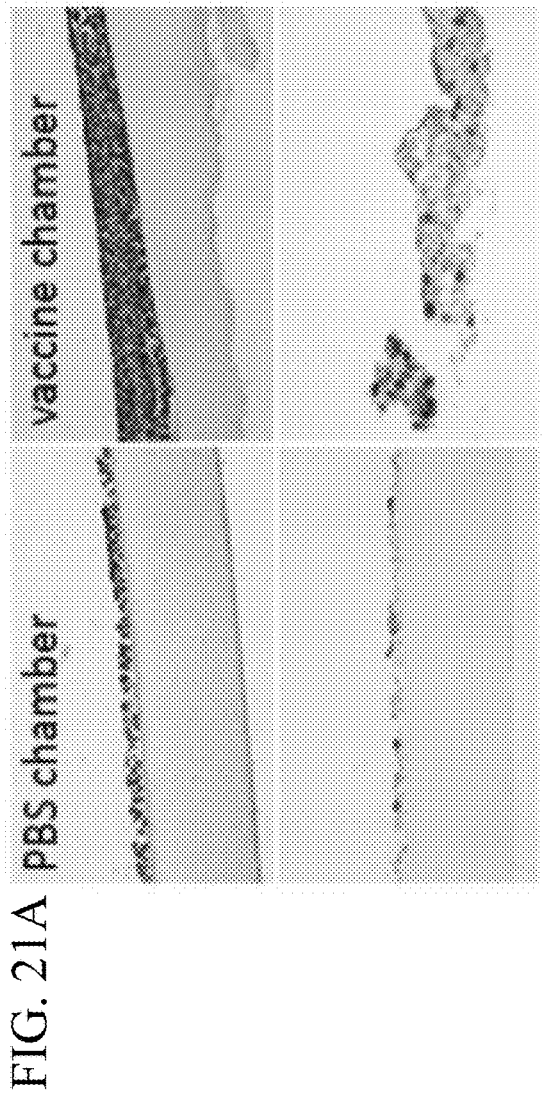
Figure 21B:
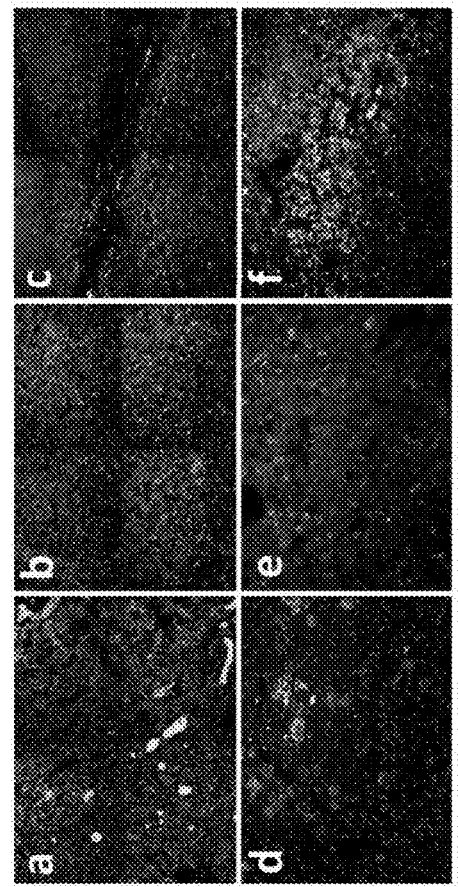
Figure 22A:
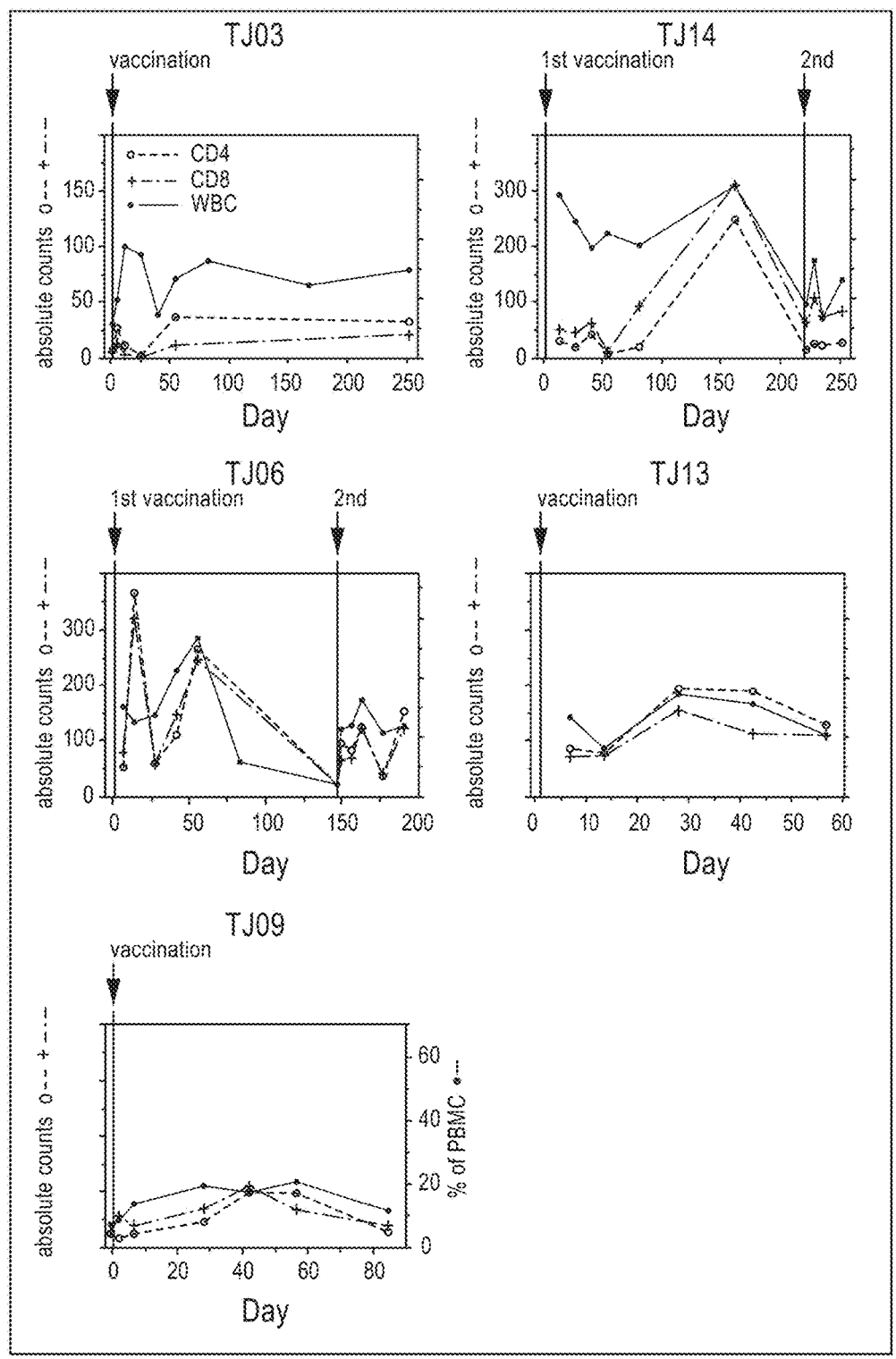
FIG. 22A-FIG. 22E depict serial measurements of immune effector cell shifts and cytokine/chemokine shifts after induction vaccination in the post-treatment period; longer survival cohort, (patients TJ03, TJ14, TJ06, TJ09); example of short survival cohort, (patient TJ13 for all other short survival cohorts, see FIG. 25). Rows.
Figure 22B:
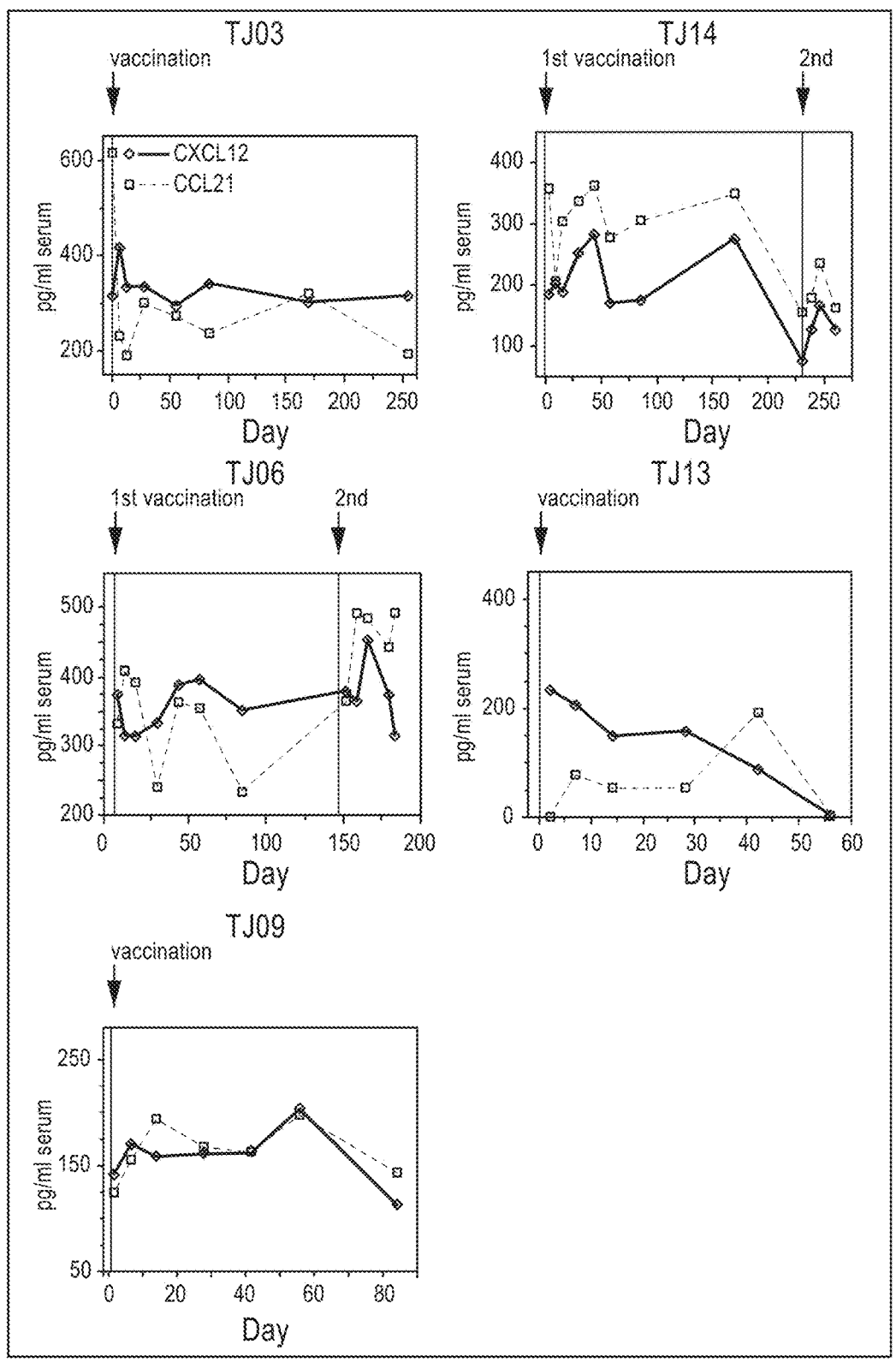
Figure 22C:
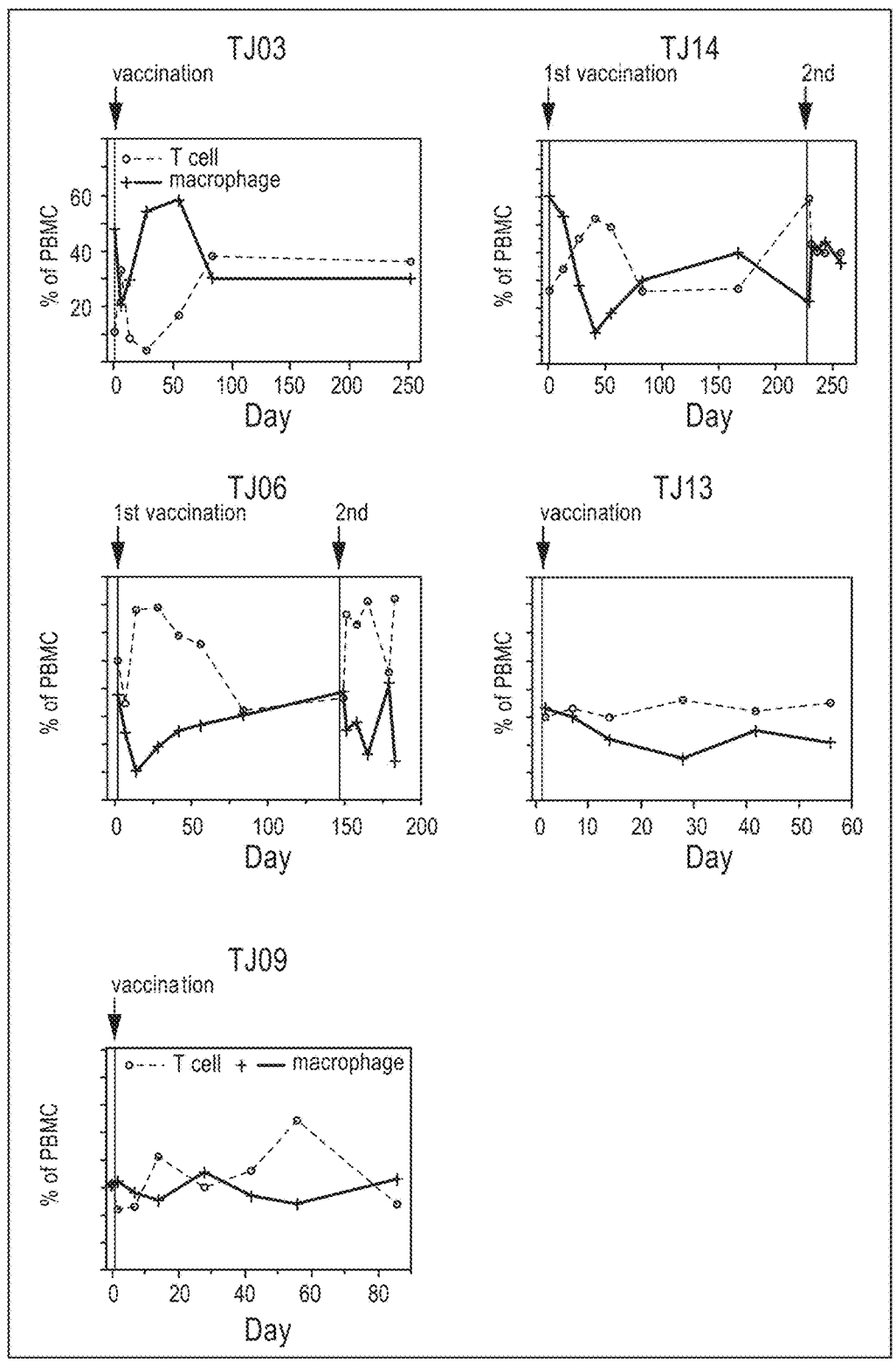
Figure 22D:
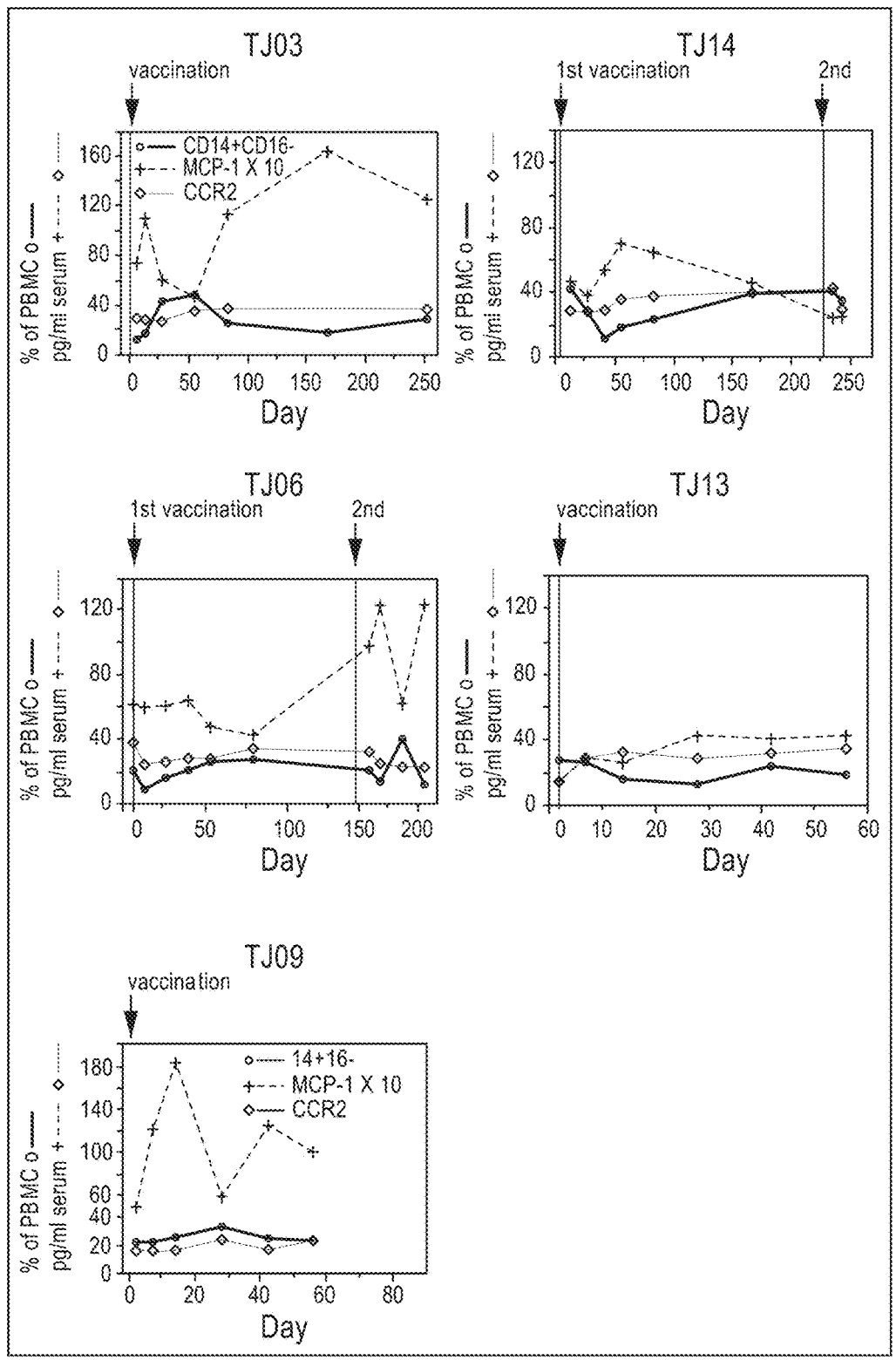
Figure 22E:
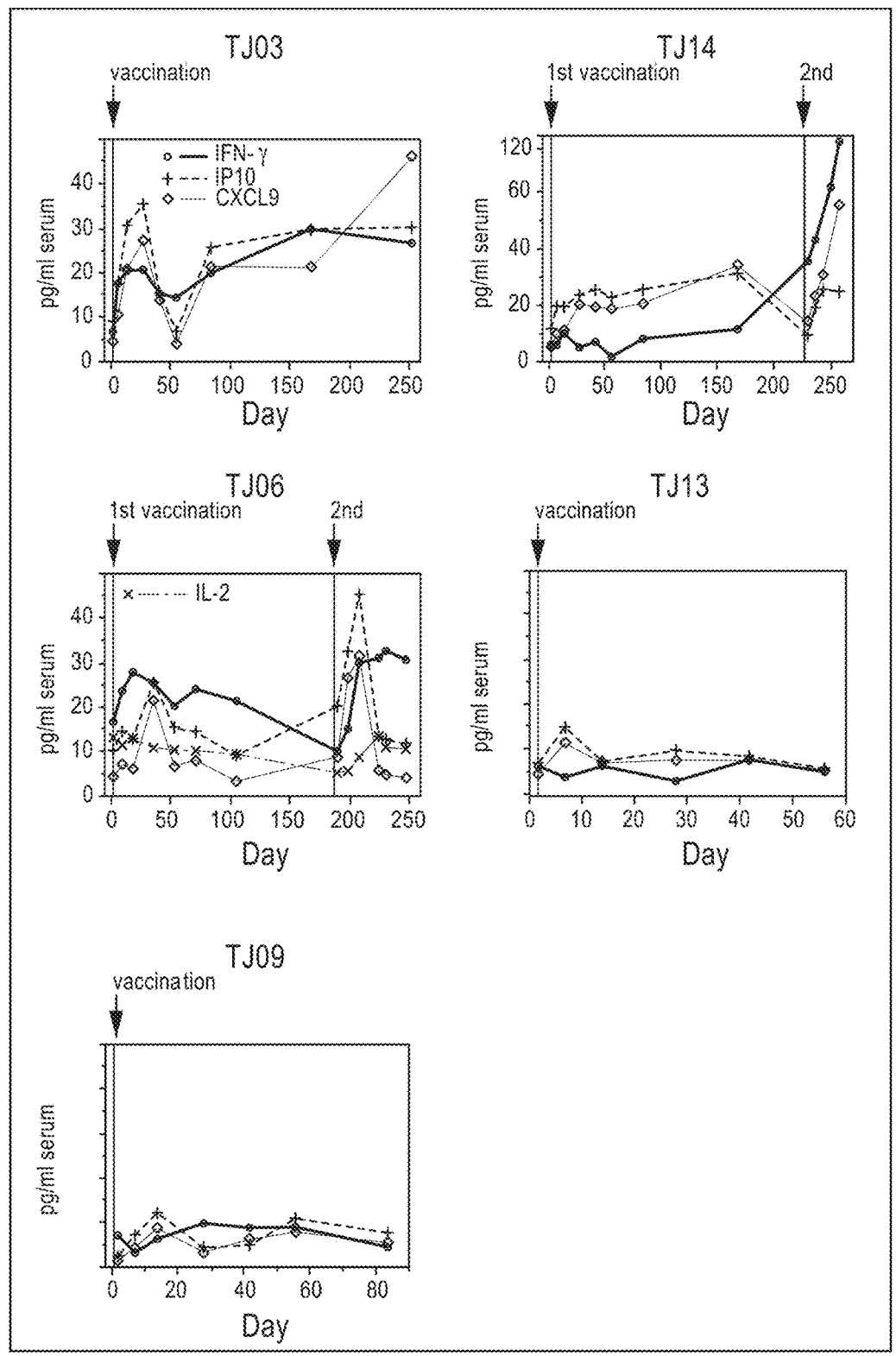
Figure 23A:
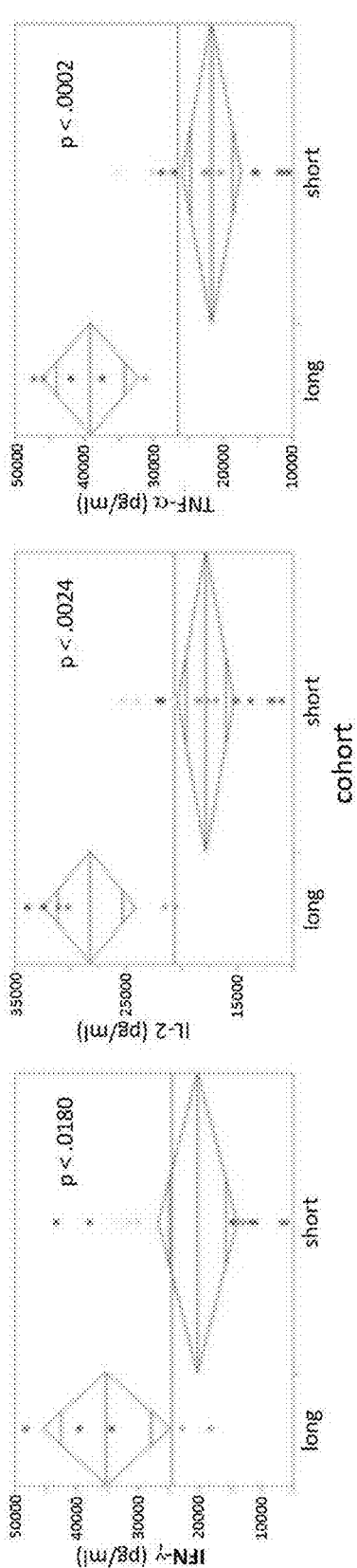
FIG. 23 depicts a summary of cytokine levels (pg/ml) at day 14 for FIG. 23A. putative Th-1 cytokines.
FIG. 23B. Th-2 associated cytokines, after PMA/ionomycin stimulation, by survival cohort. Comparison of means (Tukey) and unpaired t-test. Significance at p<0.05. TJ03 was excluded as an outlier with values consistently outside the 95% CI.
Figure 23B:
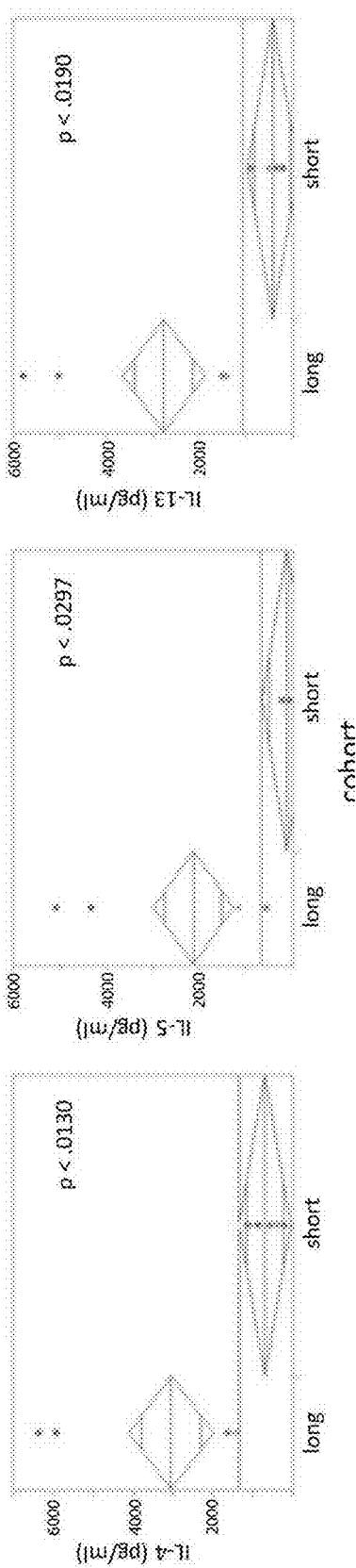
Figure 24B:
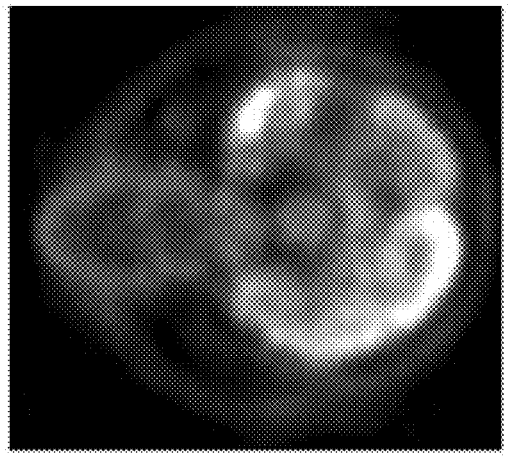
Figure 24D:
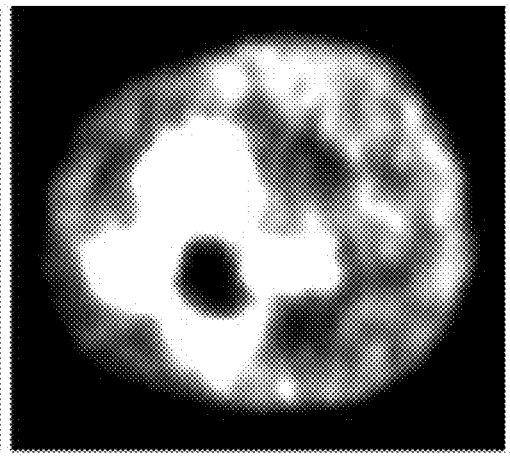
Figure 24A:
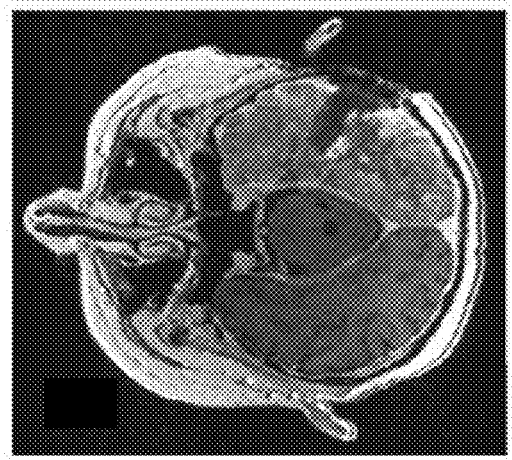
FIG. 24A and FIG. 24C: axial gadolinium-enhanced T-1W images.
Figure 24C:
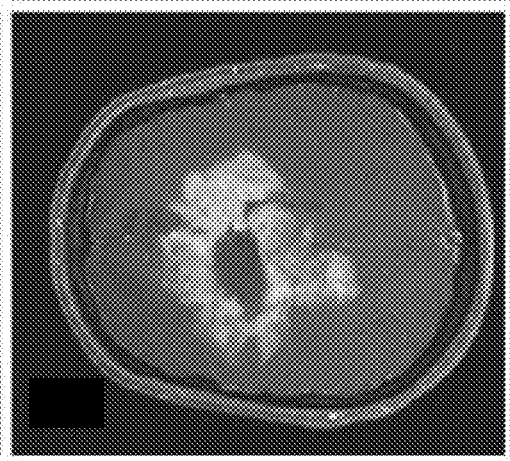
Figure 26A:
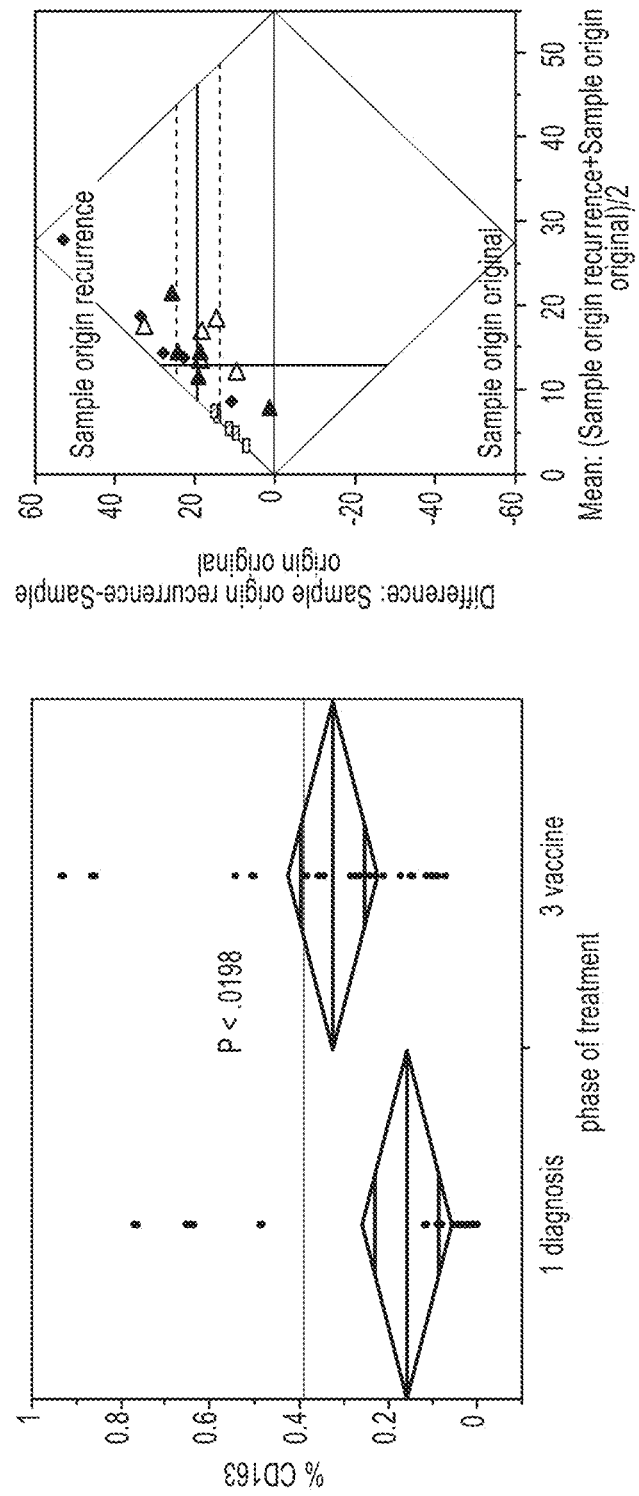
Figure 26C:
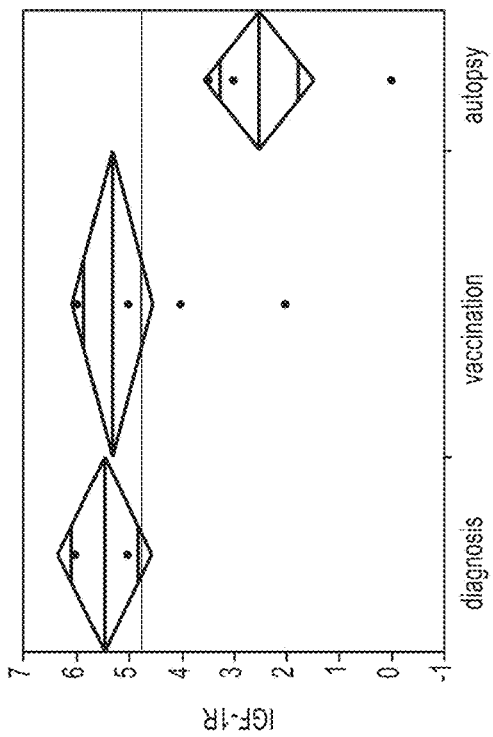
Figure 26D:
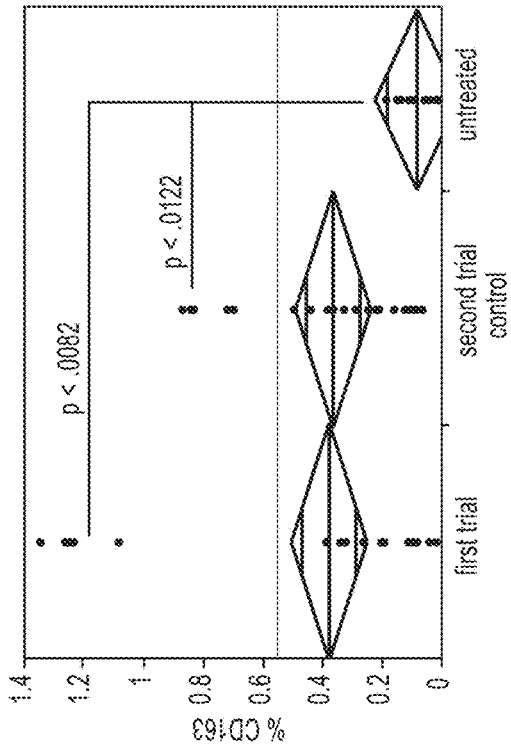

Paraffin sections from surgical interventions through autopsies were available for immunohistochemistry. A significant increase in the number of tumor-infiltrating CD163+ macrophages at vaccination versus initial diagnosis that decreased significantly at autopsy was noted in all evaluable cases (FIG. 21B and FIG. 26).

Levels of IGF-1R expressing cells were high throughout tumor tissues from initial diagnosis through surgery for recurrence, but a significant decrease in both at autopsy. Staining was too diffuse for immunopositive cell quantification by Aperio, so a qualitative scale was used. Comparison of pre-vaccination and post-vaccination levels revealed a significant decrease in IGF-1R positive cells (FIG. 21C and FIG. 26).

Figures 27A, 27B:
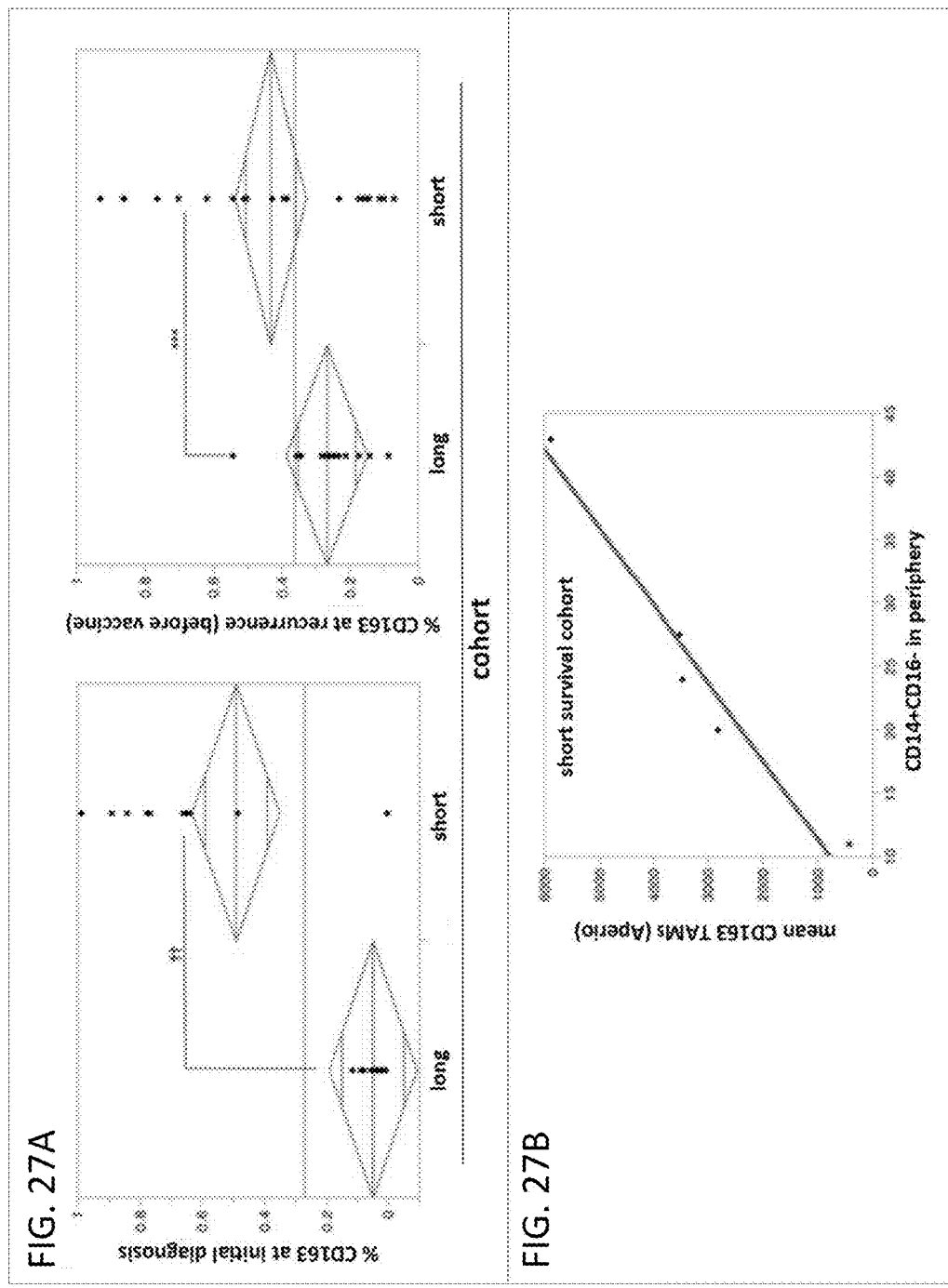
FIG. 27A. comparison of means for number of immunopositive cells/400× field detecting CD163 cells by survival cohort; left panel: at diagnosis, long v. short, p<0.0002; right panel: at tumor resection prior to induction vaccination, long v. short, p<0.0127.
FIG. 27B. linear regression of relationship between peripheral and tumor associated macrophages ($R^2$=0.96, p=0.004).
Figure 28A:
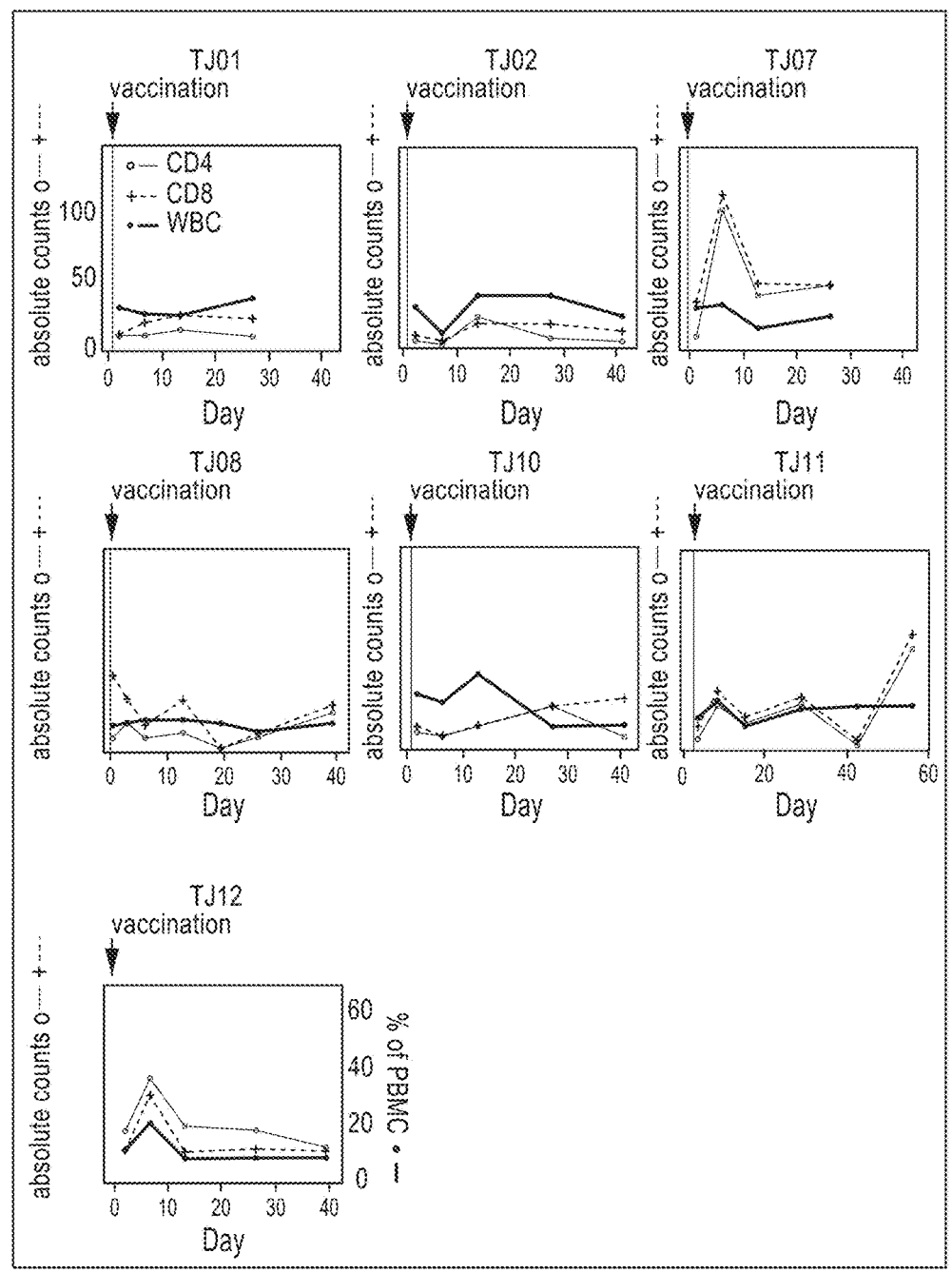
FIG. 28A-FIG. 28E depicts serial measurements of immune effector cell shifts and cytokine/chemokine shifts after induction vaccination in the post-treatment period for short survival cohort, (patients TJ01, TJ02, TJ07, TJ08, TJ10, TJ11, and TJ12, respectively); rows.
Figure 28B:
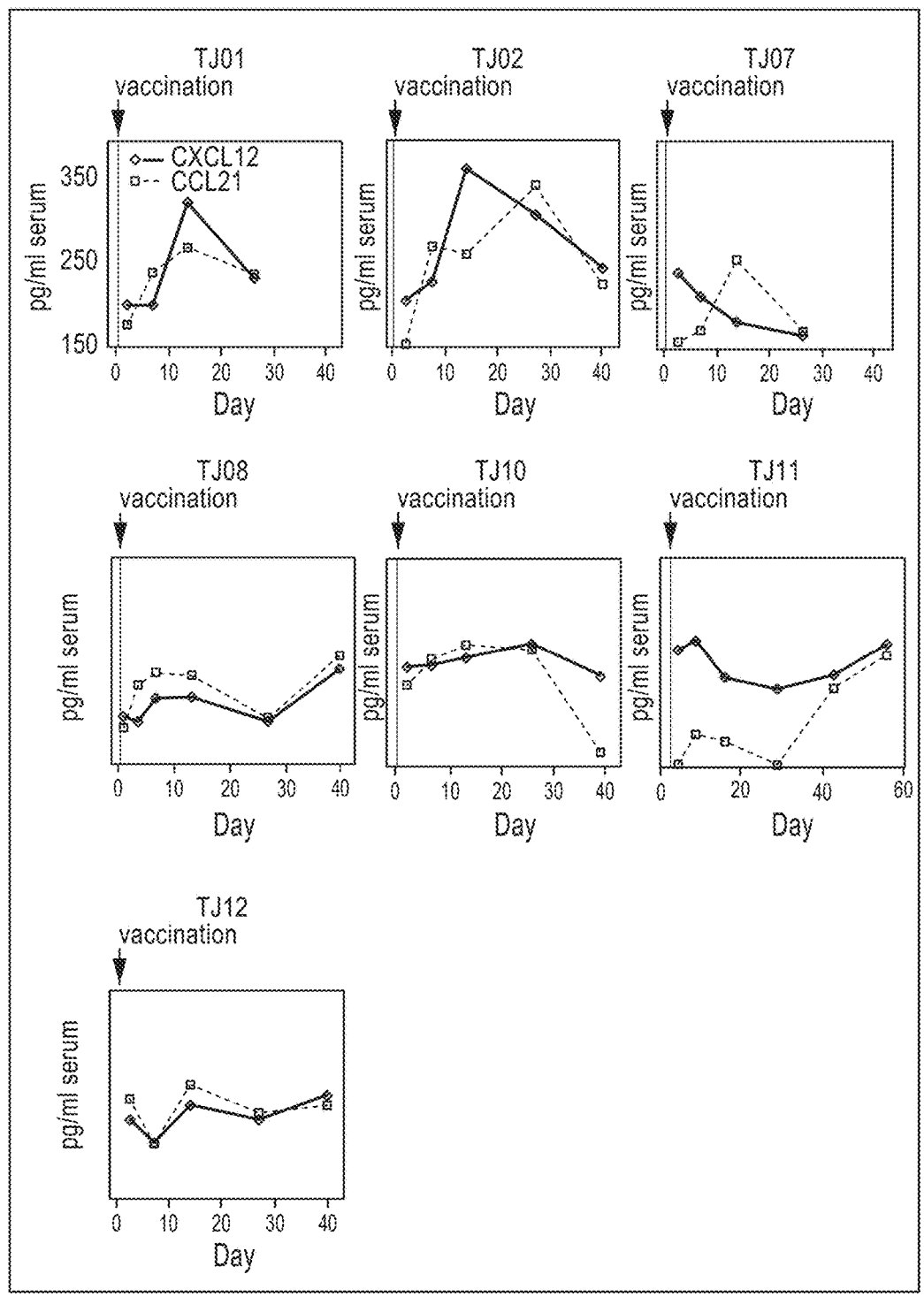
Figure 28C:
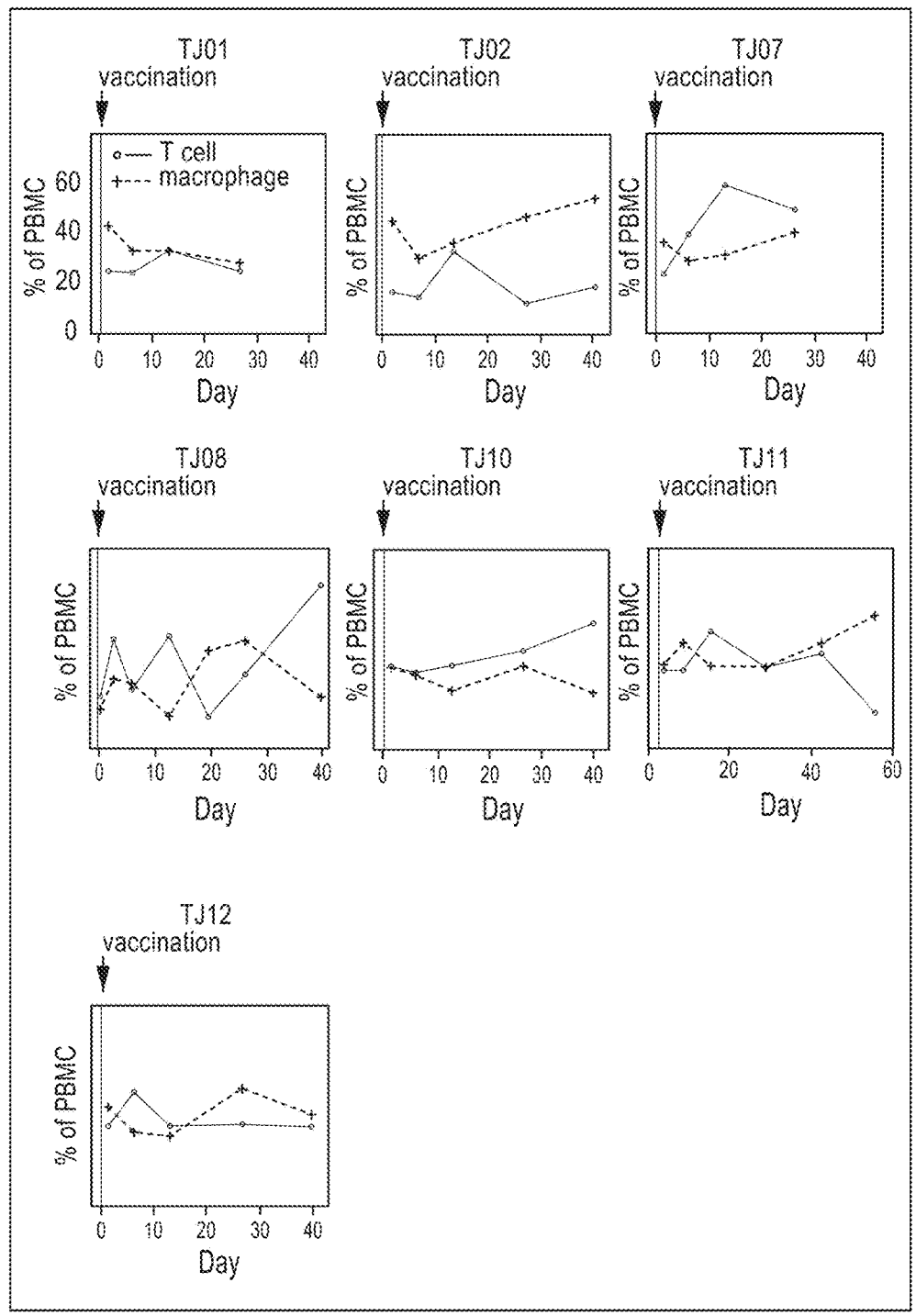
Figure 28D:
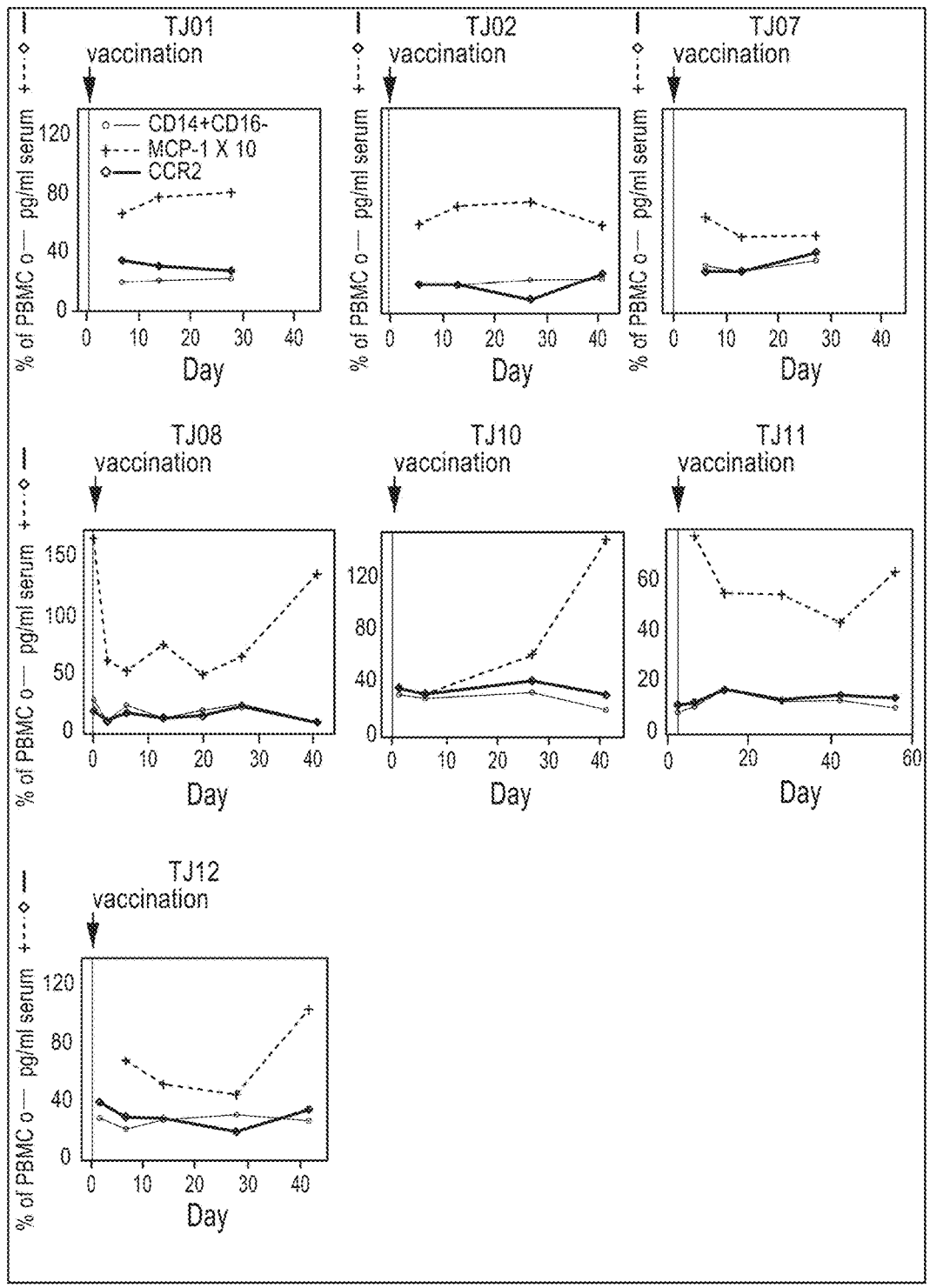
Figure 28E:
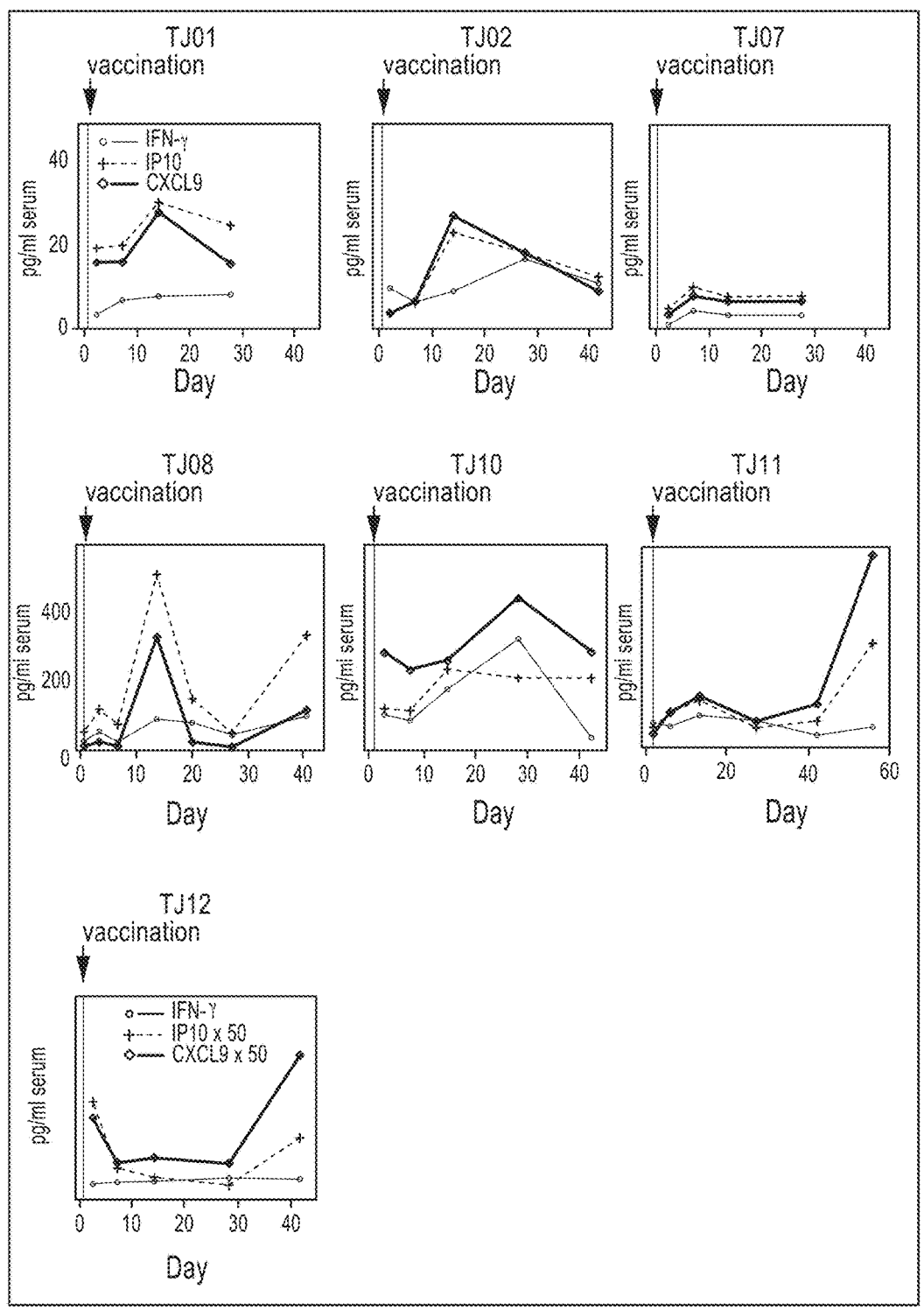

Comparing survival cohorts, we noted significantly lower levels of CD163+ TAMs at both initial diagnosis (3.7% v. 51.5%, p 0.0075) and at vaccination 26% v. 53.9%, p=0.0402) in the long survival compared to the short survival cohort (FIG. 27). Levels of TAMs correlated highly with circulating M2 cells in the short survival cohort (FIG. 27B). Few CD3, CD4, or CD8 cells were noted through all serial subject samples (data not shown).

Chemokine/Cytokine Content in Collected Samples

It was hypothesized that any significant increase in cytokines/chemokines in C-v may reflect their elevated presence in either the tumor microenvironment (TME) or sera. To gain further insight into this question it was explored whether cytoreductive surgery reduced serum levels of these cytokines. Excluding two outliers, of all serum cytokines/chemokines surveyed, serum CCL21 was significantly lower on post-operative day 2 (Table 6) supporting CCL21 production from the TME. Of interest, post-vaccination levels of T cells trended closely with levels of both CCL21 and CXCL12 in the longer survival subjects (FIG. 4). In contrast, we noted no associated patterns between T cells, monocytes or cytokines for the short survival cohort (FIG. 28).

CCL2 which was high in both SN and C-v was also significantly elevated in serum after vaccination suggesting a source of this chemokine other than the TME. The mean post-operative serum levels of CCL2 were also significantly higher in the short by comparison with the long survival cohort (3812 pg/ml vs. 1978 pg/ml, p<0.0078).

After initial vaccination and re-vaccination, the longer survival subjects manifested coordinated changes between circulating levels of T cells, monocytes, and pro-inflammatory chemokines/cytokines. Inverse relationships between T cells and macrophages and between the CD163+ subset of circulating CD14+CD16− macrophages and the chemokine CCL2 were noted. See Table 7 showing certain cytokines. In three of four subjects, circulating levels of CD163+ cells and CCR2+ cells were also directly correlated ($R^2$=0.68, p=0.043). A significantly higher CD4/CD8 ratio was apparent in the longer survival cohort in the post vaccination period.

TABLE 7

Matched pairs of cytokines before and after surgery:

| | cytokine | Day −7 | Day 2 | P value |
|---|---|---|---|---|
| ↓ | CCL21 | 228 | 120 | p < .002 |
| | GM-CSF | 11.8 | 6.9 | p < .0001 |
| | M-CSF | 81.5 | 56.9 | p < .034 |
| → | CXCL12 | 499 | 446 | p < .25 |
| | MCP-3 | 24 | 18 | p < .09 |
| | MDC | 257 | 218 | p < .34 |
| | CCL20 | 226 | 228 | p < .512 |
| ↑ | CCL2 | 79.2 | 476.8 | p < .0001 |
| | MCP-4 | 67 | 189 | p < .006 |
| | CCL19 | 133 | 605 | p < .03 |

T Cell Activation In Vitro

PBMC samples obtained at day −7 and day 14 were non-specifically stimulated with PMA/ionomycin and supernatants assessed for chemokine/cytokine levels. After excluding one profoundly lymphopenic outlier (TJ03), significant differences in the two survival cohorts were noted for six putative cytokines associated with classical Th-1 and Th-2 responses at day 14 (FIG. 5 and Table 8).

TABLE 8

PMA/Ionomycin stimulation before and after surgery, exclusive of TJ11.

| | | Longer survival cohort | | Short survival cohort | |
|---|---|---|---|---|---|
| Cytokine (pg/ml) | | (N = 4) | mean change | (N = 7) | mean change |
| IFNγ | Day −7 | 24,859 | 2,291 | 35,330 | −12,715* |
| | Day 14 | 27,151 | p < .5664 | 22,615 | p < .0201 |
| IL2 | Day −7 | 32,589 | −10,350 | 29,340 | −11,020* |
| | Day 14 | 22,239 | p < .0610 | 18,320 | p < .0179 |
| TNFα | Day −7 | 32,749 | −8,487 | 37,144 | −13,805* |
| | Day 14 | 30,522 | p < .3875 | 23,339 | p < .0060 |
| IL4 | Day −7 | 12,631 | −10,287 | 3,381 | −2,708* |
| | Day 14 | 2,344 | p < .1559 | 673 | p < .0247 |
| IL5 | Day −7 | 11,340 | −9,709 | 2,080 | −1,935* |
| | Day 14 | 1,631 | p < .1470 | 145 | p < .0383 |
| IL13 | Day −7 | 16,637 | −14,511 | 4,403 | −4,010* |
| | Day 14 | 2,126 | p < .1605 | 393 | p < .0284 |

Impact of surgery is less for longer v. shorter survival cohorts.
*significance at p < .05.

Example 14: Monocytes Polarized Towards the M2 Cells Overexpress IGF-1R

Figure 29A:
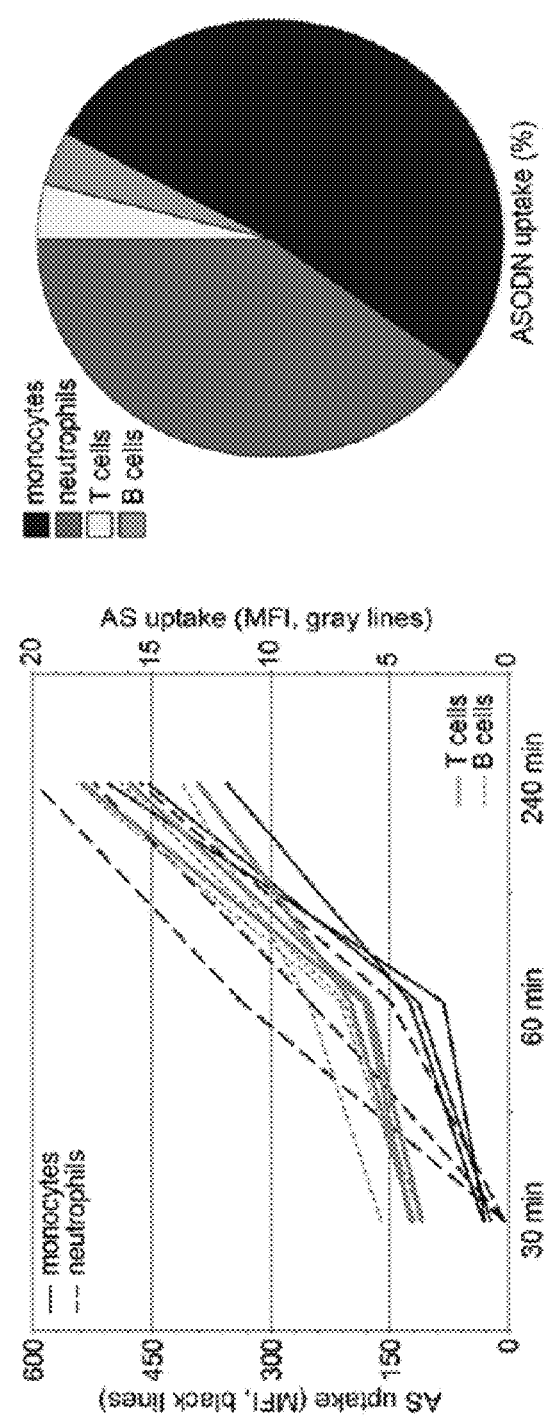
FIG. 29A demonstrates that the vast majority of IGF-1R AS ODN uptake occurs with monocytes and neutrophils.
Figure 29B:
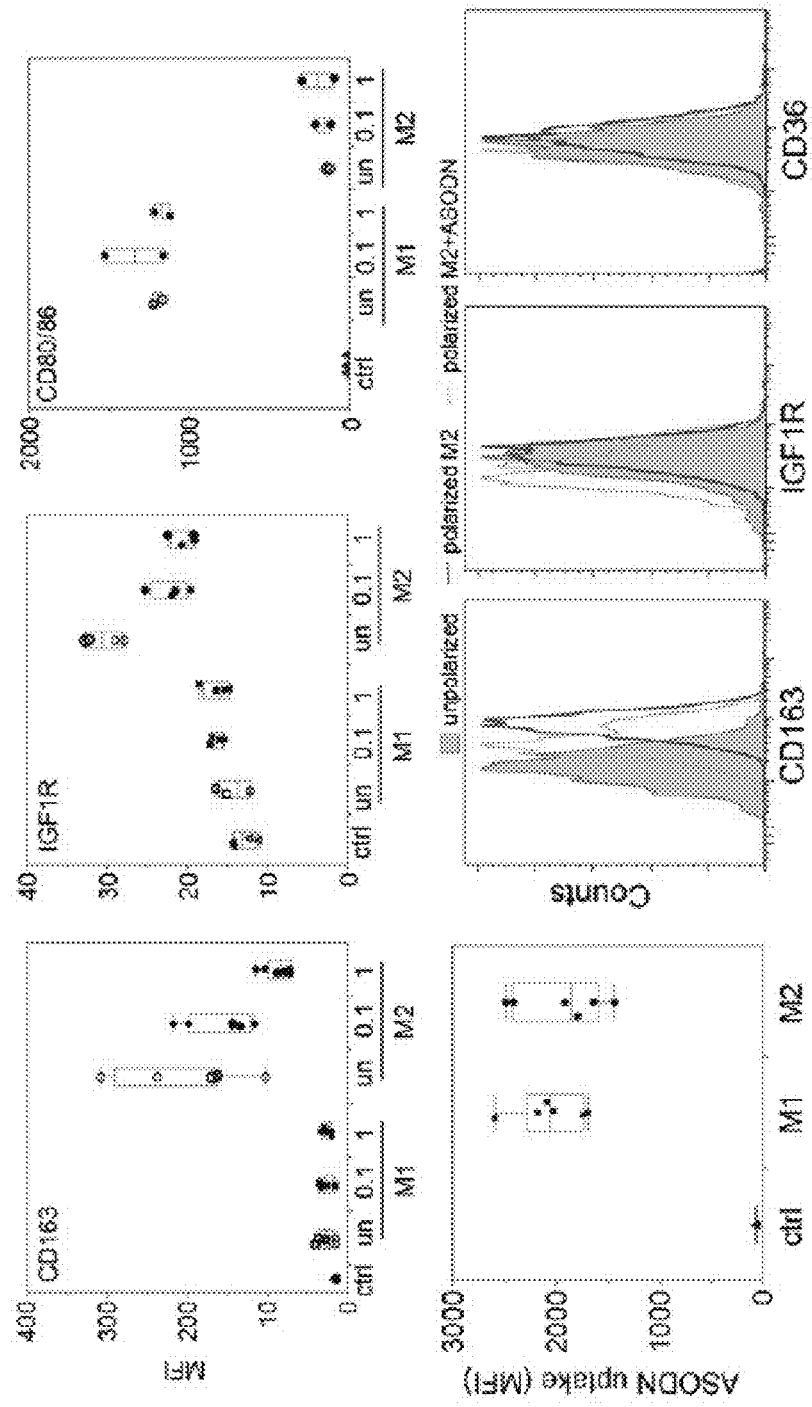
FIG. 29B. despite similar uptake of IGF-1R AS ODN in M1 and M2 cells, increasing concentrations of IGF-1R AS ODN targets selective elimination of M2 CD163+ cells with upregulation of IGF-1R only.
Figure 29C:
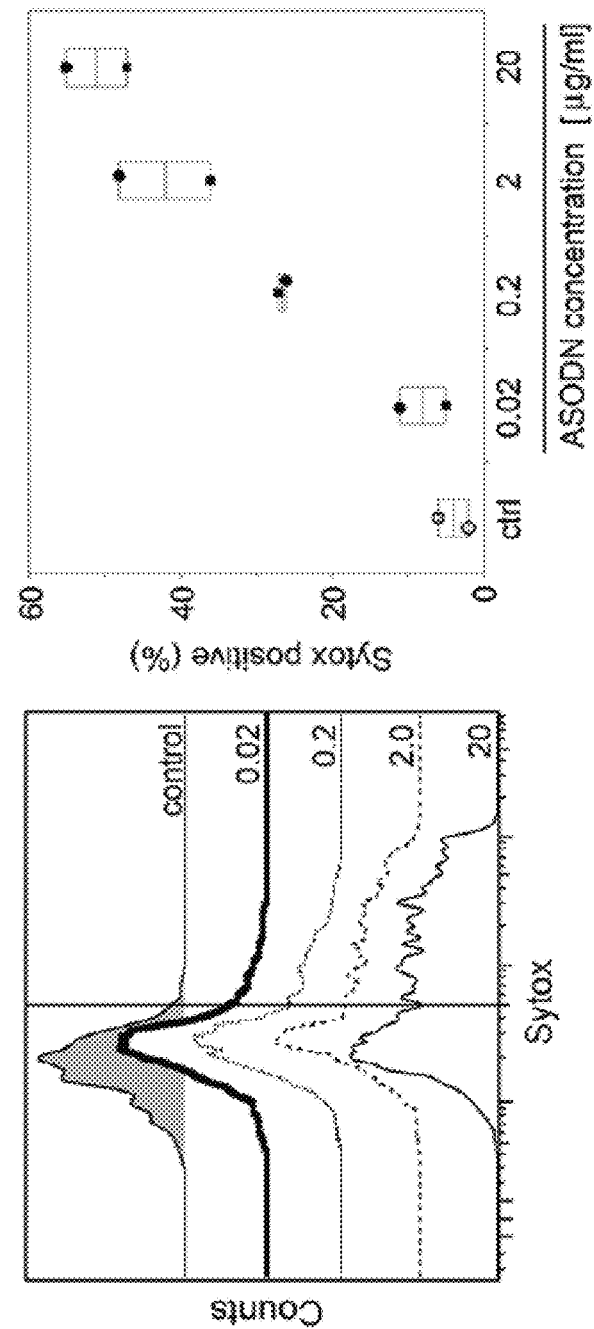
FIG. 29C. rate of apoptotic cell death of CD163+ cells is directly related to the concentration of IGF-1R AS ODN.

Immature undifferentiated human monocytes induced to an M2 polarization by canonical M2 differentiation by IL-4 and IL-13 overexpress IGF-1R compared to macrophages induced to an M1 polarization. Further, treatment with IGF-1R AS ODN selectively blocks the appearance of polarized M2 cells as well as the survival of existing M2 cells (FIG. 29). These observations represent new information about the immune system and support a therapeutic intervention involving targeted elimination of the M2 cells associated with poor prognosis in patients with a variety of cancers. FIG. 29a demonstrates that the vast majority of IGF-1R AS ODN uptake occurs with monocytes and neutrophils. Despite similar uptake of IGF-1R AS ODN in M1 and M2 polarized macrophages, increasing concentrations of IGF-1R AS ODN targets selective elimination of M2 CD163+ cells with upregulation of IGF-1R only (FIG. 29b). The rate of apoptotic cell death of CD163+ cells is directly related to the concentration of IGF-1R AS ODN (FIG. 29c).

Figure 30A:
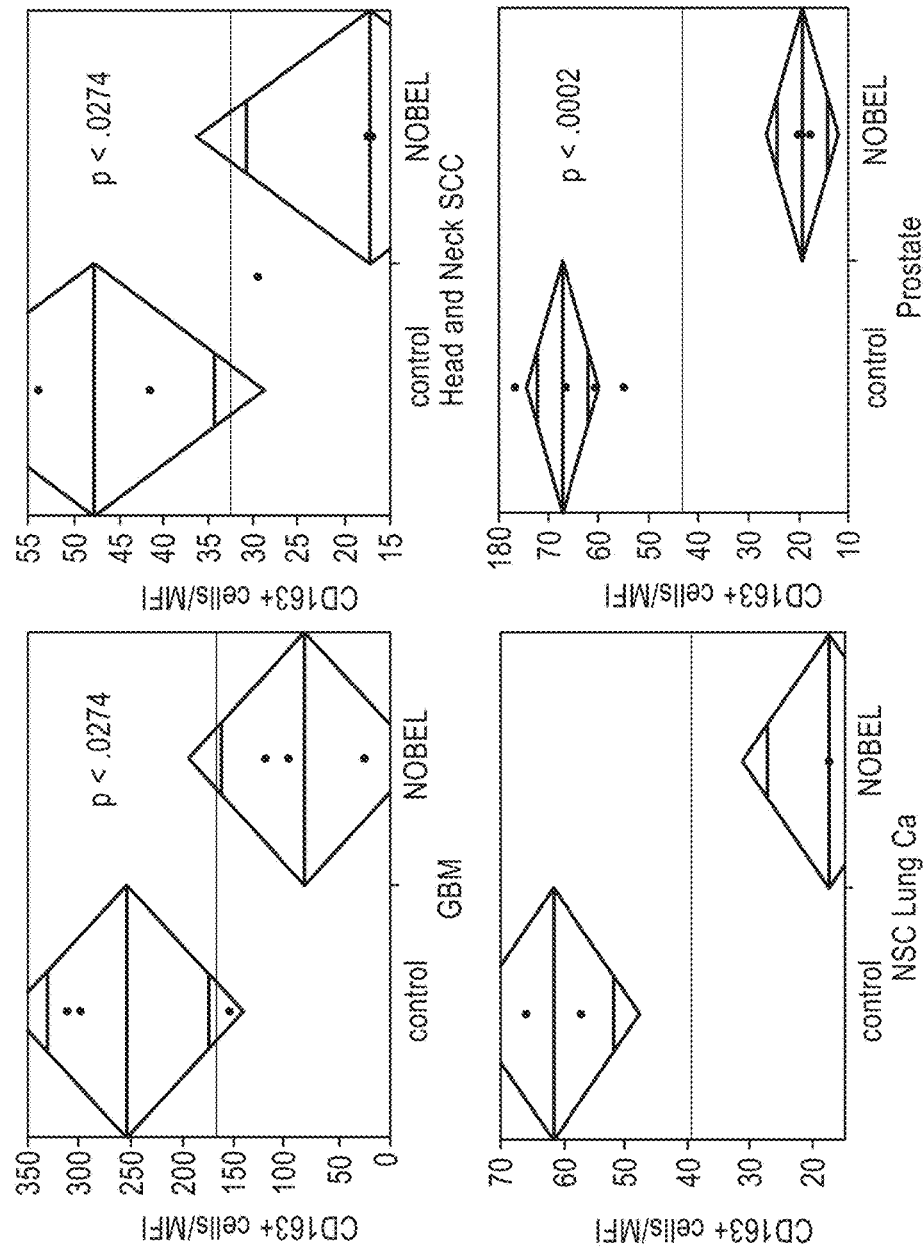
FIG. 30A and FIG. 30B depict polarization of monocytes towards M2 cells by incubation of normal monocytes in cancer patient sera.
Figure 30B:
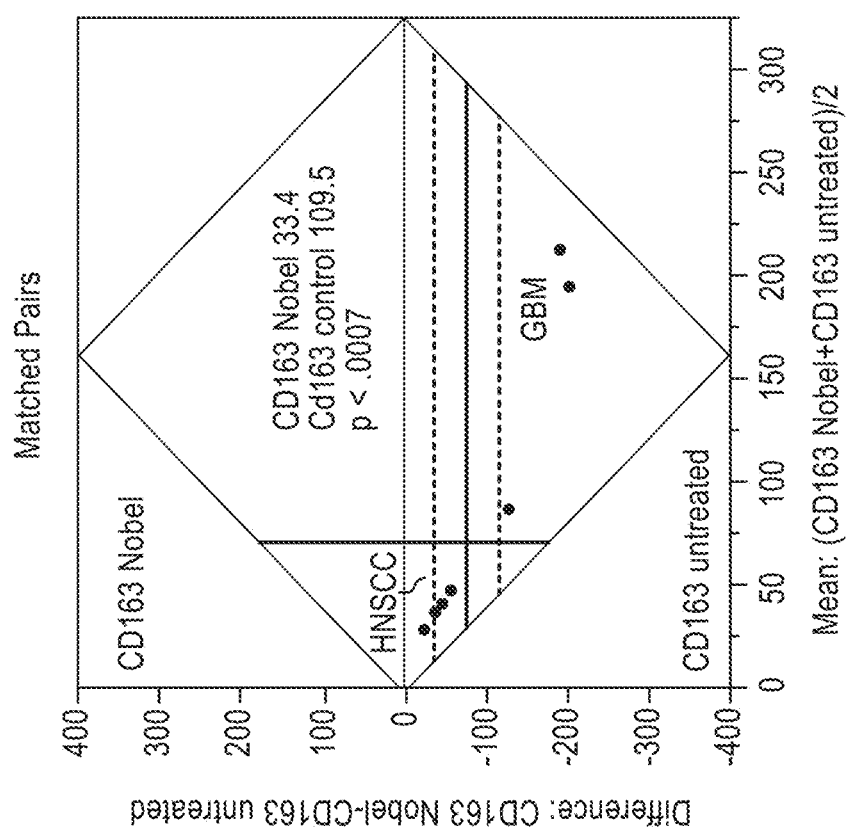

Example 15: Polarization of Monocytes Towards M2 by Incubation of Normal Monocytes in Cancer Patient Sera An analysis of patients with different types of cancers was performed to see if their serum was capable of CD163+ differentiation. As shown in FIG. 30, CD163+ macrophage differentiation was noted from undifferentiated monocytes coincubated with serum from head and neck squamous cell carcinoma (N=2), non-small cell lung carcinoma (N=2), and prostate cancer (N=5). In all cases, treatment with IGF-1R AS ODN knocked this cell population down. This provides confirmation that factors present in the sera of patients with a variety of cancers induce polarization of monocytes towards M2 monocytes differentially expressing CD163 and/or a variety of other phenotypic markers including CD204 and CD206.

Example 16: Monocytes Polarized Towards the M2 CD163+ Phenotype by Treatment with Sera from Patients with Different Cancers Show Upregulation of Both CD163 and PDL-1

FIG. 31 shows that monocytes polarized towards the M2 CD163+ phenotype by treatment with sera from patients with different cancers show upregulation of both CD163 as well as PDL-1; in both cases treatment with AS ODN knocks down both CD163 and PDL-1 by selectively targeting this population of cells. FIG. 31A shows a comparison of means for PBS control v. IGF-1R AS ODN (NOBEL, 250 μg) treatment of CD163+ macrophages expressing PDL-1. FIG. 31B shows that matched pairs analysis reveals highly significant decrease in this cell population reflected as significant reduction of PDL-1. Removal of a cell population that over-expresses PDL-1, releases cytotoxic T cells from a source of inhibition and thereby restores Type 1 immunity in these cancer patients.

Figure 33A:
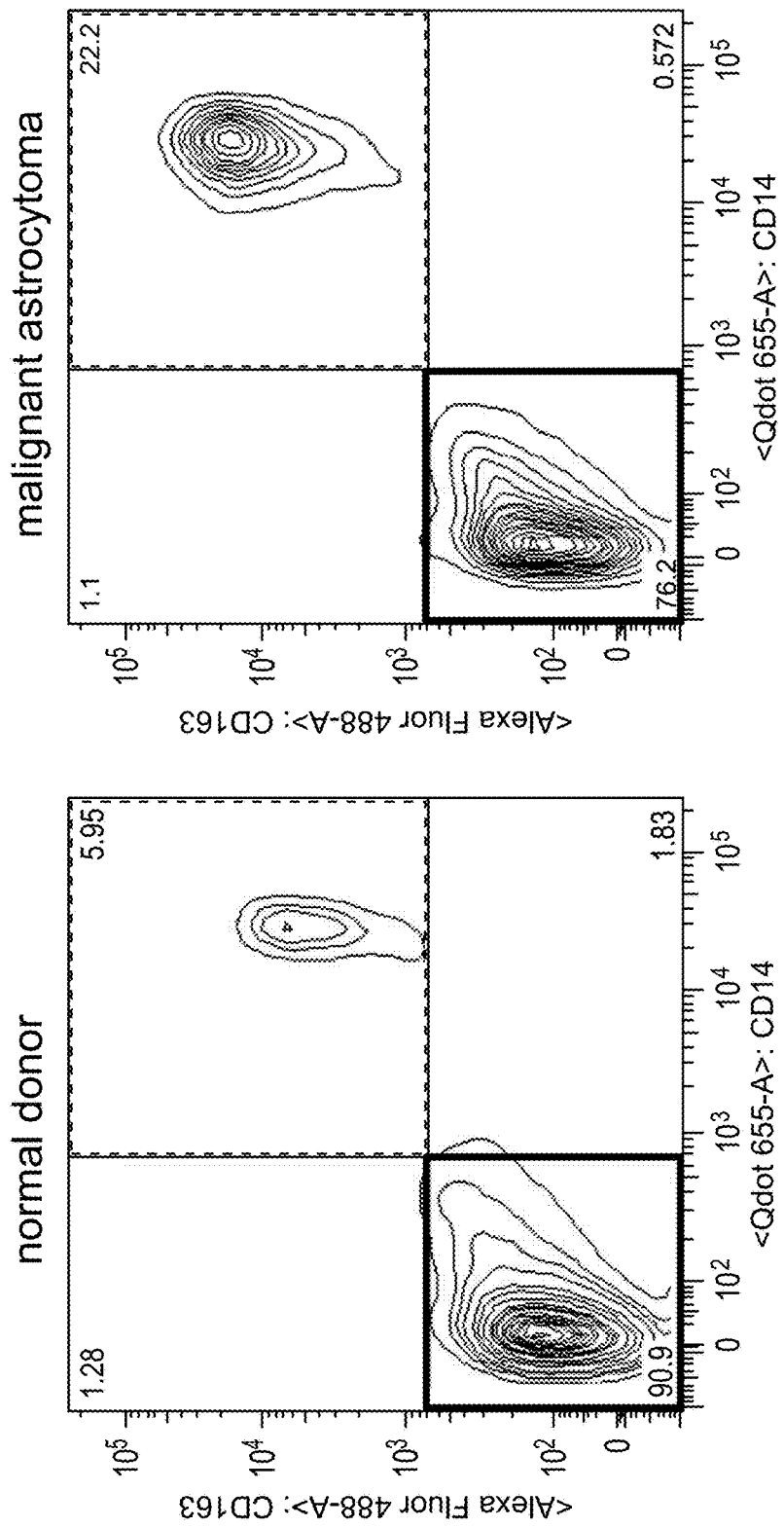
Figure 33C:
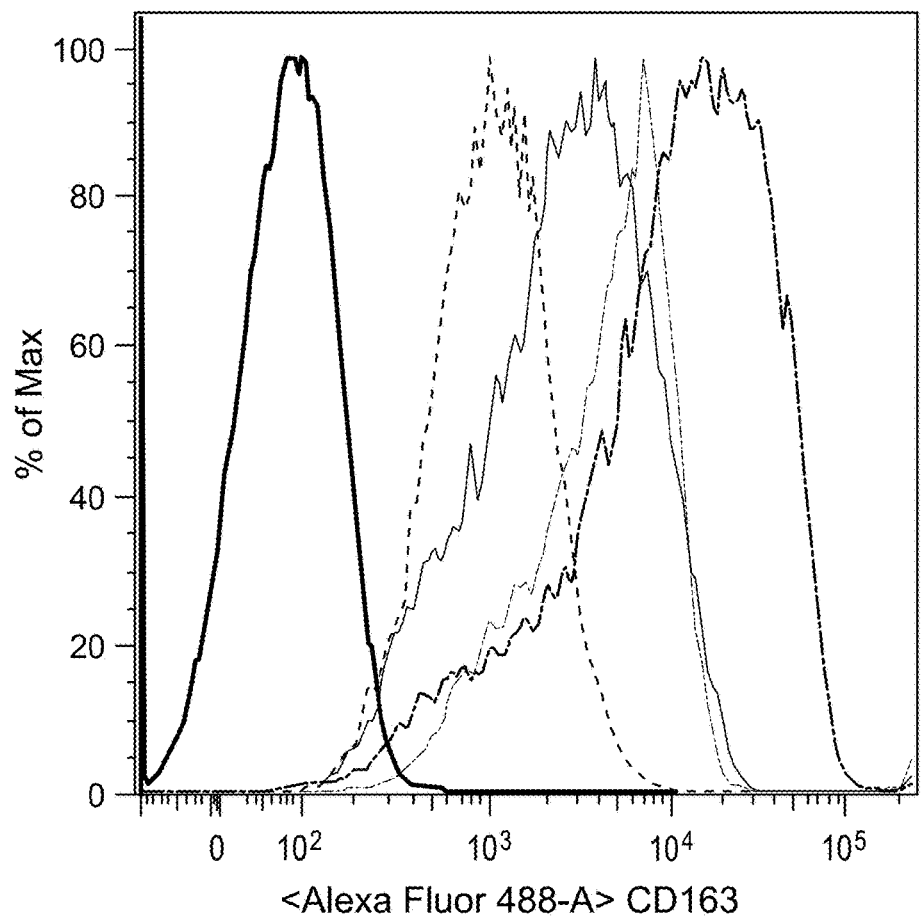

Example 17: Difference in Circulating CD163+ Monocytes Between Normal Individuals and Astrocytoma Patients The difference in circulating CD163+ monocytes between normal individuals and astrocytoma patients was studied. Normal individual showed ~6% CD14+ monocytes in their circulation with intermediate levels of CD163 (FIG. 33A). Two changes are observed in the cancer patient—higher numbers of monocytes and the monocytes have higher levels of CD163 (FIG. 33A). Other cells do not have CD163 at all. Normal individuals can have a wide range of monocytes, due to infections etc. (FIG. 33B, cells positive for CD11b+ CD14) but these are elevated in patients with malignant astrocytomas. The histogram in FIG. 33C shows that patient monocytes have variably higher levels of CD163 on their CD14 monocytes than control cells.

Figure 34A:
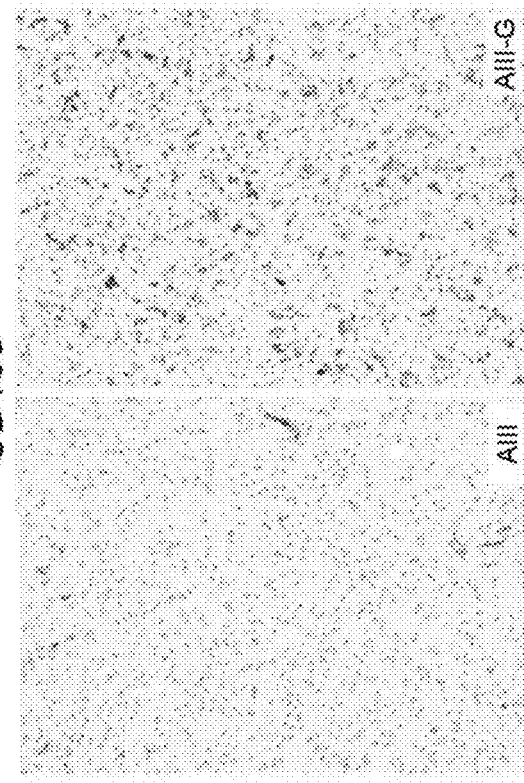
FIG. 34 shows tumor-infiltrating M2 monocytes, wildtype IDH1 status, and gadolinium-enhancement by MRI in anaplastic astrocytoma patients define a more aggressive tumor associated with poor prognosis. Formalin-fixed, paraffin-embedded tissues were stained for the IDHR1 mutation R132H (FIG. 34A) and CD163 (FIG. 34B). Representative images for FLAIR (FIG. 34C and FIG. 34D, left panels) and gadolinium-enhanced T1-weighted axial MRI (FIG. 34C and FIG. 34D, right panels) are shown for non-enhancing, AIII (IDH1 R132H mutant grade III) (FIG. 34C) and enhancing, AIII-G (IDH1 wild-type grade III with characteristics of glioblastoma multiforme) (FIG. 34D) tumors. Patients were divided into groups based on these three aforementioned parameters (FIG. 34A-FIG. 34D), specifically, AIII and AIII-G which resemble more aggressive GBM (FIG. 34E, FIG. 34F, and FIG. 34G). Results for the presence (R132H$^+$) or absence (R132H) of the IDH1 mutation in 38 randomly selected MRI enhancing and non-enhancing AA patients are shown in FIG. 34E where n.d. represents none detected. The CD163$^+$ cell content in excised tumor specimens was enumerated using an automated cell counting system and is presented for AA specimens separated by enhancement in FIG. 34F. Box-and-whisker plots indicate the 75$^{th}$, 50$^{th}$, and 25$^{th}$ percentiles while maximum and minimum data values are represented by the upper and lower whiskers. The statistical significance of the difference between the groups was assessed by the Mann Whitney test (*, p<0.001). The Kaplan-Meier survival curves of patients segregated based on the aggressiveness of their tumors are presented in FIG. 34G. Statistically significant survival differences between the groups () were determined by the Log-Rank (p=0.0019) and Wilcoxon tests (p=0.0088). The results indicate that IDH R132H mutant grade III astrocytomas rarely enhance with gadolinium and that the accumulation of CD163$^+$ M2 cells in tumor tissues is associated with the loss of vascular integrity.
Figure 34B:
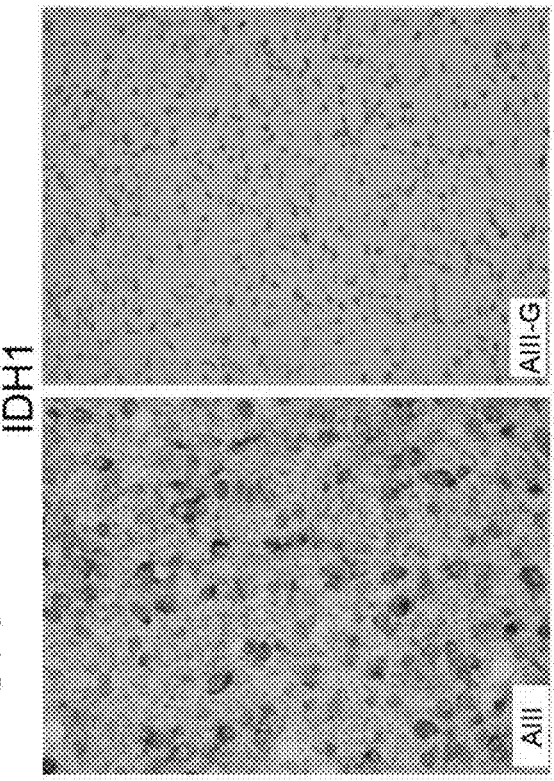
Figure 34F:
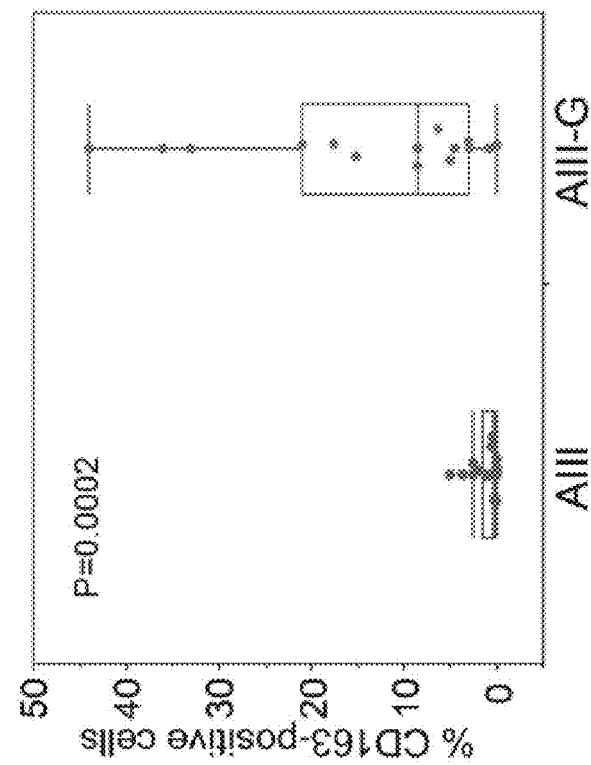
Figure 34E:
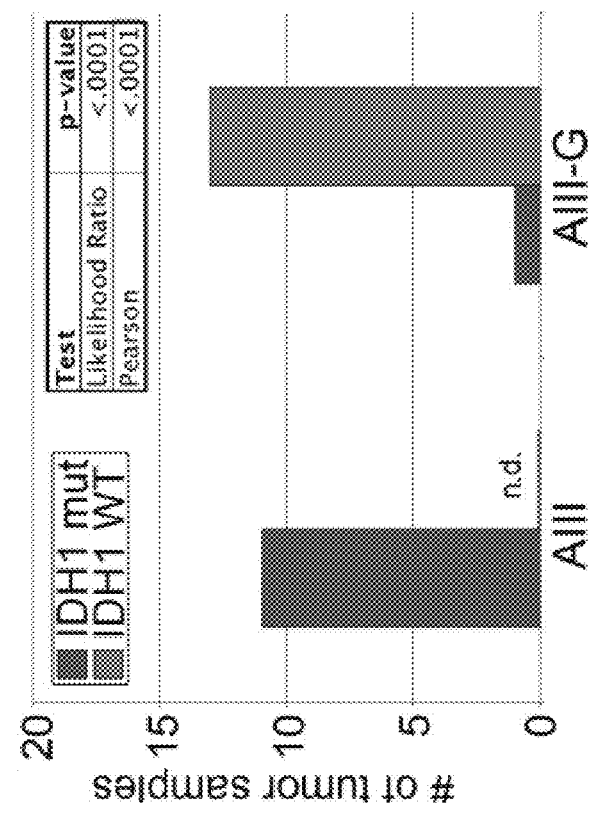
Figure 34G:
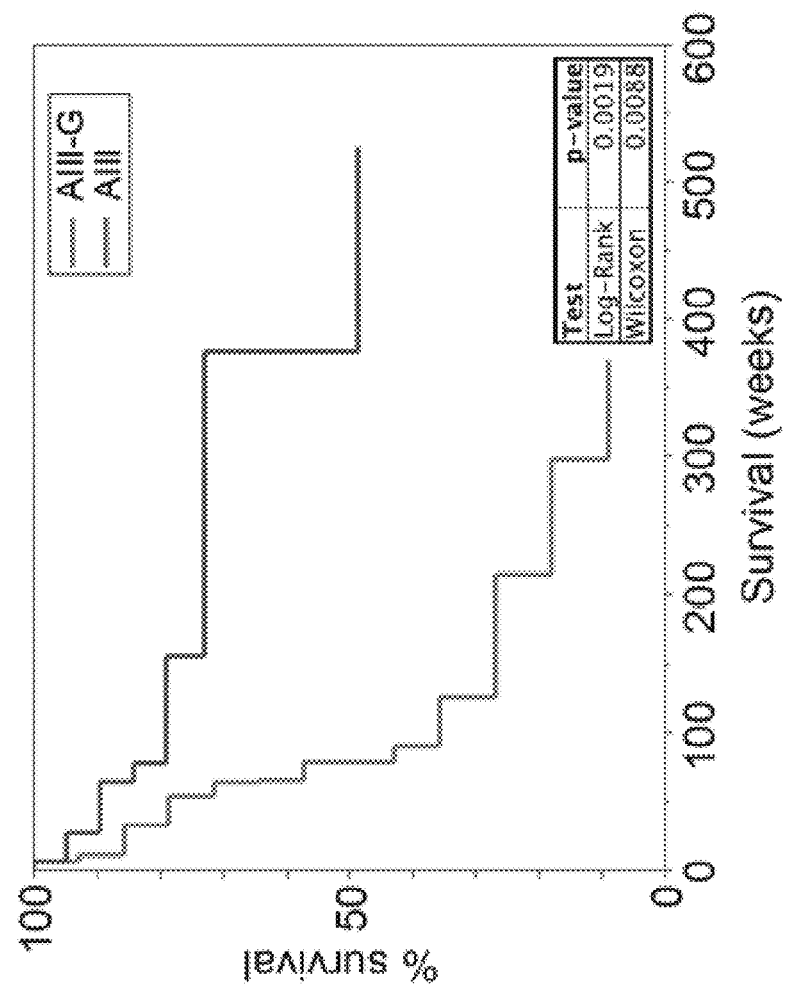

Example 18: Tumor-Infiltrating M2 Monocytes and Wildtype Isocitrate Dehydrogenase (IDH1) Status are Associated with Gadolinium-Enhancement by MRI and Poor Prognosis in Anaplastic Astrocytoma Patients Tumor-infiltrating M2 monocytes, wildtype IDH1 status, and gadolinium-enhancement by MRI in anaplastic astrocytoma patients define a more aggressive tumor associated with poor prognosis. Formalin-fixed, paraffin-embedded tissues were stained for the IDHR1 mutation R132H (FIG. 34A) and CD163 (FIG. 34B). Representative images for FLAIR (FIG. 34C and FIG. 34D, left panels) and gadolinium-enhanced T1-weighted axial MRI (FIG. 34C and FIG. 34D, right panels) are shown for non-enhancing, AIII (IDH1 R132H mutant grade III) (FIG. 34C) and enhancing, AIII-G (IDH1 wild-type grade III with characteristics of glioblastoma multiforme) (FIG. 34D) tumors. Patients were divided into groups based on these three aforementioned parameters (FIG. 34A-FIG. 34D), specifically, AIII and AIII-G which resemble more aggressive GBM (FIG. 34E, FIG. 34F, and FIG. 34G). Results for the presence (R132H$^+$) or absence (R132H$^-$) of the IDH1 mutation in 38 randomly selected MRI enhancing and non-enhancing AA patients are shown in panel FIG. 34E, where n.d. represents none detected. The CD163$^+$ cell content in excised tumor specimens was enumerated using an automated cell counting system and is presented for AA specimens separated by enhancement in FIG. 34F. Box-and-whisker plots indicate the $75^{th}$, $50^{th}$, and $25^{th}$ percentiles while maximum and minimum data values are represented by the upper and lower whiskers. The statistical significance of the difference between the groups was assessed by the Mann Whitney test (*, p<0.001). The Kaplan-Meier survival curves of patients segregated based on the aggressiveness of their tumors are presented in FIG. 34G. Statistically significant survival differences between the groups () were determined by the Log-Rank (p=0.0019) and Wilcoxon tests (p=0.0088). The results indicate that IDH R132H mutant grade III astrocytomas rarely enhance with gadolinium and that, as expected, the accumulation of CD163$^+$ M2 cells in tumor tissues is associated with the loss of vascular integrity.

Example 19: The Numbers of Circulating Monocytes are Elevated in AIII and AIII-G Patients and Express Increasing Levels of the M2 Marker CD163

PBMC from 18 randomly selected WHO grade III astrocytoma patients and 24 normal donors were stained with antibodies specific for CD11b, CD14, and CD163 and assessed by flow cytometry. Forward scatter (FSC) and side scatter (SSC) profiles were used to establish a live cell gate and monocytes were defined as live cells expressing CD11b and CD14 (FIG. 35A). Representative contour plots for the live gate and analysis of CD11b and CD14 positivity in PBMC from a normal and an AA donor are shown in FIG. 35A where axes are presented as log scale and the numbers indicate the frequency of gated cells. FIG. 35B is a summary chart showing the frequency of CD11b$^+$CD14$^+$ monocytes in PBMC from 12 patients with AIII, 6 patients with AIII-G, and 24 normal individuals determined by flow cytometry. The statistical significance of differences in cell percentages between normal individuals and AA patient subsets was assessed by Student's t test (, p<0.01). The median fluorescence intensity (MFI) for CD163 staining of CD11b+ CD14+ gated monocytes is overlayed from representative histogram plots of AIII, AIII-G, and normal blood specimens in FIG. 35C. Axes are presented as log scale. The MFI for CD163-staining of the gated monocyte subset in PBMC samples from the different donor groups are presented in FIG. 35D. Statistical significance was assessed by ANOVA followed by Tukey's post-test (, p<0.05). While CD11b+ CD14$^+$ monocytes are present at similarly elevated levels in the circulation of all of the tested patients, cells from the circulation of patients with the AIII tumors more closely resembling GBM (Glioblastoma multiforme; AIII-G) express progressively higher levels of CD163 than those from patients with less malignant AIII tumors and normal subjects (FIG. 35C and FIG. 35D). As expected due to the increase in circulating monocytes, the frequencies of CD3$^+$ and CD20$^+$ lymphocytes are decreased in the blood of grade III astrocytoma patients by comparison with normal individual.

Figure 36A:
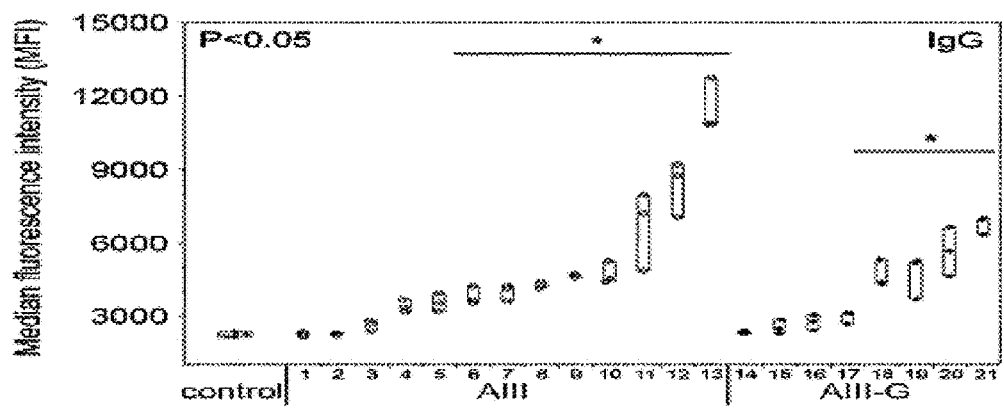
FIG. 36 shows that antibodies present in AIII and AIII-G patient serum that bind shared antigens on astrocytoma exosomes differ in isotype profile. Exosomes, isolated from three astrocytoma patient primary tumor cell lines were coated onto 96-well plates and incubated with patient sera (13 AIII, 8 AIII-G) collected before initial surgery and normal control serum (4). Bound antibodies were detected with fluorescently-conjugated whole IgG (FIG. 36A) or secondary antibodies specific for IgG isotypes (FIG. 36B) and the extent of antibody binding measured as MFI.
Figure 36B:
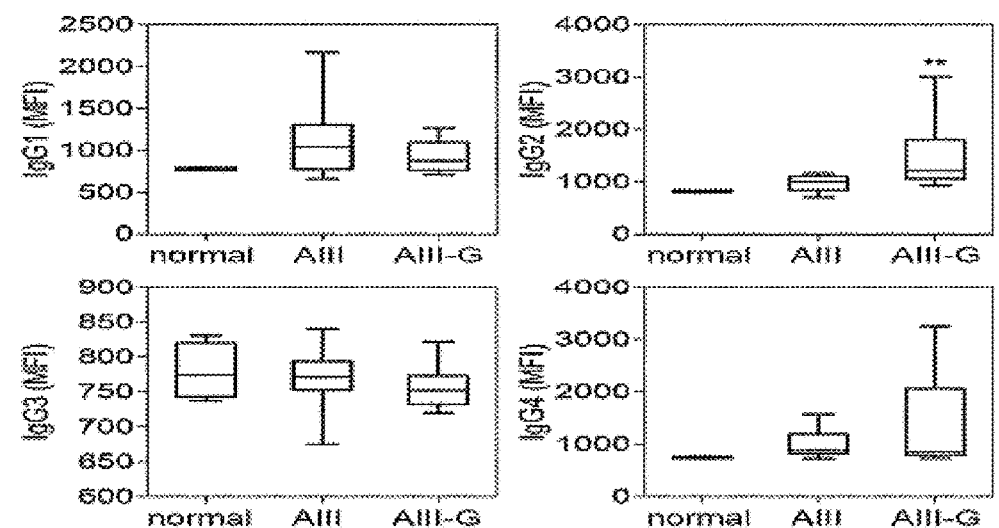

Example 20: Antibodies Present in AIII and AIII-G Patient Serum that Bind Shared Antigens on Astrocytoma Exosomes Differ in Isotype Profile Exosomes isolated from three astrocytoma patient primary tumor cell lines were coated onto 96-well plates and incubated with patient sera (13 AIII, 8 AIII-G) collected before initial surgery and normal control serum (4). Bound antibodies were detected with fluorescently-conjugated whole IgG (FIG. 36A) or secondary antibodies specific for IgG isotypes (FIG. 36B) and the extent of antibody binding measured as MFI. The data is presented as values from individual subjects in box-and-whisker plots as described in Example 18. The asterisks and bars in FIG. 36A indicate values that are significantly different from normal control values as determined by ANOVA followed by Dunnett's test (p<0.05). In FIG. 36B, the group of values from AIII-G patients that statistically differed significantly from normal control and AIII patient values by ANOVA and Tukey's post-test is noted by **(p=0.004). As shown in FIG. 36A, IgG antibodies reactive with these exosomes are also present in sera from the majority of grade III astrocytoma patients regardless of their prognostic category. However, when isotype specific antibodies were used for detection we observed that exosome-binding antibodies of the Th2-associated IgG2 isotype were significantly elevated in AIII-G by comparison with the longer-lived AIII patients (FIG. 36B). Levels of IgG1 tended to be slightly elevated in the latter patients while levels of IgG4 were slightly elevated in AIII-G patients but neither of these differences was significant.

Figure 37:
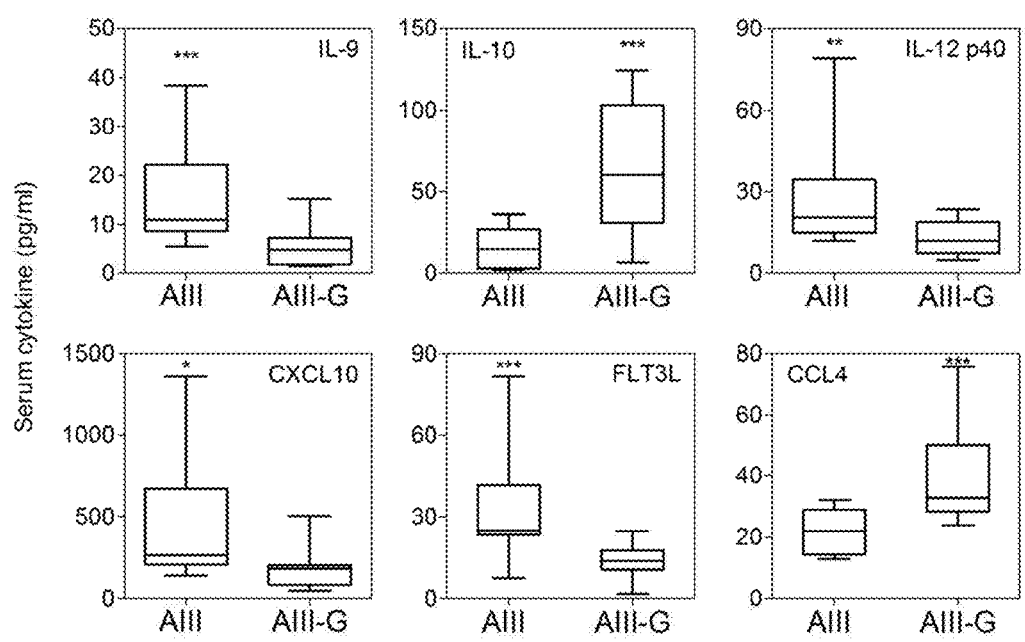
FIG. 37 shows that soluble factors generally associated with Th1 and Th2 immunity are elevated in the sera of AIII and AIII-G patients respectively.

Example 21: Soluble Factors Generally Associated with Th1 and Th2 Immunity are Elevated in the Sera of AIII and AIII-G Patients Respectively Sera from AA patients segregated based on gadolinium-enhanced MRI into AIII (n=17) and AIII-G (n=13) subsets was assessed for the levels of soluble factors by Luminex. Concentrations for individual specimens are presented in box-and-whisker plots as described in Example 18. The statistical significance of differences between the two groups was assessed by Student's t test **, p≤0.001; , p≤0.01; *, p≤0.05. Serum concentrations of the Th2 cytokine IL-10 and CCL4 were significantly elevated in patients with AIII tumors having GBM characteristics whereas IL-9 and the Th1-related IL-12 P40, CXCL10, and FLT3L were significantly elevated in the remaining AIII patients (FIG. 37).

Example 22: Levels of Expression in PBMC of Genes Encoding White Blood Cell Phenotypic Markers, Cytokine and Chemokine Receptors as Well as their Ligands Differ Between AIII and AIII-G Patients The copy numbers of genes for monocyte phenotypic markers (FIG. 38A), interleukins (FIG. 38B), interleukin receptors (FIG. 38C), CC chemokines (FIG. 38D) and receptors (FIG. 38E), and CXC chemokines (FIG. 38F) and receptors (FIG. 38G) in PBMC from 17 unselected AA patients were assessed by high throughput quantitative RT-PCR and normalized to the copy numbers of the housekeeping gene L13a present in each sample. LDA was performed on the normalized copy numbers and is presented in the left-hand panels where each dot represents data from an individual patient. Dots representing the results of analysis of individual AIII and AIII-G patients are colored blue and red respectively. The multivariate mean for each group is presented as the + at the center of similarly colored circles/ellipses representing the 95% confidence intervals of the means. Mean copy numbers for each gene tested in the two patient cohorts are presented in the accompanying right-hand panels as heatmaps with red and green corresponding to high versus low expression levels respectively and the range of gene copy numbers detected shown in the associated scale bars. Grey boxes represent reactions that failed to generate a detectable product.

Figure 38A:
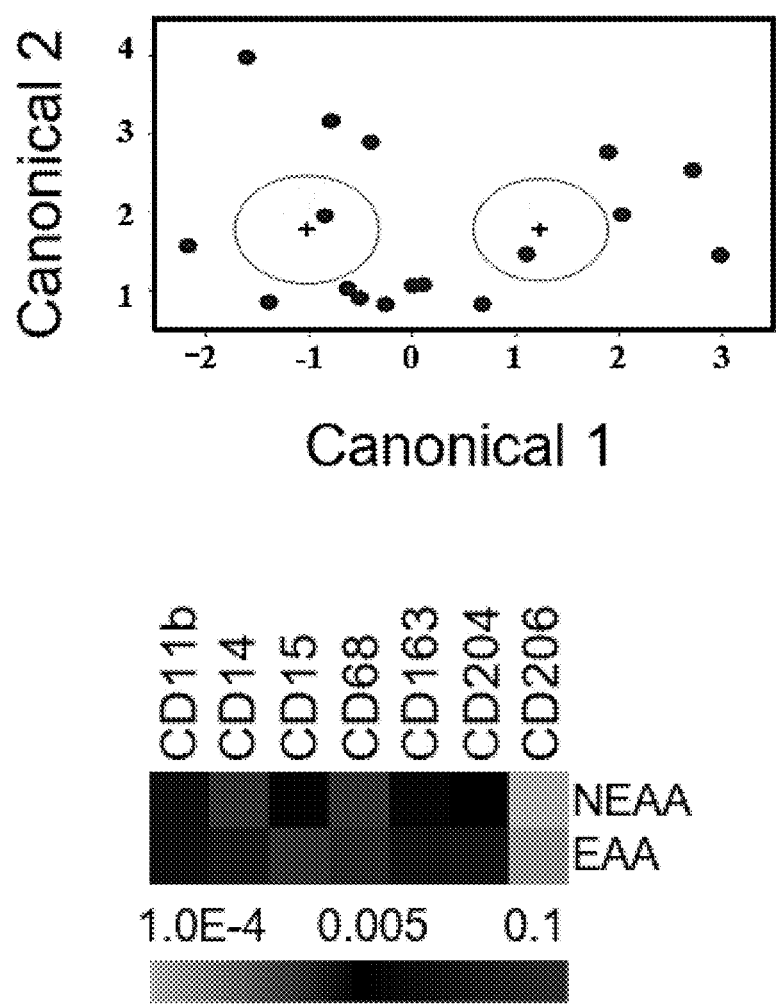
FIG. 38 shows that levels of expression in PBMC of genes encoding white blood cell phenotypic markers, cytokine and chemokine receptors as well as their ligands differ between AIII and AIII-G patients. The copy numbers of genes for monocyte phenotypic markers (FIG. 38A), interleukins (FIG. 38B), interleukin receptors (FIG. 38C), CC chemokines (FIG. 38D) and receptors (FIG. 38E), and CXC chemokines (FIG. 38F) and receptors (FIG. 38G) in PBMC from 17 unselected AA patients were assessed by high throughput quantitative RT-PCR and normalized to the copy numbers of the housekeeping gene L13a present in each sample.
Figure 38B:
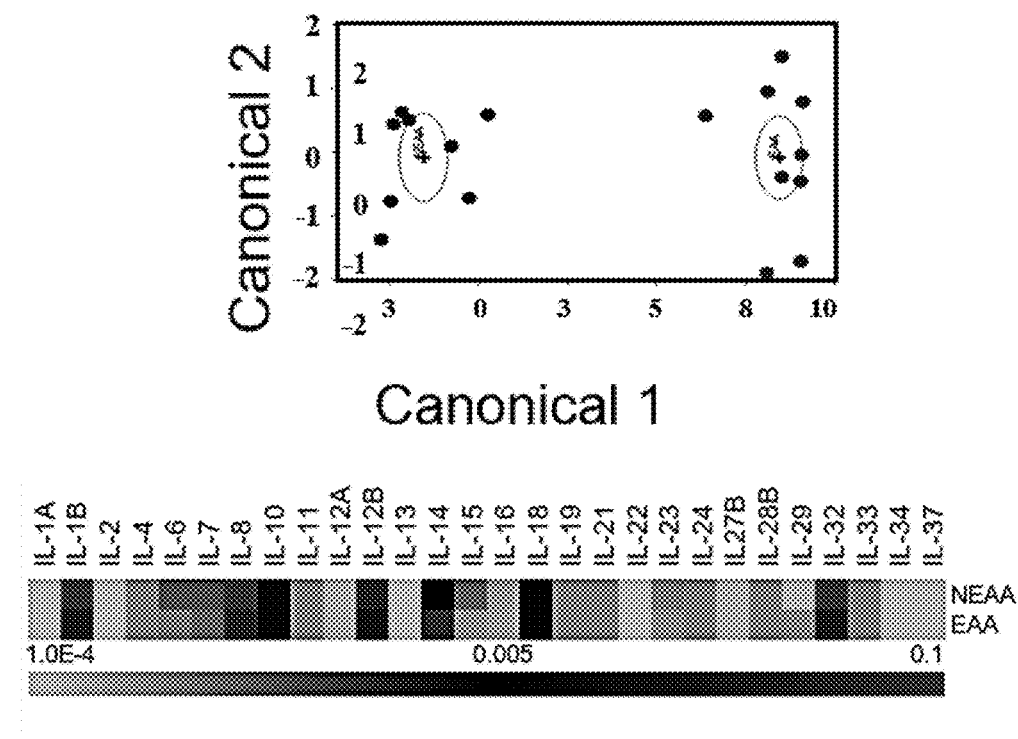
Figure 38C:
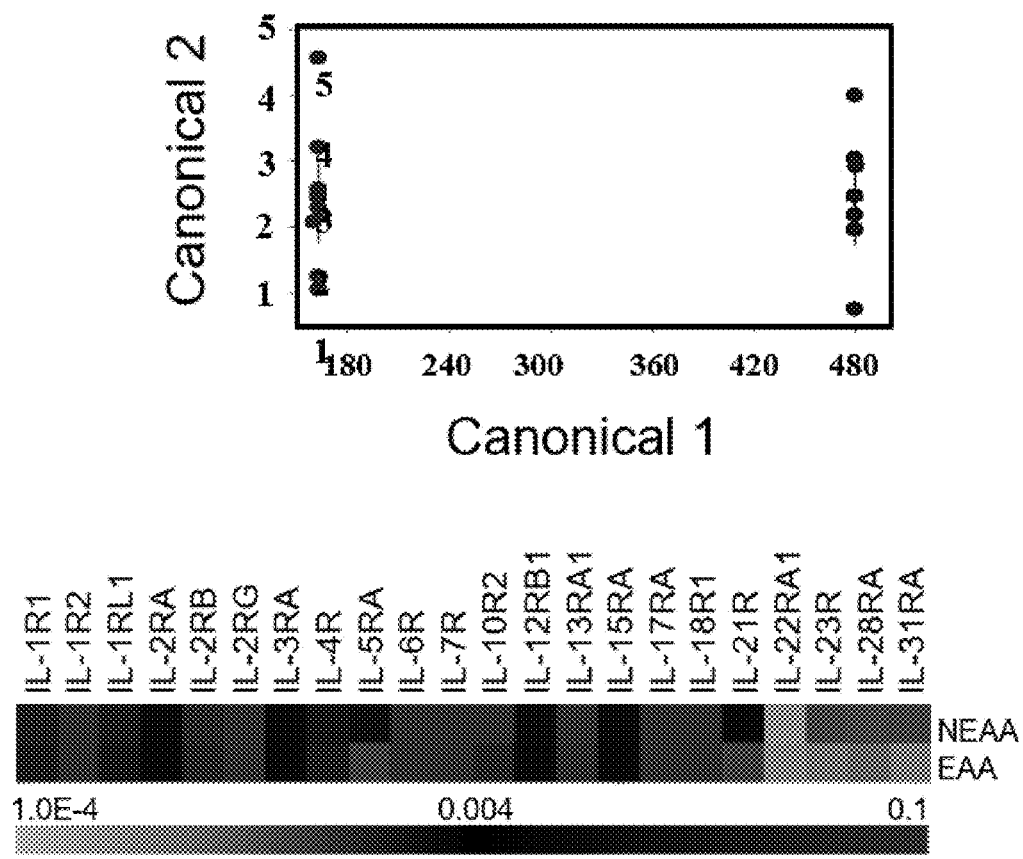
Figure 38D:
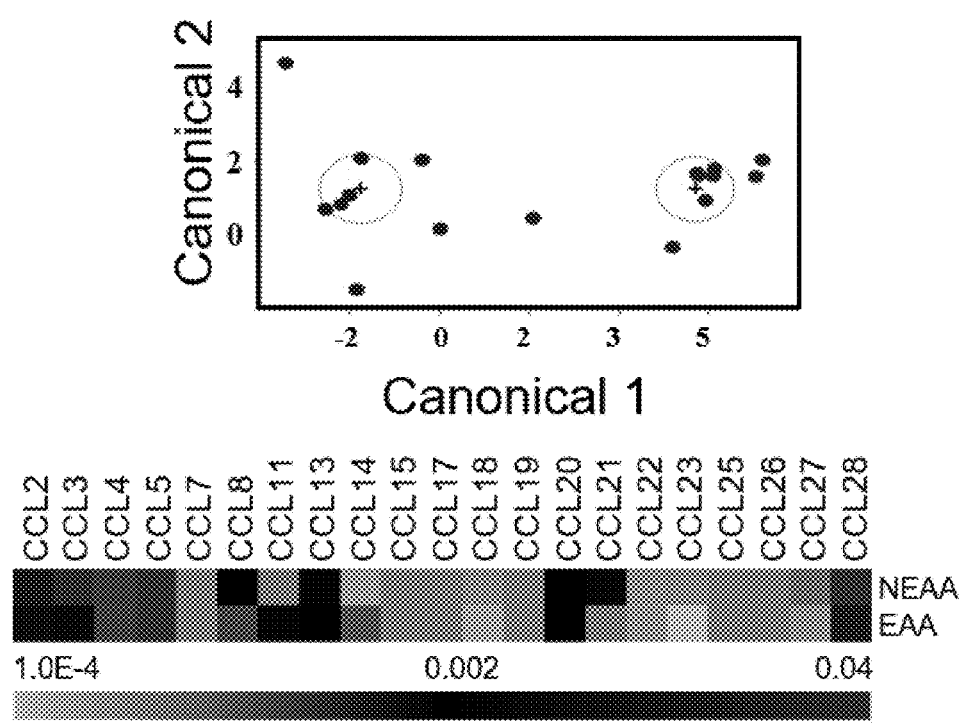
Figure 38E:
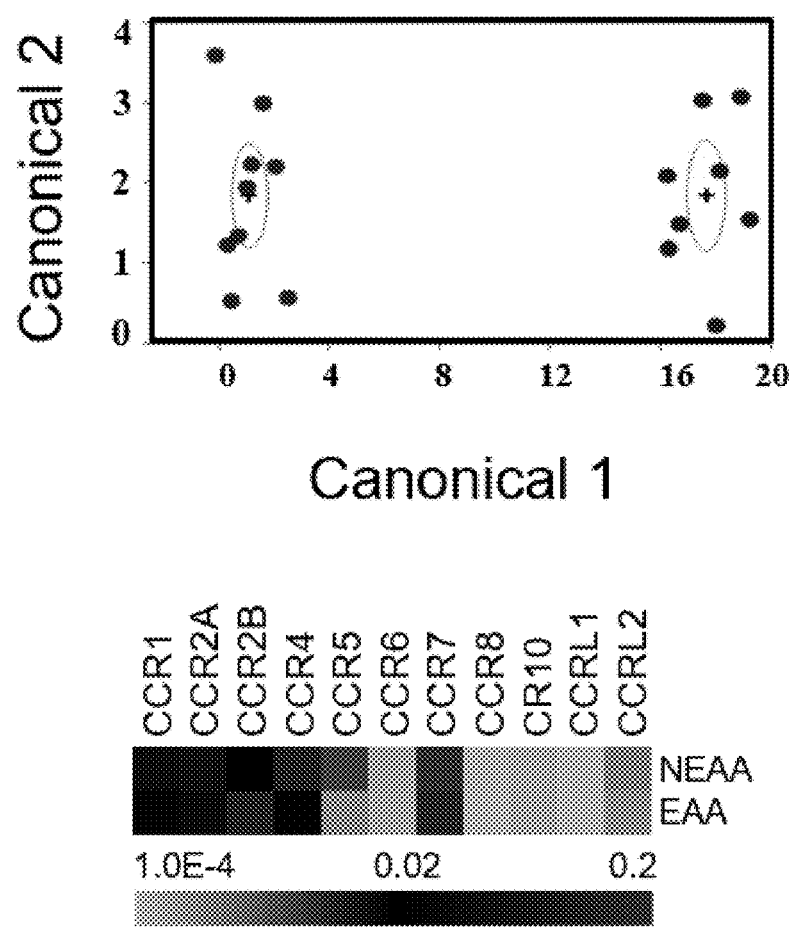
Figure 38F:
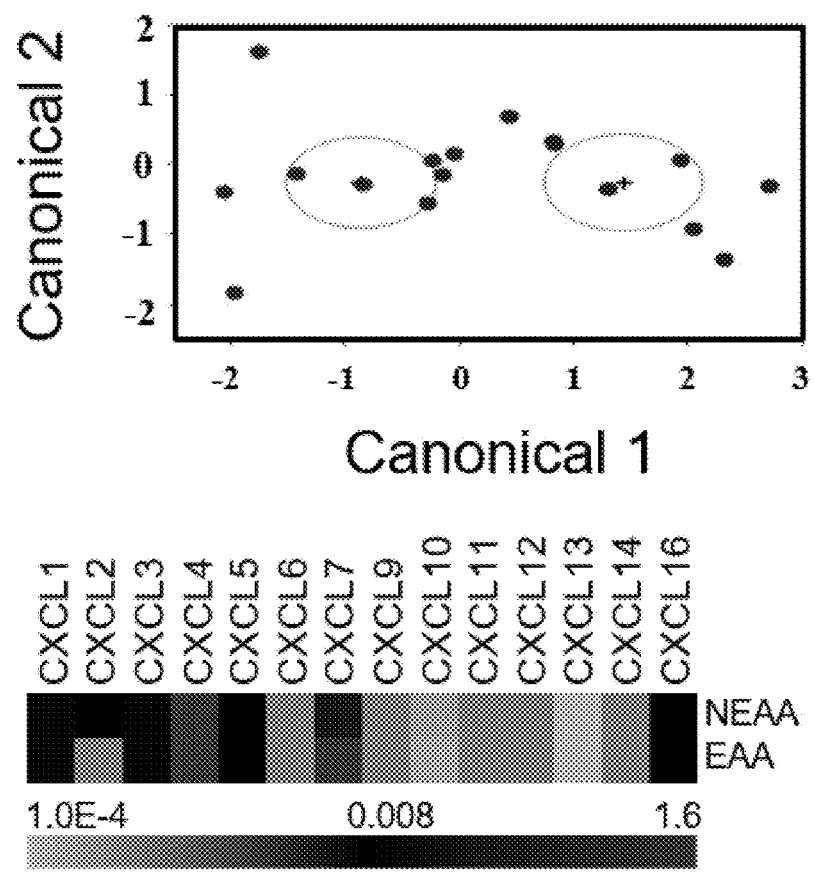
Figure 38G:
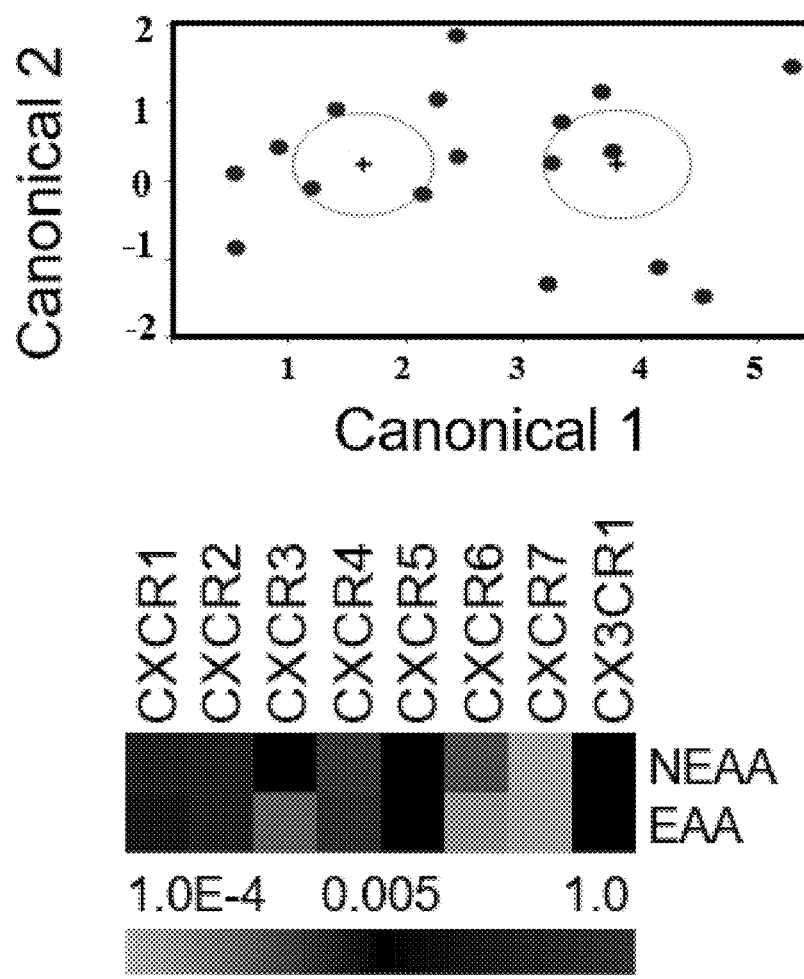

Linear discriminant analysis (LDA) was used to determine how well the expression of each marker class separates and characterizes the two patient cohorts. FIG. 38A shows the results of LDA for the monocyte phenotypic markers CD11b, CD14, CD15, CD68, CD163, CD204, and CD206 with the corresponding gene expression levels depicted as heat maps. Moderate to strong elevations in the expression levels of mRNAs specific for CD15, CD163 and CD206 (8, 3, 5 times, respectively) in PBMC samples from patients with AIII-G were observed by comparison with conventional AIII tumors but slightly elevated CD11b and CD204 transcript levels in the latter (1.9 fold). LDA analysis of the levels of expression of monocyte phenotype genes accurately separated 14 of the 17 cases tested into one of the two patient cohorts. Consistent with the flow cytometry data, CD163 proved to be the most discriminatory phenotypic mRNA marker. Similar LDA performed for 28 interleukin genes correctly classified 100% of the patients into their appropriate cohorts despite the fact that only the type 1-associated cytokines IL-15 and IL-32 were significantly different between the AIII and AIII-G samples (p=0.0111 and p=0.0152, respectively), both being lower in the latter (FIG. 38B). Other genes were either not expressed or expressed at levels that did not significantly differ. Analysis of the signatures of 22 interleukin receptor gene mRNAs in PBMC also clearly discriminated between AIII and AIII-G patients (FIG. 38C). Where differentially expressed, the transcripts of most of these genes were lower in AIII-G by comparison with AIII PBMC. IL-23R and IL31RA in particular were expressed at significantly higher levels in the AIII samples (p=0.0055 and p=0.0360, respectively). LDA of the mRNA levels of the 15 out of 21 CCL genes expressed in PBMC at sufficient levels for this analysis also differentiated the two patient cohorts (FIG. 38D). A trend for elevated expression was detected in the AIII samples for CCL3, CCL8, CCL13, CCL21, CCL23 and CCL28 genes, and in the AIII-G samples for CCL2, CCL11 and CCL14 genes. However, with the available samples, statistically significant differences were only obtained for CCL3 mRNA, which was present at higher levels in AIII by comparison with AIII-G PBMC. LDA of CCR gene expression data also clearly differentiated the patients (FIG. 38E). For most CCR mRNAs, except for CCR4 which was somewhat higher in AIII-G samples, there was a trend for higher expression in the conventional AIII samples, but only two genes, CCR1 and CCR5 were significantly overexpressed (p=0.0206 and p=0.0003, respectively). LDA of the CXCL gene expression data accurately characterized 15 of the 17 cases tested as belonging to the different patient cohorts despite no statistically significant differences in mRNA levels (FIG. 38F). A difference close to significance was detected for only CXCL7 (p=0.0673), which was upregulated in PBMC from AIII-G patients. CXCL2, CXCL10, and CXCL16 transcripts were detected at higher levels in conventional AIII PBMC but the differences with AIII-G samples were not significant. Comparable results were obtained for LDA based on the expression of CXC chemokine receptors where 14 of the 17 AA cases were accurately subgrouped (FIG. 38G). CXCR1, CXCR3, CXCR4, CXCR6, and CX3CR1 transcripts were found to be overexpressed in AIII-G, but only CXCR3 and CXCR6 by significant levels (p=0.0111 and p=0.0206, respectively). Only CXCR7 mRNA levels were higher in PBMC from patients with conventional AIII tumors but the difference did not reach statistical significance with the number of samples analyzed.

Figure 39B:
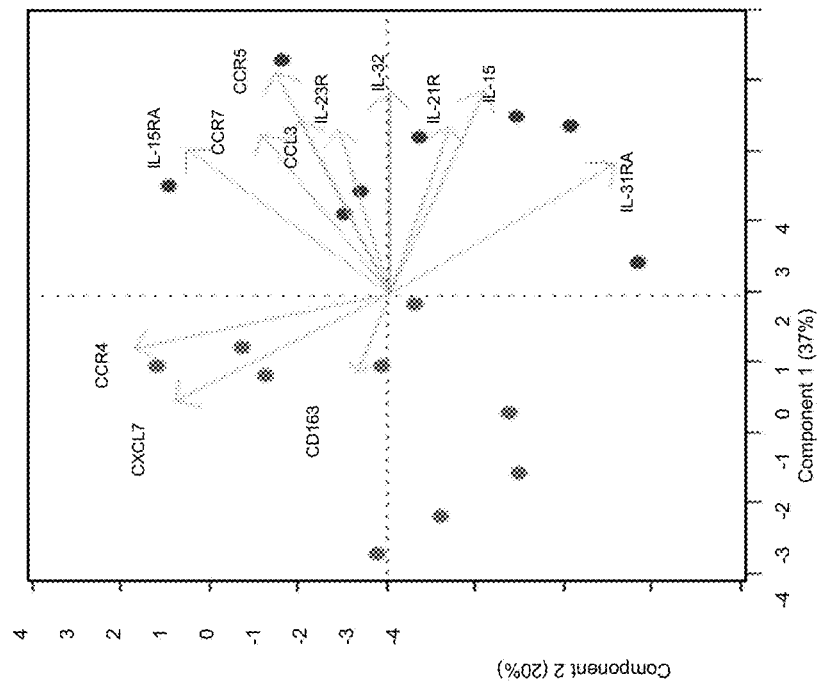
FIG. 39 shows that AIII and AIII-G patient subsets can be accurately differentiated by the expression of select immunologically-relevant genes in PBMC. Discriminant analysis was first used to identify the gene expression data that best separated AIII and AIII-G patient PBMC (FIG. 39A). Principal Component Analysis was then used to determine which of these genes, CCL3, CCR4, CCR5, CCR7, CXCL7, IL-15, IL-32, IL-15R, IL-21R, IL-23R, IL-31RA, and CD163, are most effective at differentiating the two patient cohorts (FIG. 39B).
Figure 39A:
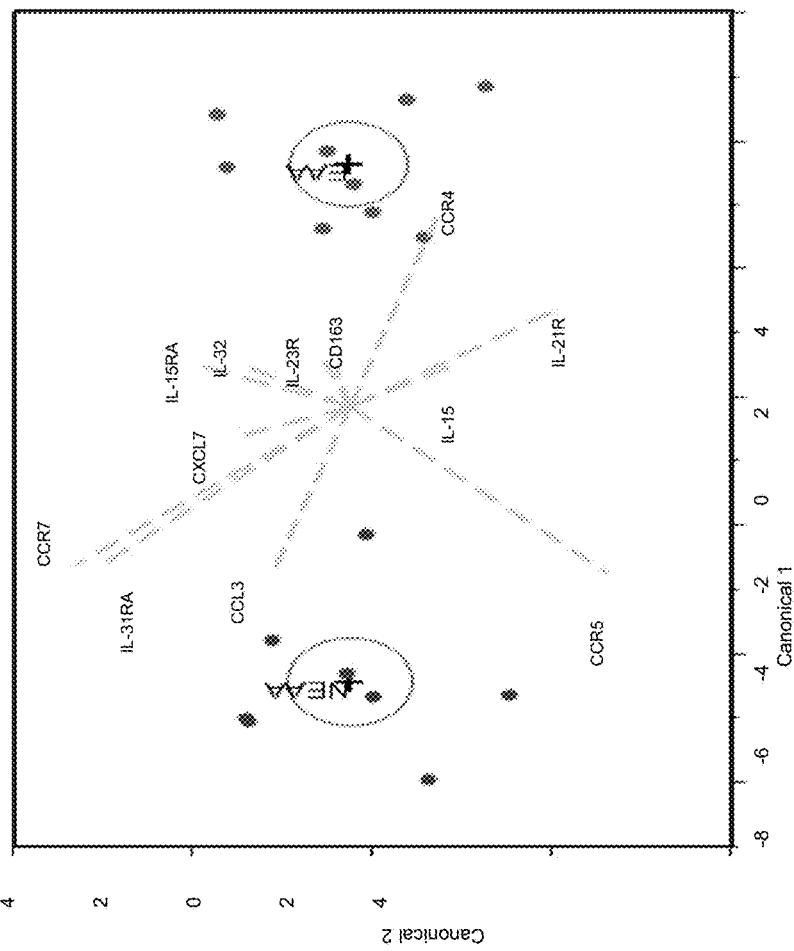

Example 23: AIII and AIII-G Patient Subsets can be Accurately Differentiated by the Expression of Select Immunologically-Relevant Genes in PBMC Discriminant analysis was first used to identify the gene expression data, obtained as described in Example 22, that best separated AIII and AIII-G patient PBMC (FIG. 39A). Principal Component Analysis was then used to determine which of these genes, CCL3, CCR4, CCR5, CCR7, CXCL7, IL-15, IL-32, IL-15R, IL-21R, IL-23R, IL-31RA, and CD163, are most effective at differentiating the two patient cohorts (FIG. 39B). Both discriminant and principal component plots were generated using gene-specific expression profiles for each individual AIII and AIII-G PBMC specimen (represented by dots, colored blue and red, respectively). The dashed green lines in (FIG. 39A) and green vectors in (FIG. 39B) represent the directions of the gene transcripts in the canonical and component spaces respectively. LDA was performed on the mRNA levels of all 93 genes with detectable signals from PBMC to identify the genes that most reliably delineate AIII from AIII-G patients (FIG. 39A). The twelve genes detailed in Table 9 were selected for PCA analysis (FIG. 39B). The total variance explained by the first principal component was 37% whereas the second principal component explained nearly 20% of total variance. Based on PCA, assessment of the expression levels in PBMC of the M2 marker CD163, the proinflammatory cytokine IL-32, and the type 1 cytokine receptors IL-21R and IL-23R are sufficient to obtain clear separation between patients with the different classes of AIII tumors

TABLE 9

Functional characteristics of PBMC-expressed genes selected by Discriminant Analysis.

| Gene Symbol | Functional Annotation | Cell Expression | Immune-related Functions in Circulation |
|---|---|---|---|
| CCL3 | Inducible, secreted chemokine ligand for CCR1, CCR3, CCR5 | Leukocytes | Activation of cell chemotaxis, trafficking and phagocytosis of PBMC by ligand-receptor interaction |
| CCR4 | Chemokine receptor for CCL17, CCL22 ligands | Th2-, T-reg-cells | Activation of Th2 response by G protein coupled receptor signaling |
| CCR5 | Chemokine receptor for CCL3 CCL4, CCL5, CCL8 | T-cells, monocytes | Activation of Th1 response by G protein coupled receptor signaling |
| CCR7 | Chemokine receptor for CCL19, CCL21 | B-, T-, dendritic cells | Homing, migration, induction and maintenance of PBMC by G protein coupled receptor signaling |
| CXCL7 | Inducible, secreted chemokine ligand for CXCR, CXCR2 | Platelets, macrophages | Chemotaxis and activation of neutrophils and macrophages by ligand-receptor interaction |
| IL-15 | Inducible, secreted cytokine or IL2/IL15 receptor complex | Monocytes, dendritic cells | Activation of differentiation and proliferation of PBMC |
| IL-32 | Intracellular and secreted inducer of inflammatory cytokines | T-, NK-cells | Control of PBCs activation and differentiation |
| IL-15R | Cytokine receptor for IL-15 | Monocytes, NK, T, NKT-cells | Presentation of IL-15 for intracrine, autocrine, paracrine activation of PBMC |
| IL-21R | Cytokine receptor for IL-21 | B, T, NK-cells | Activation of PBMC by ligand-21R/IL-2R, IL-21R/IL-7R, IL-21R/IL-15RA interaction |
| IL-23R | Cytokine receptor for IL-23 | Leukocytes | Activation of T, NK and dendritic cells by ligand-IL-23R/IL-12RB1 interaction |
| IL-31RA | Cytokine receptor for IL-31 | Monocytes, T-cells | Receptor signaling via STAT-3, STAT-5 activation in monocytes and T-cell subsets |
| CD163 | Scavenger receptor | Monocytes, macrophages | Regulation of Th2-cell differentiation, clearance of substances by receptor mediated endocytosis |

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present disclosure is not entitled to antedate such publication by virtue of prior disclosure.

What is claimed is:

1. An immunogenic diffusion chamber, the chamber comprising irradiated tumor cells and irradiated Insulin-like Growth Factor-1 Receptor antisense oligodeoxynucleotide (IGF-1R AS ODN), wherein the IGF-IR AS ODN has the sequence of SEQ ID NO: 1.

2. The immunogenic diffusion chamber of claim 1, wherein the chamber comprises 2 µg of the IGF-1R AS ODN.

3. A method for preparing a diffusion chamber for implantation into a subject suffering from a tumor, the method comprising:
   a) treating tumor cells from the subject ex vivo with a first amount of an IGF-1R AS ODN, wherein the IGF-IR AS ODN has the sequence of SEQ ID NO: 1;
   b) washing the tumor cells to remove the first amount of the IGF-1R AS ODN;
   c) placing the tumor cells and a second amount of the IGF-1R AS ODN in the diffusion chamber; and
   d) irradiating the tumor cells and the second amount of the IGF-1R AS ODN in the diffusion chamber.

4. The method of claim 3, wherein the tumor cells and the second amount of the IGF-1R AS ODN are irradiated with gamma radiation.

5. The method of claim 4, wherein the tumor cells and the second amount of the IGF-1R AS ODN are irradiated with up to about 15 Gy of gamma radiation.

6. The method of claim 5, wherein the tumor cells and the second amount of the IGF-1R AS ODN are irradiated with about 1 Gy, about 2 Gy, about 4 Gy, about 5 Gy, about 6 Gy, or about 10 Gy of gamma radiation.

7. The method of claim 6, wherein the cells are irradiated with about 5 Gy of gamma radiation.

8. The method of claim 3, wherein the cells are irradiated at least twice, at least three times, at least four times, or at least five times.

9. The method of claim 3, wherein washing the tumor cells eliminates any trace of the first amount of the IGF-1R AS ODN.

10. The method of claim 3, wherein the tumor cells from the subject are treated ex vivo for 3 to 48 hours.

11. A method for inducing an anti-tumor immune response in a subject in need thereof, the method comprising implanting a diffusion chamber into the subject for a therapeutically effective time, wherein the diffusion chamber is prepared by:
   a) treating tumor cells from the subject ex vivo with a first amount of an IGF-1R AS ODN, wherein the IGF-IR AS ODN has the sequence of SEQ ID NO: 1;
   b) washing the tumor cells to remove the first amount of the IGF-1R AS ODN;
   c) placing the tumor cells and a second amount of the IGF-1R AS ODN in the diffusion chamber; and
   d) irradiating the tumor cells and the second amount of the IGF-1R AS ODN in the diffusion chamber.

12. The method of claim 11, wherein the tumor cells and the second amount of the IGF-1R AS ODN are irradiated with gamma radiation.

13. The method of claim 12, wherein the tumor cells and cells and the second amount of the IGF-1R AS ODN are irradiated with up to about 15 Gy of gamma radiation.

14. The method of claim 13, wherein the cells are irradiated with about 1 Gy, about 2 Gy, about 4 Gy, about 5 Gy, about 6 Gy, or about 10 Gy of gamma radiation.

15. The method of claim 14, wherein the cells are irradiated with about 5 Gy of gamma radiation.

16. The method of claim 11, wherein the cells are irradiated at least twice, at least three times, at least four times, or at least five times.

17. The method of claim 11, wherein washing the tumor cells eliminates any trace of the first amount of the IGF-1R AS ODN.

18. The method of claim 11, wherein the tumor cells from the subject are treated ex vivo for 3 to 48 hours.

19. The method of claim 11, wherein the subject is suffering from at least one of glioma, astrocytoma, breast cancer, head and neck squamous cell cancer, papillary renal cell carcinoma Type II, lung cancer, pancreatic cancer, gall bladder cancer, rectal cancer, classical Hodgkin's lymphoma, ovarian cancer, or colorectal cancer.

20. The method of claim 19, wherein the subject is suffering from glioma.

21. The method of claim 20, wherein the anti-tumor immune response induces regression of the glioma in the subject.

22. The method of claim 11, wherein the diffusion chamber is implanted into the abdomen of the subject.

23. The method of claim 22, wherein the diffusion chamber is implanted into the rectus sheath of the subject.

24. The method of claim 11, wherein the method further comprises systemically administering to the subject an effective amount of a pharmaceutical composition comprising the IGF-1R AS ODN.

* * * * *

SEQUENCE LISTING

<160> NUMBER OF SEQ ID NOS: 19

<210> SEQ ID NO 1
<211> LENGTH: 18
<212> TYPE: DNA
<213> ORGANISM: Artificial Sequence
<220> FEATURE:
<223> OTHER INFORMATION: NOBEL phosphorothioate AS ODN
<220> FEATURE:
<221> NAME/KEY: misc_feature
<222> LOCATION: (1)..(18)
<223> OTHER INFORMATION: May be joined by a phosphorothioate linkage

<400> SEQUENCE: 1
tcctccggag ccagactt                                          18

<210> SEQ ID NO 2
<211> LENGTH: 17
<212> TYPE: DNA
<213> ORGANISM: Artificial Sequence

```
<220> FEATURE:
<223> OTHER INFORMATION: Recombinant Insulin-like Growth Factor Receptor
      (IGF-1R) antisense oligodeoxynucleotide (AS-ODN)

<400> SEQUENCE: 2
ttctccactc gtcggcc                                                    17

<210> SEQ ID NO 3
<211> LENGTH: 18
<212> TYPE: DNA
<213> ORGANISM: Artificial Sequence
<220> FEATURE:
<223> OTHER INFORMATION: Recombinant Insulin-like Growth Factor Receptor
      (IGF-1R) antisense oligodeoxynucleotide (AS-ODN)

<400> SEQUENCE: 3
acaggccgtg tcgttgtc                                                   18

<210> SEQ ID NO 4
<211> LENGTH: 18
<212> TYPE: DNA
<213> ORGANISM: Artificial Sequence
<220> FEATURE:
<223> OTHER INFORMATION: Recombinant Insulin-like Growth Factor Receptor
      (IGF-1R) antisense oligodeoxynucleotide (AS-ODN)

<400> SEQUENCE: 4
gcactcgccg tcgtggat                                                   18

<210> SEQ ID NO 5
<211> LENGTH: 18
<212> TYPE: DNA
<213> ORGANISM: Artificial Sequence
<220> FEATURE:
<223> OTHER INFORMATION: Recombinant Insulin-like Growth Factor Receptor
      (IGF-1R) antisense oligodeoxynucleotide (AS-ODN)

<400> SEQUENCE: 5
cggatatggt cgttctcc                                                   18

<210> SEQ ID NO 6
<211> LENGTH: 18
<212> TYPE: DNA
<213> ORGANISM: Artificial Sequence
<220> FEATURE:
<223> OTHER INFORMATION: Recombinant Insulin-like Growth Factor Receptor
      (IGF-1R) antisense oligodeoxynucleotide (AS-ODN)

<400> SEQUENCE: 6
tctcagcctc gtggttgc                                                   18

<210> SEQ ID NO 7
<211> LENGTH: 18
<212> TYPE: DNA
<213> ORGANISM: Artificial Sequence
<220> FEATURE:
<223> OTHER INFORMATION: Recombinant Insulin-like Growth Factor Receptor
      (IGF-1R) antisense oligodeoxynucleotide (AS-ODN)

<400> SEQUENCE: 7
ttgcggcctc gttcactg                                                   18

<210> SEQ ID NO 8
<211> LENGTH: 18
<212> TYPE: DNA
<213> ORGANISM: Artificial Sequence
<220> FEATURE:
```

<223> OTHER INFORMATION: Recombinant Insulin-like Growth Factor Receptor
      (IGF-1R) antisense oligodeoxynucleotide (AS-ODN)

<400> SEQUENCE: 8
aagcttcgtt gagaaact                                                 18

<210> SEQ ID NO 9
<211> LENGTH: 18
<212> TYPE: DNA
<213> ORGANISM: Artificial Sequence
<220> FEATURE:
<223> OTHER INFORMATION: Recombinant Insulin-like Growth Factor Receptor
      (IGF-1R) antisense oligodeoxynucleotide (AS-ODN)

<400> SEQUENCE: 9
ggacttgctc gttggaca                                                 18

<210> SEQ ID NO 10
<211> LENGTH: 18
<212> TYPE: DNA
<213> ORGANISM: Artificial Sequence
<220> FEATURE:
<223> OTHER INFORMATION: Recombinant Insulin-like Growth Factor Receptor
      (IGF-1R) antisense oligodeoxynucleotide (AS-ODN)

<400> SEQUENCE: 10
ggctgtctct cgtcgaag                                                 18

<210> SEQ ID NO 11
<211> LENGTH: 20
<212> TYPE: DNA
<213> ORGANISM: Artificial Sequence
<220> FEATURE:
<223> OTHER INFORMATION: IDT1220 phosphorothioate AS ODN
<220> FEATURE:
<221> NAME/KEY: misc_feature
<222> LOCATION: (1)..(20)
<223> OTHER INFORMATION: May be joined by a phosphorothioate linkage

<400> SEQUENCE: 11
cagatttctc cactcgtcgg                                               20

<210> SEQ ID NO 12
<211> LENGTH: 17
<212> TYPE: DNA
<213> ORGANISM: Artificial Sequence
<220> FEATURE:
<223> OTHER INFORMATION: Recombinant Insulin-like Growth Factor Receptor
      (IGF-1R) antisense oligodeoxynucleotide (AS-ODN)

<400> SEQUENCE: 12
ccggagccag acttcat                                                  17

<210> SEQ ID NO 13
<211> LENGTH: 20
<212> TYPE: DNA
<213> ORGANISM: Artificial Sequence
<220> FEATURE:
<223> OTHER INFORMATION: Recombinant Insulin-like Growth Factor Receptor
      (IGF-1R) antisense oligodeoxynucleotide (AS-ODN)

<400> SEQUENCE: 13
ctgctcctcc tctaggatga                                               20

<210> SEQ ID NO 14
<211> LENGTH: 15
<212> TYPE: DNA

```
<213> ORGANISM: Artificial Sequence
<220> FEATURE:
<223> OTHER INFORMATION: Recombinant Insulin-like Growth Factor Receptor
      (IGF-1R) antisense oligodeoxynucleotide (AS-ODN)

<400> SEQUENCE: 14
ccctcctccg gagcc                                                          15

<210> SEQ ID NO 15
<211> LENGTH: 18
<212> TYPE: DNA
<213> ORGANISM: Artificial Sequence
<220> FEATURE:
<223> OTHER INFORMATION: DWA phosphorothioate AS ODN
<220> FEATURE:
<221> NAME/KEY: misc_feature
<222> LOCATION: (1)..(18)
<223> OTHER INFORMATION: May be joined by a phosphorothioate linkage

<400> SEQUENCE: 15
ggaccctcct ccggagcc                                                       18

<210> SEQ ID NO 16
<211> LENGTH: 18
<212> TYPE: DNA
<213> ORGANISM: Artificial Sequence
<220> FEATURE:
<223> OTHER INFORMATION: DWA locked nucleic acid AS ODN
<220> FEATURE:
<221> NAME/KEY: misc_feature
<222> LOCATION: (1)..(6)
<223> OTHER INFORMATION: May be joined by a locked nucleic acid linkage
<220> FEATURE:
<221> NAME/KEY: misc_feature
<222> LOCATION: (6)..(13)
<223> OTHER INFORMATION: May be joined by a phosphodiester linkage
<220> FEATURE:
<221> NAME/KEY: misc_feature
<222> LOCATION: (13)..(18)
<223> OTHER INFORMATION: May be joined by a locked nucleic acid linkage

<400> SEQUENCE: 16
ggaccctcct ccggagcc                                                       18

<210> SEQ ID NO 17
<211> LENGTH: 18
<212> TYPE: DNA
<213> ORGANISM: Artificial Sequence
<220> FEATURE:
<223> OTHER INFORMATION: DWA phosphodiester AS ODN
<220> FEATURE:
<221> NAME/KEY: misc_feature
<222> LOCATION: (1)..(18)
<223> OTHER INFORMATION: May be joined by a phosphodiester linkage

<400> SEQUENCE: 17
ggaccctcct ccggagcc                                                       18

<210> SEQ ID NO 18
<211> LENGTH: 927
<212> TYPE: RNA
<213> ORGANISM: Homo sapiens

<400> SEQUENCE: 18
cuuuguuuuc uuucuuccu cacagaccuu cgggcaagga ccuucacaag ggaugcagua          60
caugcucugg cugccguugc ggaugaagcc cgaggggcac uccugcaugc acucgccguc        120
guggaucaca aaccccucgg agucgcugcu cucggcgcug aggauguugg cgcagaaguc        180
```

| | |
|---|---:|
| acgguccaca cagcgccagc ccucaaaccu guaggyguug ggcgggcagg caggcacaca | 240 |
| gacaccggca uaguaguagu ggcggcaagc uacacaggcc gugucguugu caggcgcgcu | 300 |
| gcagcugccc aggcacucgg ggugg cagca cucauuguuc ucggugcacg cccgcuuccc | 360 |
| acacgugcuu gggcacauuu ucuggcagcg guuugugguc cagcagcggu aguuguacuc | 420 |
| auuguugaug guggucuucu cacacaucgg cuucccucc augguccug acacagguc | 480 |
| cccacauucc uuuggggcu uauucccac aauguaguua uuggacaccg cauccaggau | 540 |
| cagggaccag uccacagugg agagguaaca gaggucagca uuuucacaa uccugauggc | 600 |
| cccccgagua auguuccuca gguuguaaag cccaauaucc uugagauugg ucaucucgaa | 660 |
| gaugaccagg gcguaguugu agaagaguuu ccagccgcgg augaccguga gguuggaa | 720 |
| gaggucuccg aggcucucga ggccagccac ucggaacagc agcaaguacu cgguaaugac | 780 |
| cgugagcuug gggaagcggu agcugcggua guccucggcc uuggagauga gcaggaugug | 840 |
| gagguagccc ucgaucaccg ugcaguucuc caggcgcuuc agcugcugau agucguugcg | 900 |
| gaugucgaug ccuggcccgc agauuuc | 927 |

<210> SEQ ID NO 19
<211> LENGTH: 4104
<212> TYPE: DNA
<213> ORGANISM: Homo sapiens

<400> SEQUENCE: 19

| | |
|---|---:|
| atgaagtctg gctccggagg agggtccccg acctcgctgt gggggctcct gtttctctcc | 60 |
| gccgcgctct cgctctggcc gacgagtgga gaaatctgcg ggccaggcat cgacatccgc | 120 |
| aacgactatc agcagctgaa gcgcctggag aactgcacgg tgatcgaggg ctacctccac | 180 |
| atcctgctca tctccaaggc cgaggactac cgcagctacc gcttcccaa gctcacggtc | 240 |
| attaccgagt acttgctgct gttccgagtg ctggcctcg agagcctcgg agacctcttc | 300 |
| cccaacctca cggtcatccg cggctggaaa ctcttctaca actacgccct ggtcatcttc | 360 |
| gagatgacca atctcaagga tattgggctt acaacctga ggaacattac tcgggggggcc | 420 |
| atcaggattg agaaaaatgc tgacctctgt tacctctcca ctgtggactg gtccctgatc | 480 |
| ctggatgcgg tgtccaataa ctacattgtg gggaataagc ccccaaagga atgtggggac | 540 |
| ctgtgtccag ggaccatgga ggagaagccg atgtgtgaga agaccaccat caacaatgag | 600 |
| tacaactacc gctgctggac cacaaaccgc tgccagaaaa tgtgcccaag cacgtgtggg | 660 |
| aagcgggcgt gcaccgagaa caatgagtgc tgccaccccg agtgcctggg cagctgcagc | 720 |
| gcgcctgaca acgacacggc ctgtgtagct tgccgccact actactatgc cggtgtctgt | 780 |
| gtgcctgcct gccgcccaa cacctacagg tttgagggct ggcgctgtgt ggaccgtgac | 840 |
| ttctgcgcca acatcctcag cgccgagagc agcgactccg aggggtttgt gatccacgac | 900 |
| ggcgagtgca tgcaggagtg cccctcgggc ttcatccgca cggcagcca gagcatgtac | 960 |
| tgcatcccctt gtgaaggtcc ttgcccgaag gtctgtgagg aagaaaagaa aacaaagacc | 1020 |
| attgattctg ttacttctgc tcagatgctc caaggatgca ccatcttcaa gggcaatttg | 1080 |
| ctcattaaca tccgacgggg gaataacatt gcttcgagagc tggagaactt catgggggctc | 1140 |
| atcgaggtgg tgacgggcta cgtgaagatc cgccattctc atgccttggt ctccttgtcc | 1200 |
| ttcctaaaaaa accttcgcct catcctagga gaggagcagc tagaagggaa ttactccttc | 1260 |
| tacgtcctcg acaaccagaa cttgcagcaa ctgtgggact gggaccaccg caacctgacc | 1320 |
| atcaaagcag ggaaaatgta ctttgctttc aatcccaaat tatgtgtttc cgaaatttac | 1380 |

-continued

```
cgcatggagg aagtgacggg gactaaaggg cgccaaagca aagggacat aaacaccagg    1440 aacaacgggg agagagcctc ctgtgaaagt gacgtcctgc atttcacctc caccaccacg    1500
tcgaagaatc gcatcatcat aacctggcac cggtaccggc cccctgacta cagggatctc    1560
atcagcttca ccgtttacta caaggaagca ccctttaaga atgtcacaga gtatgatggg    1620
caggatgcct gcggctccaa cagctggaac atggtggacg tggacctccc gcccaacaag    1680
gacgtggagc ccggcatctt actacatggg ctgaagccct ggactcagta cgccgtttac    1740
gtcaaggctg tgaccctcac catggtggag aacgaccata tccgtggggc caagagtgag    1800
atcttgtaca ttcgcaccaa tgcttcagtt ccttccattc ccttggacgt tctttcagca    1860
tcgaactcct cttctcagtt aatcgtgaag tggaaccctc cctctctgcc caacggcaac    1920
ctgagttact acattgtgcg ctggcagcgg cagcctcagg acggctacct ttaccggcac    1980
aattactgct ccaaagacaa aatccccatc aggaagtatg ccgacggcac catcgacatt    2040
gaggaggtca cagagaaccc caagactgag gtgtgtggtg gggagaaagg gccttgctgc    2100
gcctgcccca aaactgaagc cgagaagcag gccgagaagg aggaggctga ataccgcaaa    2160
gtctttgaga atttcctgca caactccatc ttcgtgccca gacctgaaag gaagcggaga    2220
gatgtcatgc aagtggccaa caccaccatg tccagccgaa gcaggaacac cacggccgca    2280
gacacctaca acatcaccga cccggaagag ctggagacag agtacccttt ctttgagagc    2340
agagtggata caaggagag aactgtcatt tctaaccttc ggccttttca cattgtaccgc    2400 atcgatatcc acagctgcaa ccacgaggct gagaagctgg gctgcagcgc ctccaacttc    2460
gtctttgcaa ggactatgcc cgcagaagga gcagatgaca ttcctgggcc agtgacctgg    2520
gagccaaggc ctgaaaactc catctttta aagtggccgg aacctgagaa tcccaatgga    2580
ttgattctaa tgtatgaaat aaaatacgga tcacaagttg aggatcagcg agaatgtgtg    2640
tccagacagg aatacaggaa gtatggaggg gccaagctaa accggctaaa cccggggaac    2700
tacacagccc ggattcaggc cacatctctc tctgggaatg gtcgtggac agatcctgtg    2760 ttcttctatg tccaggccaa aacaggatat gaaaacttca tccatctgat catcgctctg    2820
cccgtcgctg tcctgttgat cgtgggaggg ttggtgatta tgctgtacgt cttccataga    2880
aagagaaata acagcaggct ggggaatgga gtgctgtatg cctctgtgaa cccggagtac    2940
ttcagcgctg ctgatgtgta cgttcctgat gagtgggagg tggctcggga gaagatcacc    3000
atgagccggg aacttgggca ggggtcgttt gggatggtct atgaaggagt tgccaagggt    3060
gtggtgaaag atgaacctga aaccagagtg gccattaaaa cagtgaacga ggccgcaagc    3120
atgcgtgaga ggattgagtt tctcaacgaa gcttctgtga tgaaggagtt caattgtcac    3180
catgtggtgc gattgctggg tgtggtgtcc caaggccagc caacactggt catcatggaa    3240
ctgatgacac ggggcgatct caaaagttat ctccggtctc tgaggccaga aatggagaat    3300
aatccagtcc tagcacctcc aagcctgagc aagatgattc agatggcggg agagattgca    3360
gacggcatgg cataacctcaa cgccaataag ttcgtccaca gagaccttgc tgcccggaat    3420
tgcatggtag ccgaagattt cacagtcaaa atcggagatt ttggtatgac gcgagatatc    3480
tatgagacag actattaccg gaaggaggg aaagggctgc tgcccgtgcg ctggatgtct    3540
cctgagtccc tcaaggatgg agtcttcacc acttactcgg acgtctggtc cttcggggtc    3600
gtcctctggg agatcgccac actggccgag cagccctacc agggcttgtc caacgagcaa    3660
gtccttcgct tcgtcatgga gggcggcctt ctggacaagc cagacaactg tcctgacatg    3720
```

```
ctgtttgaac tgatgcgcat gtgctggcag tataacccca agatgaggcc ttccttcctg    3780
gagatcatca gcagcatcaa agaggagatg gagcctggct tccgggaggt ctccttctac    3840
tacagcgagg agaacaagct gcccgagccg gaggagctgg acctggagcc agagaacatg    3900
gagagcgtcc ccctggaccc ctcggcctcc tcgtcctccc tgccactgcc cgacagacac    3960
tcaggacaca aggccgagaa cggccccggc cctggggtgc tggtcctccg cgccagcttc    4020
gacgagagac agccttacgc ccacatgaac gggggccgca agaacgagcg ggccttgccg    4080
ctgccccagt cttcgacctg ctga                                          4104
```